United States Patent [19]

Alain et al.

[11] Patent Number: 5,116,833
[45] Date of Patent: May 26, 1992

[54] ANTIBIOTIC C-3 DITHIOACETAL-SUBSTITUTED CARBAPENEM COMPOUNDS, COMPOSITIONS, AND METHODS OF USE THEREOF

[75] Inventors: Martel Alain, Delson; Carol Bachand, Candiac; Jean-Paul Daris, St. Hubert, all of Canada

[73] Assignee: Bristol-Myers Squibb Company, New York, N.Y.

[21] Appl. No.: 600,359

[22] Filed: Oct. 19, 1990

[51] Int. Cl.$^5$ .................. C07D 487/04; A61K 31/40
[52] U.S. Cl. ..................... 514/210; 540/350
[58] Field of Search ............... 540/350; 514/210

[56] References Cited

U.S. PATENT DOCUMENTS

| | | | |
|---|---|---|---|
| 4,413,000 | 11/1983 | Eglington | 514/210 |
| 4,552,873 | 11/1985 | Myadera et al. | 514/210 |
| 4,683,301 | 7/1987 | Kim | 540/350 |
| 4,880,922 | 11/1989 | Dextraze | 540/350 |

FOREIGN PATENT DOCUMENTS 0168707 1/1986 European Pat. Off. .
0169410 1/1986 European Pat. Off. .

OTHER PUBLICATIONS

Sato et al., *The Journal of Antibiotics*, 40, 4, pp. 483–495 (1987) "Modification of the Cysteamine Side Chain in Thienamycin II".

*Primary Examiner*—Nicholas S. Rizzo
*Assistant Examiner*—Jyothsna Venkat
*Attorney, Agent, or Firm*—W. T. Han

[57] ABSTRACT

A dithioacetal carbapenem of the formula

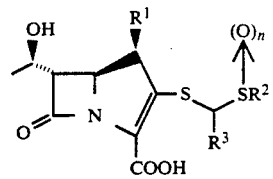

(I)

in which
$R^1$ is hydrogen or $C_{1-6}$ alkyl;
n is 0, 1 or 2;
$R^3$ is hydrogen or $C_{1-6}$ alkyl;
$R^2$ is
  $C_{1-6}$ alkyl,
  phenyl optionally substituted with cyano, —$CO_2NH_2$, —$CH_2OH$, —$CH_2NH_2$, —$CONHNH_2$ or with up to 5 halogen atoms, $C_{1-6}$ alkyl or $C_{1-6}$ alkyloxy groups,
  phenylmethyl optionally substituted with up to 5 halogen atoms, $C_{1-6}$ alkyl or $C_{1-6}$ alkyloxy groups on the phenyl ring, or
  a radical represented by the formula $$-(CH_2)_p-X$$

in which p is 0 or 1; X is five-membered aromatic heterocyclic ring containing up to 1 sulfur, 1 oxygen or 4 nitrogen atoms, optionally substituted with a $C_{1-6}$ alkyl group, or six-membered aromatic heterocyclic ring containing up to 4 nitrogen atoms, optionally substituted with a $C_{1-6}$ alkyl group.

or a non-toxic pharmaceutically acceptable salt, physiologically hydrolyzable ester or solvate thereof.

39 Claims, No Drawings

ANTIBIOTIC C-3 DITHIOACETAL-SUBSTITUTED CARBAPENEM COMPOUNDS, COMPOSITIONS, AND METHODS OF USE THEREOF

BACKGROUND OF THE INVENTION

1. Field of the Invention

The present invention relates to novel orally bioavailable carbapenem antibiotics having a dithioacetal moiety in the 3-position and non-toxic pharmaceutically acceptable salts thereof. The carbapenems of the instant invention have been found to have antimicrobial activity. Therefore, the present carbapenem antibiotics and pharmaceutical compositions thereof are useful in the treatment of antibacterial infections in humans and other animals, either alone or in combination with other antibiotics.

Also disclosed herein are processes for the preparation of said carbapenem antibiotics and to certain novel intermediates.

2. Nomenclature

The terminology for compounds of this class may either be based upon the root name "carbapenem" which employs a trivial system of nomenclature or on the systematic name according to Chemical Abstracts. In the present application, the positions are numbered according to the Chemical Abstract system, for example, 3-$R^3$-4-$R^2$-6-$R^1$-7-oxo-1-azabicyclo[3.2.0]hept-2-ene-2-carboxylic acid as shown in the following formula

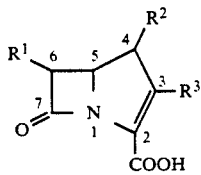

The term "carbapenem", as used herein as a class of compounds, is intended to be used interchangeably with the name 7-oxo-1-azabicyclo[3.2.0]hept-2-ene-2-carboxylic acid. However, in all instances, the numbering system employed will be the numbering system according to Chemical Abstracts as illustrated above.

3. Disclosure Statement

A great number of carbapenem antibiotics are known in the art. This class of antibiotics is typefied by thienamycin (U.S. Pat. No. 3,950,357 issued Apr. 13, 1976 to Kahan et al.) which was first isolated from fermentation and exhibits a broad spectrum of antibiotic activity. Imipenem (U.S. Pat. No. 4,194,047 issued Mar. 18, 1980 to Christensen et al.), a chemically more stable derivative of thienamycin, was subsequently developed.

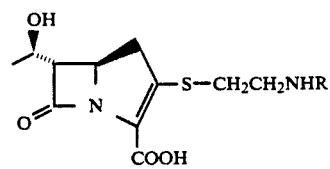

thienamycin; R = H
imipenem; R = CH=NH

More recent developments include 3-(substituted thio)-4-methylcarbapenems of formula II which is disclosed in Shih et al., *Heterocycles*, 21, 29–40 (1984).

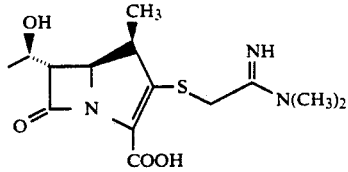

U.S. Pat. No. 4,683,301 issued on Jul. 28, 1987 to Choung relates, inter alia, to carbapenems of formula III

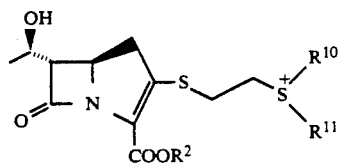

in which and $R^{10}$ and $R^{11}$ each is substituted or unsubstituted alkyl, cycloalkyl, phenyl or taken together constitute $C_{5-6}$ alkylidene.

U.S. Pat. No. 4,880,922, issued on Nov. 14, 1989 to Dextraze, relates to carbapenems of the formula

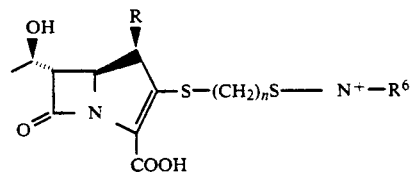

in which R is hydrogen or alkyl, $R^6$ is $C_{1-6}$ alkyl; n is 1 to 3 and $N^+$ represents an aromatic 5- or 6- membered N-containing heterocyclic ring containing 0-3 additional hetero atoms selected from O, S or N, said aromatic ring being optionally substituted at available ring carbon or nitrogen atoms by $C_{1-4}$ substituents, and said ring being attached to S through a ring carbon atoms and having a ring nitrogen which is quaternized by the group $R^6$.

European Patent Applications Nos. 169,410 and 168,707 both published on Jul. 2, 1984 disclose a broad class of carbapenems among which are compounds of the formula

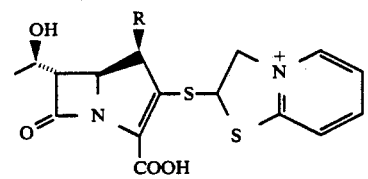

in which R is hydrogen or methyl.

Another relevant art of the instant invention can be found in Sato et al., in *The Journal of Antibiotics*, 40, 4, pp 483–495 (1987) in which carbapenems of the following structures are disclosed

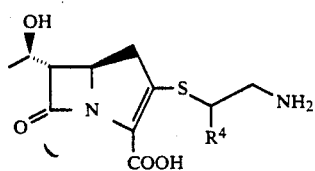

R⁴:

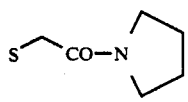

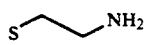

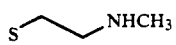

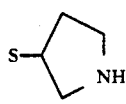

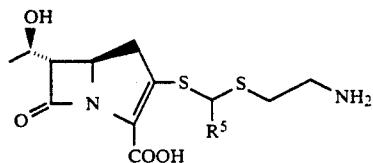

R⁵:

CH₂OH

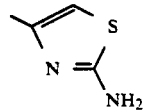

Despite general improvements in stability and spectrum of antibiotic activity of carbapenems since imipenem and thienamycin, there is still no reports of carbapenems having any significant oral bioavailability and oral activity. To our great surprise, certain dithioacetal and dithioketal carbapenems of the invention have shown significant oral bioavailability and oral antibiotic activity. Thus, it is the object of the present application to provide a novel class of carbapenms which have been discovered to have the unexpected properties in addition to potent in vitro antimicrobial activity. Thus, the compounds of the present invention are greatly useful in the treatment of infectious diseases in humans and other animals.

SUMMARY OF THE INVENTION

The present invention provides novel 3-dithioacetal substituted carbapenem antibiotics having the formula

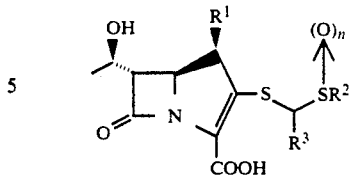

in which
$R^1$ is hydrogen or $C_{1-6}$ alkyl;
n is 0, 1 or 2;
$R^3$ is hydrogen or $C_{1-6}$ alkyl;
$R^2$ is
  $C_{1-6}$ alkyl,
  phenyl optionally substituted with cyano, —CONH₂, —CH₂OH, —CH₂NH₂, —CONHNH₂ or with up to 5 halogen atoms, $C_{1-6}$ alkyl or $C_{1-6}$ alkyloxy groups,
  phenylmethyl optionally substituted with up to 5 halogen atoms, $C_{1-6}$ alkyl or $C_{1-6}$ alkyloxy groups on the phenyl ring, or
  a radical represented by the formula $$-(CH_2)_p-X$$

in which p is 0 or 1; X is five-membered aromatic heterocyclic ring containing up to 1 sulfur, 1 oxygen or 4 nitrogen atoms, optionally substituted with a $C_{1-6}$ alkyl group, or six-membered aromatic heterocylic ring containing up to 4 nitrogen atoms, optionally substituted with a $C_{1-6}$ alkyl group.

In another aspect, this invention relates to compounds of formula I and their non-toxic pharmaceutically acceptable salts, physiologically hydrolyzable esters or solvates.

Representative carbapenems of this invention were selected for testing and were shown to display potent antimicrobial activity and unexpected oral bioavailability. Thus, further aspects of the invention are pharmaceutical compositions comprising said carbapenem antibiotics and to methods of treatment comprising administering said carbapenem antibiotics or pharmaceutical compositions thereof.

DETAILED DESCRIPTION OF THE INVENTION

The present invention provides novel 3-dithioacetal substituted carbapenem antibiotics having the formula

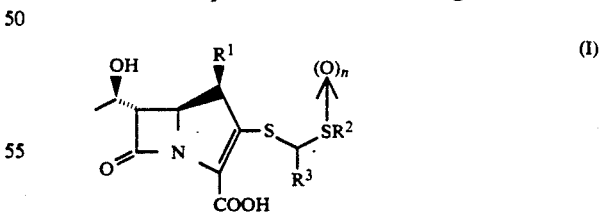

in which $R^1$, $R^2$, $R^3$ and n are as defined above.

More preferred compounds of formula I are those in which $R^1$ is hydrogen or methyl; n is 0 or 1; $R^3$ is hydrogen or $C_{1-6}$ alkyl; $R^2$ is $C_{1-6}$ alkyl, phenyl optionally substituted with cyano, —CONH₂, —CH₂OH, —CH₂NH₂, —CONHNH₂ or with up to 5 halogen atoms or $C_{1-6}$ alkyl groups, phenylmethyl optionally substituted with up to 5 halogen atoms or $C_{1-6}$ alkyl groups on the phenyl ring, or a radical represented by the formula —(CH$_2$)$_p$—X in which p is 0 or 1; X is pyridyl, furyl or a radical of the formulae

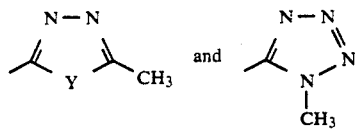

in which Y is sulfur or oxygen;

The present application also provides useful intermediates and processes for the preparation of compounds of formula I and their intermediates.

In the above definition of the compounds represented by formula I, C$_{1-6}$ alkyl refers to straight and branched chain alkyl groups such as methyl, ethyl, n-propyl, isopropyl, n-butyl, n-penptyl, n-hexyl, 3-methylpentyl, and like alkyl groups; phenyl substituted with up to 5 halogen atoms or C$_{1-6}$ alkyl groups refers to groups such as 2,3,4,5,6-hexafluorophenyl, 2-fluoro-3-methylphenyl, 2-ethyl-3-methylphenyl, 4-methylphenyl, 4-bromo-3-chloro-5-methylphenyl, 4-t-butylphenyl, 3,5-dichlorophenyl, and like groups, five-membered aromatic heterocyclic ring containing up to 1 sulfur, 1 oxygen or 4 nitrogen atoms refers to groups such as thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, and like rings; six-membered aromatic heterocyclic ring containing up to 4 nitrogen atoms refers to such aromatic rings as pyridyl, pyrimidyl, pyrazinyl, pyridazinyl, triazinyl, tetrazinyl, and like rings; halogen refers to iodo, chloro, fluoro, or bromo.

The term "non-toxic pharmaceutically acceptable salt" as used herein and in the claims is intended to include non-toxic acid and base salts, and salts of zwitterionic species. Salts with a base is intended to include inorganic metallic salts such as sodium, potassium, calcium and magnesium, the ammonium salt, and salts with non-toxic amines such as trialkylamines, pyridine, picoline, dibenzylamine, ethanolamine, N-methylmorpholine and other amines which have been used to form salts of carboxylic acids. Salts with an acid is intended to include inorganic acid salts such as hydrochloride, hydrobromide, hydroiodide, sulfate, phosphate, and the like, and organic acid salts such as formate, acetate, maleate, citrate, succinate, ascorbate, lactate, fumarate and tartrate which have been used to form salts of basic amines.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C$_{1-6}$ alkyl, benzyl, 4-methoxybenzyl, indanyl, phthalidyl, methoxymethyl, C$_{1-6}$ alkanoyloxy(C$_{1-6}$)alkyl, e.g. acetoxymethyl, pivaloyloxymethyl or propionyloxymethyl, C$_{1-6}$ alkoxycarbonyloxy )alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)methyl and other physiologically hydrolyzable esters known and used in the penicillin and cephalosporin arts. Such esters are prepared by conventional techniques known in the art.

The compounds of the present invention have several asymmetric carbon atoms and can thus exist in several stereochemical forms. The invention includes the mixture of isomers and the individual stereoisomers. The most preferred compounds of formula I have the 4R, 5S, 6S configuration on the 1-azabicyclo[3.2.0]heptane ring structure. In addition, the 3-substituents may contain an asymmetric carbon atom and/or sulfinyl group which exists in either the R or S configuration. It is intended that both the R and S isomers of the 3-substituents are included in the present invention, for example, the R and S isomers of 3-[[[(p-chlorophenyl)sulfinyl]-methyl]thio], 3-[[[[(pyridin-3-yl)methyl]sulfinyl]methyl]thio], 3-[[(methylsulfinyl)methyl]thio]and 3-[[1-(methylthio)ethyl]thio]substituents.

The novel carbapenem derivatives of general formula I or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the physician. In general, however, the compounds may be administered parenterally or orally to mammalian hosts in an amount of from about 5 to 200 mg/kg/day. Administration is generally carried out in divided doses, e.g. three to four times a day.

The carbapenem compounds of formula I may be prepared by alkylating an intermediate represented by formula IV with an alkylating agent V, as shown in Scheme A.

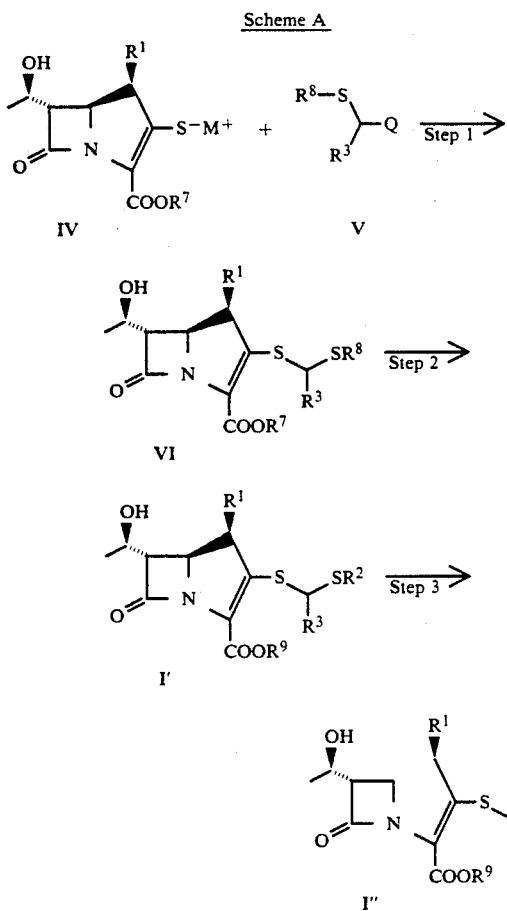

Scheme A

In the scheme, $R^1$, $R^2$, $R^3$ and n represent groups as previously defined. $M^+$ is a metal cation or hydrogen preferred metal cation being silver. When M is hydrogen Step 1 can be effected in the presence of an amine base; a preferred amine base being tri($C_{1-6}$)alkyl amine, a more preferred base being diisopropylethyl amine. In formula V, Q represents a leaving groups such as iodo, bromo or chloro.

In formulas IV and VI, $R^7$ is a conventional carboxy protecting group. Conventional carboxy-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl )alkyl, ring substituted phenyl($C_{1-6}$)alkyl, e.g., benzyl, 4-methoxybenzyl, 4-nitrobenzyl (p-nitrobenzyl), 2-nitrobenzyl, benzyhydryl and trityl, methoxymethyl, 2,2,2-trichloroethoxycarbonyl, benzyloxymethyl, $C_{1-6}$ alkanoyloxy($C_{1-6}$)alkyl such as acetoxymethyl, propionyloxymethyl, $C_{2-6}$ alkenyl such as vinyl and allyl. Particularly advantageous carboxy protecting groups are benzyl, 4-nitrobenzyl, 2-nitrobenzyl, 2,4-dimethoxybenzyl, 4-methoxybenzyl, allyl and substituted allyl. Other suitable carboxy protecting groups are disclosed in "Protective Groups in Organic Synthesis", Theodora W. Greene (John Wiley & Sons, 1981), Chapter 5.

In formulas V and VI, $R^8$ is $C_{1-6}$ alkyl; phenylmethyl optionally substituted with up to 5 halogen atoms, $C_{1-6}$ alkyloxy or $C_{1-6}$ alkyl groups on the phenyl ring; phenyl optionally substituted with cyano, $-CONH_2$ or with up to 5 halogen atoms, $C_{1-6}$ alkyl or $C_{1-6}$ alkyloxy groups; a radical of the formula

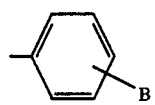

in which B represents a functional group which can be converted into $-CH_2OH$, $-CH_2NH_2$ or $-CONHNH_2$; or a radical of the formula

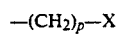

wherein p and X are as defined above.

The conversion of a group B into the desired radicals is preferably effected concurrently with the removal of a carboxy protecting group $R^7$ in Step 2. For example, when $R^7$ is p-nitrobenzyl radical, the removal can be achieved by catalytic hydrogenolysis. Particularly convenient precursors to the groups $-CH_2OH$, $-CH_2NH_2$ and $-CONHNH_2$ which can be converted during the hydrogenolysis are $-CH_2OCO_2PNB$, $-CH_2N_3$ and $-CONHNHCO_2PNB$, respectively.

In formulas I' and I", $R^9$ is hydrogen or a cation of base salt. For example when the removal of a protecting group $R^7$ is done in the presence of sodium or potassium cation, $R^9$ becomes sodium or potassium, respectively. If desired, a sulfur atom can be oxidized to a sulfinyl or sulfonyl group in Step 3 by a well developed technique in the art.

The common intermediates represented by formula IV in Scheme A in which $M^+$ is $Ag^+$ and hydrogen can be prepared by reaction sequences shown in Scheme B and Scheme C, respectively.

Scheme B

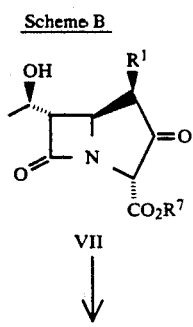

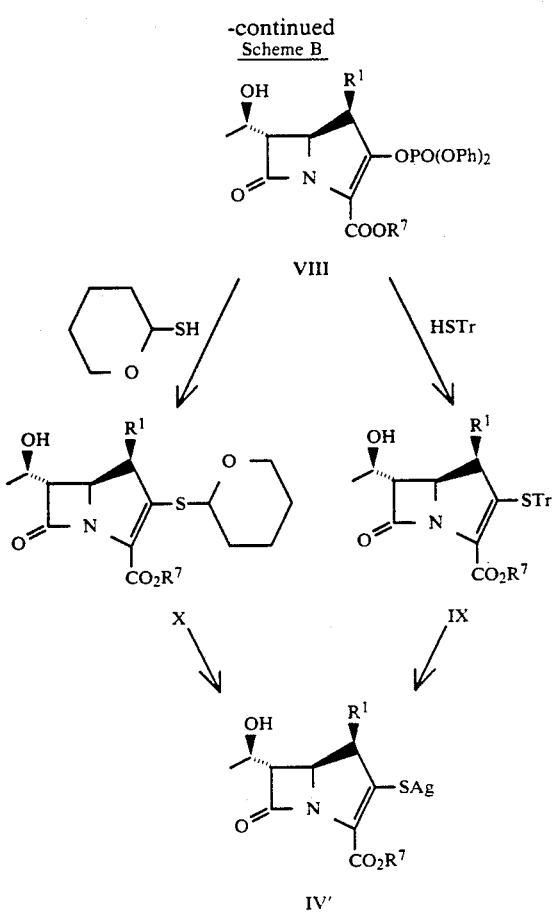

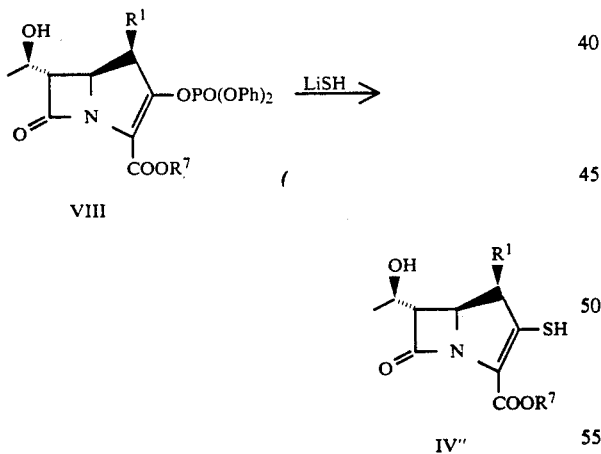

In Schemes B and C, $R^1$ and $R^9$ are as defined previously. The conversion of a compound of formula VII to a compound of formula VIII can be conveniently carried out with ClPO(OPh)$_2$ and DIPEA. The radical —OPO(OPh)$_2$, which is a leaving group, is displaced with tetrahydropyran-2-yl mercaptan or TrSH in the presence of base such as DIPEA. Alternatively, the radical —OPO(OPh)$_2$ is displaced with LiSH. The sulfur-carbon bonds in compounds of formulas X and IX are cleaved with AgNO$_3$.

The specific examples which follow illustrate the synthetic steps shown in Schemes A, B and C and are not to be construed as limiting the invention in sphere or scope. The methods disclosed may be adopted to variations in order to produce compounds embraced by this invention but not specifically disclosed. Furthermore, variations of the methods to produce the same compounds in somewhat different fashion will also be evident to one skilled in the art.

The abbreviations used herein are conventional abbreviations well-known to those in the art. Some which are included below.

| | Abbreviations |
|---|---|
| min | minute(s) |
| h | hour(s) |
| DIPEA | N,N-diisopropylethylamine (or more commonly as diisopropylethylamine) |
| THF | tetrahydrofuran |
| Ph or Φ | phenyl |
| THP | tetrahydropyran |
| PNB | p-nitrobenzyl |
| Pd/C | palladium on carbon |
| ether | diethyl ether |
| DMF | dimethylformamide |
| trityl or Tr | triphenylmethyl |
| DMAP | 4-dimethylaminopyridine |
| psi | pounds per square inch |
| eq. | equivalent(s) |
| Ar | aryl |
| R.T. or rt | room temperature |

DESCRIPTION OF SPECIFIC EMBODIMENTS

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethysulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value. Celite is a registered trademark of the Johns-Manville Products Corporation for diatomaceous earth.

EXAMPLE 1 p-Nitrobenzyl (4R,5S,6S)-6-[1'(R)-hydroxyethyl]-4-methyl-3-silver mercapto-7-oxo-1-azabicyclo[3.2.0]hept-2-ene-2-carboxylate

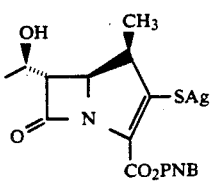

Method I

Step A p-Nitrobenzyl (4R,5S,6S)-6-[1'(R)-hydroxyethyl]-4-methyl-3-[(tetrahydropyran-2-yl)thio]-7-oxo-1-azabicyclo-[3.2.0]hept-2-ene-2-carboxylate

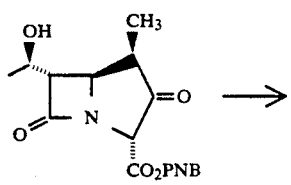

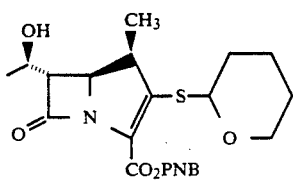

A cold (ice-MeOH bath) solution of p-nitrobenzyl (2R, 4R,5S,6S)-6-[1'(R)-hydroxyethyl]-4-methyl-3,7-dioxo-1-azabicyclo[3.2.0]heptan-2-carboxylate (41.33 g, 114.2 mmol) in dry $CH_3CN$ (300 mL) was treated dropwise with $ClPO(O\phi)_2$ (27.4 mL, 131 mmol) and with DIPEA 24.0 mL, 137 mmol). The mixture was stirred for 30 min to allow the formation of enol phosphate which was then treated dropwise with tetrahydropyran-2-yl mercaptan (15 mL, 137 mmol) and with DIPEA (25 mL, 143 mmol). The mixture was then stirred for 1.5 h ($-5°$ C.-$0°$ C.), treated again with more thiol (3.7 mL, 34 mmol) and DIPEA (6 mL, 34 mmol), and left at $-20°$ C. for 18 h. It was diluted with ice cold $H_2O$ (600 mL) and extracted with EtOAc (3×400 mL). The ethyl acetate extracts were combined, washed with cold 1N HCl (400 mL), cold $H_2O$ (400 mL), cold 1M aqueous $NaHCO_3$ (400 mL), cold brine (400 mL), dried ($MgSO_4$), and treated with neutral activated charcoal. The residue obtained upon solvent evaporation was diluted with EtOAc (70 mL) and with petroleum ether (750 mL) to allow the precipitation of the title material. This process was repeated twice to give the pure desired material (54.3 g, 100%).

IR ($CH_2Cl_2$) $\nu_{max}$: 3600–3400 (OH), 1770 and 1715 $cm^{-1}$ (C=O);

$^1$H NMR ($CDCl_3$, 200 MHz) δ: 8.22, 8.15 (2H, m, PNB-H), 7.67–7.6 (2H, m, PNB-H), 5.5, 5.45, 5.25, 5.17 (2H, ABq, J=14 Hz, $CH_2$-PNB), 4.3–4.2 (1H, m, H-1'), 4.2 (1H, dd, J=2.7 Hz, J=6.2 Hz, H-5), 4.15–3.9 (1H, m, H-2 THP), 3.75–3.4 (3H, m, H-4 and $CH_2O$), 3.05 (1H, dd, J=2.7 Hz, H-6), 2.0–1.5 (7H, m, OH, $(CH_2)_3$), 1.37 (3H, d, J=6.3 Hz, $CH_3$), 1.29 ppm (3H, d, J=7.3 Hz, $CH_3$).

Step B p-Nitrobenzyl (4R,5S,6S)-6-[1'(R)-hydroxyethyl]-4-methyl-3-silver mercapto-7-oxo-1-azabicyclo[3.2.0]hept-2-ene-2-carboxylate

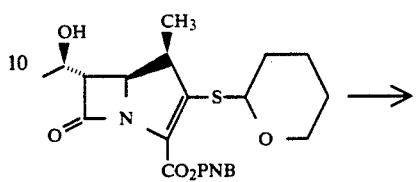

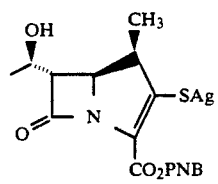

A cold (ice bath) solution of p-nitrobenzyl (4R,5S,6S)-6-[1'(R)-hydroxyethyl]-4-methyl-3-[(tetrahydropyran-2-yl)thio -7-oxo-1-azabicyclo[3.2.0]hept-2-ene-2-carboxylate (52.7 g, 114 mmol) in dry $CH_3CN$ (250 mL) was treated with a cold solution of $AgNO_3$ (29.3 g, 171 mmol) in MeOH (250 mL) and pyridine (13.8 mL, 171 mmol). The resulting mixture was stirred for 30 min and then poured into a vigorously stirred ice water (500 mL). The solid was filtered and triturated with cold $H_2O$ (500 mL). This solid was again collected by filtration, washed with cold water (500 mL), ether (2×500 mL), and dried to give the title material as a solid (55 g, 99.5%).

IR (Nujol) $\nu_{max}$: 3700–3200 (OH), 1775, 1670 (C=O) and 1520 $cm^{-1}$ ($NO_2$).

Method II

Step A p-Nitrobenzyl (4R,5S,6S)-6-[1'(R)-hydroxyethyl]-4-methyl-3-[(triphenylmethyl)thio]-7-oxo-1-azabicyclo-[3.2.0]hept-2-ene-2-carboxylate

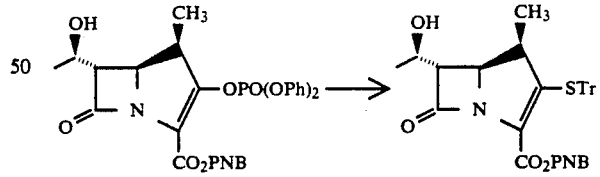

A cold (ice bath) solution of p-nitrobenzyl (4R,5S,6S)-3-diphenoxophosphorousoxy-6-[1'(R)-hydroxyethyl]-4-methyl-7-oxo-1-azabicyclo[3.2.0]hept-2-ene-2-carboxylate (4.8 g, 9.6 mmol) in DMF (50 mL) was treated with TrSH (7.96 g, 28.8 mmol) and dropwise with DIPEA (5.1 mL, 29.0 mmol) and stirred for 30 min. The ice bath was removed, and the mixture was stirred for 48 h after which it was diluted with ice water (50 mL). The aqueous mixture was extracted with a 1/1 mixture of EtOAc/ether (4×20 mL). The organic layers were combined, washed with cold $H_2O$ (3×50 mL) and dried ($MgSO_4$). The residue was passed through a pad of silica gel (125 g of silica; first eluted with CH$_2$Cl$_2$ followed successively by 5%, 10% and 15% EtOAc/CH$_2$Cl$_2$) to give the title material (1.15 g, 19%).

IR (CH$_2$Cl$_2$) $\nu_{max}$: 3600, 3300 (OH), 1775, 1730 (C=O) and 1520 cm$^{-1}$ (NO$_2$);

$^1$H NMR (CDCl$_3$, 200 MHz) δ:8.27–8.02 (2H, m, PNB-H), 7.60–7.4 (2H, m, PNB-H), 7.4–7.1 (15H, m, trityl H), 5.52, 5.35 5.18, 5.00 (2H, ABq, J=13.8 Hz, CH$_2$), 4.25–3.9 (1H, m, H-1'), 3.57 (1H, dd, J=2.5 Hz, J=8.9 Hz, H-5), 3.07 (1H, dd, J=2.5 Hz, J=7.2 Hz, H-6), 2.7–2.25 (1H, m, H-4), 1.70 (1H, bs, OH), 1.26 (3H, d, J=6.2 Hz, CH$_3$), 0.98 ppm (3H, d, J=7.1 Hz, CH$_3$).

Step B p-Nitrobenzyl (4R,5S,6S)-6-[1'(R)-hydroxyethyl]-4-methyl-3-silver mercapto-7-oxo-1-azabicyclo[3.2.0]hept-2-ene-2-carboxylate

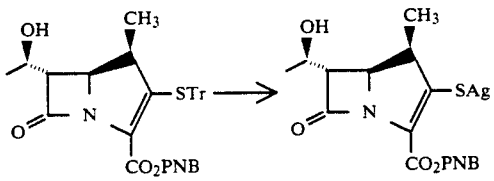

A cold (ice bath) solution of p-nitrobenzyl (4R,5S,6S)-6-[1'(R)-hydroxyethyl]-4-methyl-3-[(triphenylmethyl)thio]-7-oxo-1-azabicyclo[3.2.0]hept-2-ene-2-carboxylate (842 mg, 1.36 mmol) in anhydrous CH$_3$CN (5 mL) was treated dropwise with AgNO$_3$ (345 mg, 2.03 mmol) in MeOH (5 mL) and pyridine (0.16 mL, 2.03 mmol). After the addition, the mixture was stirred for 1.5 h at 5° C. and then diluted with cold H$_2$O (10 mL) and stirred for 5 more min. The solid was collected by filtration, washed with cold H$_2$O (2×20 mL), ether (2×20 mL), and dried under high vacuum to give the title material (604 mg, 92%) as a pale brown solid.

IR (Nujol) $\nu_{max}$: 3650–3200 (OH), 1760, 1670 (C=O) and 1520 cm$^{-1}$ (NO$_2$).

EXAMPLE 2

Allyl (4R 5S 6S)-6-1'(R)-hydroxyethyl]-4-methyl-3-silver mercapto-7-oxo-1-azabicyclo[3.2.0hept-2-ene-2-carboxylate

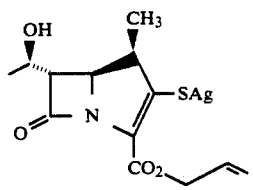

Step A

Allyl (4R,5S,6S)-6-[1'(R)-hydroxyethyl]-4-methyl-3-[(tetrahydropyran-2-yl)thio]-7-oxo-1-azabicyclo[3.2.0]-hept-2-ene-2-carboxylate

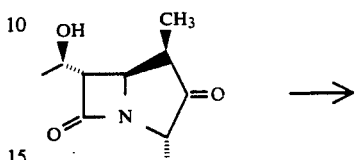

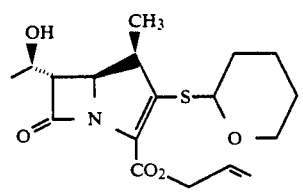

A cold (ice-MeOH bath) solution of allyl (2R, 4R,5S,6S)-6-[1'(R)-hydroxyethyl]-4-methyl-3,7-dioxo-1-azabicyclo[3.2.0]heptane-2-carboxylate (13.6 g, 50.8 mmol) in CH$_3$CN (200 mL) was treated dropwise with ClPO(Oφ)$_2$ (11.8 mL, 57.1 mmol), DIPEA (10.3 mL, 58.7 mmol), and a trace amount of DMAP (15 mg) and stirred for 1 h at −10° C. -0<° C. The resulting enol phosphate solution was purged with argon gas (15 min) and treated dropwise successively with tetrahydropyran-2-yl mercaptan (6.6 g, 56 mmol) in CH$_3$CN (25 mL) and DIPEA (10.7 mL, 61.0 mmol). The mixture was stirred for 1 h at 5° C. and for 20 h at c.a. 22° C. The mixture was cooled with an ice bath, treated with additional thiol (1.5 g, 12.7 mmol) in CH$_3$CN (5 mL) and DIPEA (2.28 mL, 13.0 mmol), and stirred for 8 h at 22° C. and then at 5° C. for 18 h. The mixture was diluted with ice cold H$_2$O (250 mL) and extracted with EtOAc (3×200 mL). The ethyl acetate extracts were combined, washed with cold 0.5N aqueous HCl (1×200 mL), water (1×200 mL), 0.5M aqueous NaHCO$_3$ (1×200 mL), water (1×200 mL), brine (200 mL), and dried (MgSO$_4$). The residue was passed through a pad of silica gel (200 g of silica; eluted first with CH$_2$Cl$_2$ and then successively with 2%, 5%, 10% and 25% EtOAc/CH$_2$Cl$_2$) to give the title material (13.9 g, 75%), contaminated with some of the enol phosphate, as a mixture of diastereomers.

IR (neat) $\nu_{max}$: 3600–3200 (OH), 1770 and 1720 cm$^{-1}$ (C=O);

$^1$H NMR (CDCl$_3$, 200 MHz) δ: 6.1–5.7 (1H, m, vinylic H), 5.5–5.1 (2H, m, vinylic H), 4.9–4.5 (2H, m, CH-vinyl), 4.3–3.9 (4H, m, H-1', H-5, THP-H$_{2,6}$), 3.7–3.4 (2H, m, THP-H$_6$, H-4), 3.3–3.2 (1H, m, H-6), 2–1.5 (7H, 1 m, (CH$_2$)$_3$ and OH), 1.3–1.1 ppm (6H, m, CH$_3$).

Step B

Allyl (4R,5S,6S)-6-[1'(R)-hydroxyethyl]-4-methyl-3-silver mercapto-7-oxo-1-azabicyclo[3.2.0]hept-2-ene-2-carboxylate

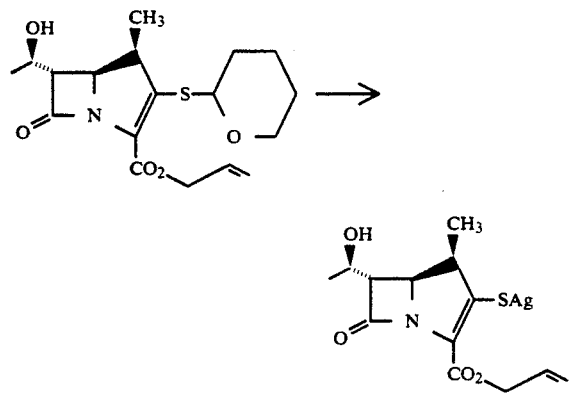

A solution of AgNO₃ (442 mg, 2.6 mmol) in H₂O (g mL) was purged with N₂ for 10 min followed by addition of pyridine (0.08 mL, 1.0 mmol) in ether (4 mL). To this now vigorously stirred mixture was added a solution of allyl (4R,5S,6S)-6-[1'(R)-hydroxyethyl]-4-methyl-3-[(tetrahydropyran-2-yl)thio]-7-oxo-1-azabicyclo[3.2.0]hept-2-ene-2-carboxylate (190 mg, 0.52 mmol) in ether (3 mL), and stirring was continued for 30 more min in the dark. The precipitate was collected by filtration, washed with water (10 mL), ether (2×10 mL), and dried to give the title material (186 mg, 92%) as a brown solid.

IR (Nujol) $\nu_{max}$: 3700-3200 (OH), 1760 and 1670 cm$^{-1}$ (C=O).

EXAMPLE 3 p-Nitrobenzyl (5R,6S)-6-[1'(R)-hydroxyethyl]-3-silver mercapto-7-oxo-1-azabicyclo3.2.0hept-2-ene-2-carboxylate

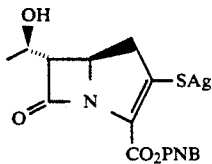

Step A p-Nitrobenzyl (5R,6S)-6-[1'(R)-hydroxyethyl]-3-[(triphenylmethyl)thio]-7-oxo-1-azabicyclo[3.2.0]hept-2-ene-2-carboxylate

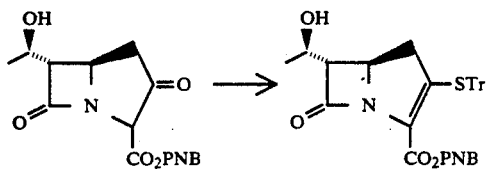

A cold (ice bath) solution of p-nitrobenzyl (2R, R,6S)-6-[(1'R)-1'-hydroxyethyl]-3,7-dioxo-1-azabicyclo[3.2.0]heptane-2-carboxylate (3.48 g, 10 mmol) in CH₃CN (40 mL) was first treated with ClPO(Oφ)₂ (2.33 mL, 11.0 mmol) and then with DIPEA (1.96 mL, 11 mmol) and stirred for 1 hour. To the resulting enol phosphate solution was added TrSH (8.3 g, 30 mmol) followed by DIPEA (5.3 mL, 30 mmol) dropwise. The resulting mixture was stirred for 21 h at c.a. 22° C., diluted with EtOAc (300 mL), washed with H₂O (4×200 mL), brine, and dried (MgSO₄) The residue was then passed through a pad of silica gel (125 g of silica gel, eluted with CH₂Cl₂ to EtOAc) to give the title material (4.87 g, 80%).

IR (CH ) $\nu$max: 3600 (OH), 1770, 1720 (C=O) and 1520 cm$^{-1}$ (NO₂);

¹H NMR (CDCl₃, 80 MHz) δ: 8.28-8.0 (2 (2H, m, PNB-H), 7.77-7.51 (2H, m, PNB-H), 7.46-7.23 (15H, m, aromatic H), 5.63, 5.45, 5.29, 5.11 (2H, ABq, J=14 Hz, CH₂PNB), 4-3.5 (2H, m, H-1' and H-5), 2.84 (1H, dd, J=2.5 Hz, J=7.0 Hz, H-6), 2.71, 2.59, 2.48, 2.36, 2.19, 2.07, 1.96, 1.84 (2H, m, CH₂), 1.5 (1H, bs, OH), 1.25 ppm (3H, d, J =6.3 Hz, CH₃).

Step B p-Nitrobenzyl (5R,6S)-6-[1'(R)-hydroxyethyl]-3-silver mercapto-7-oxo-1-azabicyclo[3.2.0]hept-2-ene-2-carboxylate

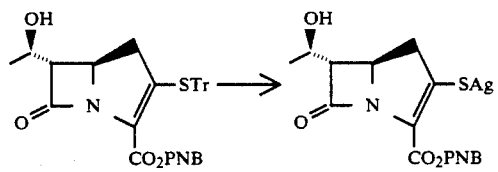

A cold (ice bath) solution of p-nitrobenzyl (5R, 6S)-6-[1'(R)-hydroxyethyl]-3-[(triphenylmethyl)thio]-7-oxo-1-azabicyclo[3.2.0]hept-2-ene-2-carboxylate (225 mg, 0.37 mmol) in CH₃CN (1 mL) was treated with a 0.15M solution of AgNO₃ in MeOH (2.7 mL, 0.41 mmol) and pyridine (34 μl, 0.41 mmol) and then stirred for 25 min. The mixture was diluted with ice cold H₂O (5 mL), and the precipitate was removed by filtration. The solid was washed with H₂O (1×5 mL), ether (4×10 mL) and dried under high vacuum for 18 h to give the title material (155 mg, 89%) as a yellow solid.

IR (Nujol) $\nu_{max}$: 3600-3200 (OH), 1775, 1670 (C=O) and 1520 cm$^{-1}$ (NO₂).

EXAMPLE 4

Potassium or sodium (5R,6S)-6-[1'(R)-hydroxyethyl]-3-(methylthio)methyl]-thio]-7-oxo-1-azabicyclo3.2.0hept-2-ene-2-carboxylate (Ia)

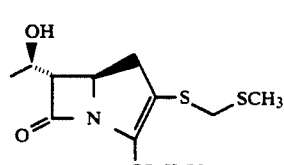

Step A p-Nitrobenzyl (5R,6S)-6-[1'(R)-hydroxyethyl]-3-[[(methylthio)methyl]thio]-7-oxo-1-azabicyclo[3.2.0]hept-2-ene-2-carboxylate

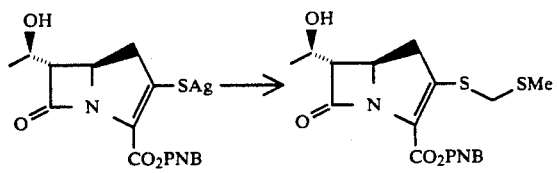

An acetonitrile (10 mL) solution of p-nitrobenzyl (5R,6S)-6-[1'(R)-hydroxyethyl]-3-silver mercapto-7-oxo-1-azabicyclo[3.2.0]hept-2-ene-2-carboxylate (422 mg, 0.900 mmol) was treated with ClCH₂SCH₃ (87 μl, 0.99 mmol) and stirred for 3 h. The mixture was then concentrated under vacuum and passed through a silica gel flash column (20 g of silica, eluted with CH₃CN) to give the title material (140 mg, 37%).

IR (CH₂Cl₂) $\nu_{max}$: 3680, 3600–3400 (OH), 1780, 1700 (C=O) and 1525 cm⁻¹ (NO₂);

¹H NMR (CDCl₃, 200 MHz) δ: 8.22–8.18 (2H, bd, J=8.7 Hz, PNB-H), 7.65, 7.61 (2H, bd, J=8.7 Hz, PNB-H), 5.53, 5.46, 5.26, 5.19 (2H, ABq, J=13.9 Hz, CH₂PNB), 4.3–4.1 (2H, m, H-1' and H-5), 3.93, 3.855, 3.846, 3.776 (2H, ABq, J=14.0 Hz, SCH₂S), 3.52, 3.47, 3.43, 3.38, 3.28, 3.24, 3.20, 3.15 (2H, m, CH₂-4), 3.21 (1H, dd, J=2.4 Hz, J=6.7 Hz, H-6), 2.22 (3H, s, SCH₃), 1.67 (1H, bd, J=4.8 Hz, OH), 1.35 ppm (3H, d, J=6.2 Hz, CH₃).

Step B

Potassium or Sodium (5R,6S)-6-[1'(R)-hydroxyethyl]-3-[[(methylthio)methyl]thio]-7-oxo-1-azabicyclo[3.2.0]hept-2-ene-2-carboxylate (Ia)

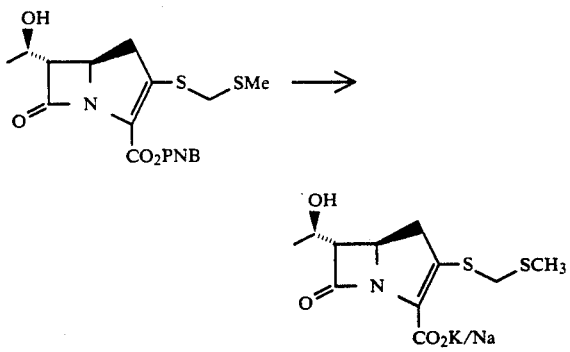

A solution of p-nitrobenzyl (5R,6S)-6-1'(R)-hydroxyethyl]-3-[[(methylthio)methyl]thio]-7-oxo-1-azabicyclo[3.2.0]hept-2-ene-2-carboxylate (300 mg, 0.700 mmol) in THF (25 mL), ether (25 mL) and a 0.05M pH 7.0 NaH₂PO₄/NaOH or KH₂PO₄/KOH buffer solution (25 mL) was subjected to hydrogenolysis at 45 psi H₂ for 1 h at 15° C. to 20° C. using 10% Pd/C as catalyst. The catalyst was removed by filtration and washed with H₂O (5 mL). The organic layer was extracted with the pH 7.0 buffer (2×5 mL). The aqueous fractions were combined, washed with ether (2×20 mL) and passed through reversed phase C₁₈ μBondaPak column (30 g of the reversed phase C₁₈ μBondaPak column material, first eluted with H₂O and then with 2% CH₃CN/H₂O) to give the title material (180 mg, 78%), as an off-white solid.

UV $\lambda^{H2O}_{max}$ 302 (8,900);

$T_{\frac{1}{2}} = 20$ h (pH 7.4);

IR (Nujol) $\nu_{max}$: 3600–3200 (OH), 1750 and 1590 cm⁻¹ (C=O);

¹H NMR (D₂O, 200 MHz) δ: 4.3–4.17 (2H, m, H-1' and H-5), 4.05, 3.98, 3.94, 3.87 (2H, ABq, J=13.7 Hz, SCH₂S), 3.46, 3.40, 3.37, 3.33, 3.27, 3.23, 3.19, 3.14 (2H, m, CH₂-4), 3.42 (1H, dd, J=2.6 Hz, J=5.9 Hz, H-6), 2.23 (3H, s, SCH₃), 1.29 ppm (3H, d, J=6.4 Hz, CH₃).

EXAMPLE 5

Sodium or Potassium (4R,5S,6S)-6-[1'(R)-hydroxyethyl-4-methyl-3-[[(methylthio)methyl]thio]-7-oxo-1-azabicyclo[3.2.0]hept-2-ene-2-carboxylate (Ib)

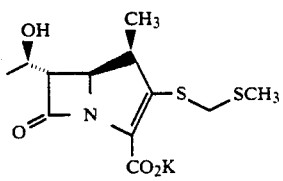

Step A p-Nitrobenzyl (4R,5S,6S)-6-[1'(R)-hydroxyethyl)-4-methyl-3-[[(methylthio)methyl]thio]-7-oxo-1-azabicyclo-[3.2.0]hept-2-ene-2-carboxylate

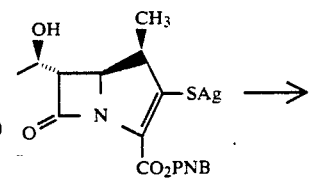

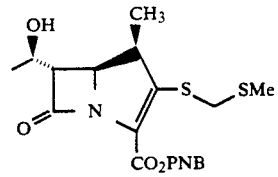

A cold (ice bath) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (4.85 g, 10.0 mmol) in DMF (40 mL) was slowly treated with a solution of iodomethyl methyl sulfide (1.04 mL, 12.5 mmol) in DMF (5 mL) and LiI (2.0 g, 15 mmol). The mixture was stirred for 1 h at 5° C., diluted with ice water (100 mL) and cold EtOAc (100 mL) and filtered through a pad of Celite. The pad was washed with EtOAc (4×100 mL) and the two solution phases were separated. The aqueous phase was then extracted with EtOAc (2×50 mL). The organic phases were combined, successively washed with cold water (2×150 mL), cold 0.1N aqueous HCl (150 mL), water (150 mL), 0.1M aqueous NaHCO₃ (150 mL), water (150 mL) and brine and dried (MgSO₄). The residue was loaded onto a pad of silica gel (35 g) and successively eluted with the following solvents, chilled at 0° C.: first with CH₂Cl₂ followed by 5, 10% and 20% EtOAC/CH₂Cl₂. After this purification step, 2.4 g (55%) of the title material was obtained.

IR (CH $\nu_{max}$: 3680–3600 (OH), 1775, 1710 (C=O) and 1520 cm⁻¹ (NO₂);

¹H NMR (CDCl₃, 200 MHz) δ: 8.23–8.18 (2H, m, PNB-H), 7.67, 7.62 (2H, bd, J=7.7 Hz, PNB-H), 5.54, 5.47, 5.23, 5.18 (2H, ABq, J=12.8 Hz, CH₂), 4.26 (1H, dd, J=2.6 Hz, J=9.2 Hz, H-5) 4.32–4.19 (1H, m, H-1'), 4.02, 3.95, 3.78, 3.71 (2H, ABq, J=13.7 Hz, CH₂), 3.63–3.47 (1H, m, H-4), 3.26 (1H, dd, J=2.6 Hz, J=7.8 Hz, H-6), 2.21 (3H, s, CH₃), 1.357 (3H, d, J=6.3 Hz, CH₃), 1.26 ppm (3H, d, J=7.3 Hz, CH₃).

Step B

Sodium (4R,5S,6S)-6-[1'(R)-hydroxyethyl]-4-methyl-3-[[(methylthio)methyl]thio]-7-oxo-1-azabicyclo[3.2.0]hept-2-ene-2-carboxylate (Ib')

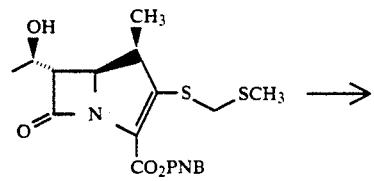

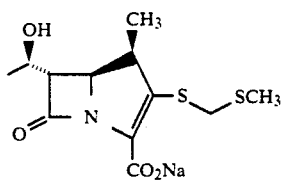

A solution of p-nitrobenzyl (4R,5S,6S)-6-[1'(R)-hydroxyethyl]-4-methyl-3-[[(methylthio)methyl]thio]-7-oxo-1-azabicyclo[3.2.0]-hept-2-ene-2-carboxylate (6.00 g, 13.7 mmol) in THF (70 mL), ether (70 mL) and a 0.1M NaH₂PO₄/NaOH pH 7.0 buffer solution (255 mL, 25.5 mmol) was subjected to hydrogenolysis over 10% Pd/C catalyst (6 g) at 45–50 psi for 3.5 h at room temperature (c.a. 22° C.). The catalyst was removed by filtration and washed with the 0.1M phosphate pH 7.0 buffer solution (2×15 mL). The two solution phases were separated and the organic layer was extracted with the pH 7.0 buffer solution (2×15 mL). The aqueous layers were combined, washed with ether (3×100 mL) and passed through a partisil reversed phase column (275 g of the partisil reversed phase material, first eluted with H₂O followed by 10% CH₃CN/H₂0) to give the title material (3.37 g, 76%) as a white solid.

UV $\lambda^{H2O}_{max}$ 304 (10208);

IR (Nujol) $\nu_{max}$: 1740 and 1580 cm⁻¹ (C=O);

¹H NMR (D₂O, 200 MHz) δ: 4.32–4.19 (1H, m, H-1'), 4.22 (1H, dd, J=2.5 Hz, J=9.2 Hz, H-5), 4.11, 4.04, 3.87, 3.81 (2H, ABq, J=13.7 Hz, SCH₂S), 3.6–3.48 (1H, m, H-4), 3.44 (1H, dd, J=2.6 Hz, J=6.2 Hz, H-6), 2.22 (3H, s, CH₃), 1.30 (3H, d, J=6.4 Hz, CH₃) and 1.21 ppm (3H, d, J=7.3 Hz, CH₃).

Step A

Allyl (4R,5S,6S)-6-[1'(R)-hydroxyethyl]-4-methyl-3-[[(methylthio)methyl]thio]-7-oxo-1-azabicyclo[3.2.0]hept-2-ene-2-carboxylate

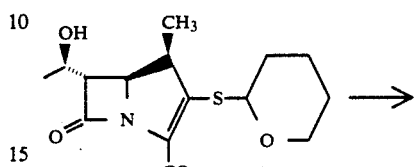

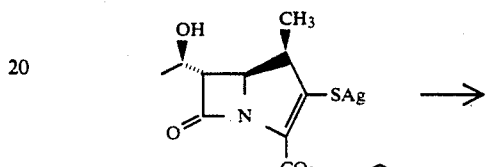

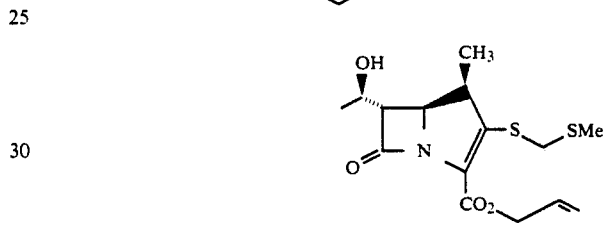

A cold (ice-MeOH bath) solution of allyl (4R,5S 6S)-6-[1'(R)-hydroxyethyl]-4-methyl-3-[(tetrahydropyran-2-yl)-thio]-7-oxo-1-azabicyclo[3.2.0]hept-2-ene-2-carboxylate (104 mg, 0.280 mmol) in MeOH (1 mL) was treated dropwise with a solution of AgNO₃ (145 mg, 0.85 mmol) in MeOH (3 mL) and pyridine (0.045 mL, 0.560 mmol) and stirred for 5 min at −15° C. Ether (15 mL) was added in order to precipitate the silver salt formed. The solvent was decanted and the solid was triturated with ether (2×10 mL). The silver salt was then dried under vacuum and taken up in CH₃CN (2 mL). The acetonitrile solution was cooled to −20° C. (ice-MeOH bath) and treated with ClCH₂SCH₃ (0 10 mL, 1.2 mmol). The resulting mixture was stirred for 1 h at −15° C. to 0° C., passed through a pad of silica gel (2.5 g of silica, eluted with EtOAc) and concentrated to give a residue that was applied on preparative TLC plates (eluted with CH₂Cl₂/EtOAc:1/1). The title material was isolated in low yield as an oil.

IR (neat) $\nu_{max}$: 3600–3300 (OH), 1770 and 1710 cm⁻¹ (C=O);

¹H NMR (CDCl₃, 200 MHz) δ: 6.02–5.84 (1H, m, vinylic-H), 5.47–5.20 (2H, m, vinylic-H), 487–4.61 (2H, m, CH₂-vinyl), 4.3–4.15 (1H, m, H-1'), 4.21 (1H, dd, J=2.4 Hz, J=8.8 Hz, H-5), 3.99, 3.92, 3.76, 3.69 (2H, ABq, J=13.7 Hz, SCH₂S), 3.6–3.4 (1H, m, H-4), 3.225 (1H, dd, J=2.4 Hz, J=6.9 Hz, H-6), 2.21 (3H, s, SCH₃), 1.335 (3H, d, J=6.2 Hz, CH₃), 1.24 ppm (3H, d, J=7.3 Hz, CH₃).

Step B

Potassium (4R,5S,6S)-6-[1'(R)-hydroxyethyl]-4-methyl-3-[[(methylthio)methyl]thio]-7-oxo-1-azabicyclo[3.2.0]hept-2-ene-2-carboxylate (Ib'')

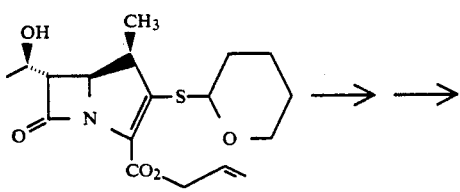

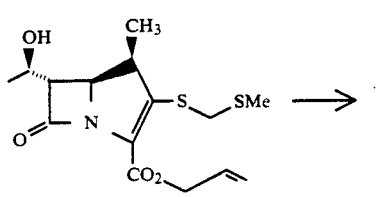

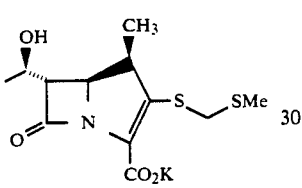

The silver salt obtained from allyl (4R,5S,6S)-6-[1'(R)-hydroxyethyl]-4-methyl-3-(tetrahydropyran-2-yl)thio]-7-oxo-1-azabicyclo[3.2.0]-hept-2-ene-2-carboxylate (2.0 g, 5.45 mmol) was treated as described above with ClCH$_2$SCH$_3$ to give the allyl (4R,5S,6S)-6-[1'(R)-hydroxyethyl]-4-methyl-3-[[(methylthio)methyl]thio]-7-oxo-1-azabicyclo[3.2.0]hept-2-ene-2-carboxylate which without isolation was cooled to 5° C. (ice bath) and treated with Pd(Pφ$_3$)$_4$ (381 mg, 0.33 mmol), Pφ$_3$ (372 mg, 1.42 mmol) and a solution of potassium ethylhexanoate (3.6 g, 19 mmol) in EtOAc (20 mL). The precipitate formed was redissolved by adding CH$_3$CN (20 mL) and the solution was continued to be stirred for 2 h at room temperature (c.a. 22° C.). The mixture was dissolved with ether (50 mL) and extracted with a 0.05M pH 7.4 phosphate buffer solution (3×10 mL). The basic aqueous extracts were washed with ether (2×25 mL) and passed through a reversed phase C$_{18}$ column (80 g of the reversed phase material; the column eluted first with H$_2$O followed by 2%, 5% and 10% CH$_3$CN/H$_2$O) to give the impure title material. The material was lyophilized and the resulting powder was repurified on a C$_{18}$ reversed phase column (50 g of the C$_{18}$ material; the column eluted first with H$_2$O and then successively with 2% and 5% CH$_3$CN/H$_2$O) to give the pure title material (135 mg, 7%) whose physical data were identical to the sodium salt described above; Purity: 99.94% (HPLC), T$_{\frac{1}{2}}$75 h (pH 7.4); T$_{\frac{1}{2}}$18.8 mn (pH 2).

EXAMPLE 6

Potassium or sodium (5R,6S)-6-1'(R)-hydroxyethyl]-3-[[(pyridin-4-yl)thio]methyl]thio]-7-oxo-1-azabicyclo-3.2.0]hept-2-ene-2-carboxylate (Ic)

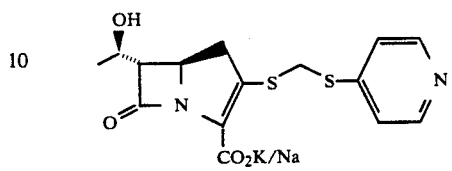

Step A p-Nitrobenzyl (5R,6S)-6-[1'(R)-hydroxyethyl]-3-[[[(pyridin-4-yl)thio]methyl]thio]-7-oxo-1-azabicyclo[3.2.0]hept-2-ene-2-carboxylate

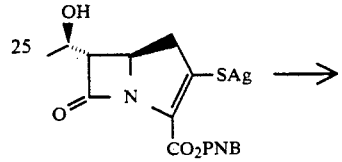

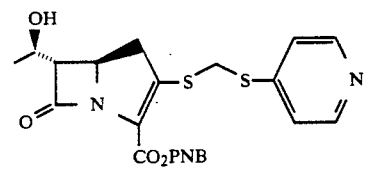

A cold (ice bath) suspension of p-nitrobenzyl (5R,6S)-6-[1'(R)-hydroxyethyl]-3-silver mercapto-7-oxo-1-azabicyclo[3.2.0]hept-2-ene-2-carboxylate (2.5 g, 5.3 mmol) in DMF (20 mL) was treated dropwise with 4-[(chloromethyl)thio]pyridine (1.00 g, 6.36 mmol) in DMF (5 mL) followed by the addition of LiI (1.42 g, 10.6 mmol) and DIPEA (1.1 mL, 6.36 mmol). The mixture was stirred for 24 h at c.a. 22° C., then diluted with H$_2$O (25 mL) and EtOAc, and filtered. The two solution phases were separated, and the aqueous layer was extracted with EtOAc (2×40 mL). The organic phases were combined, washed with ice cold H$_2$O (5×50 mL) and brine (50 mL) and dried (MgSO$_4$) The solid residue recovered after evaporation of the solvent was triturated with a cold (5° C.) 1/1 mixture of CH$_2$Cl$_2$-ether (25 mL) to give the title material as a solid which was washed with the same solvent mixture (2×10 mL) and dried (1.47 g). The oily residue obtained upon evaporation of the mother liquor was applied on preparative TLC plates (eluted with EtOAc/CH$_3$CN:9/1), also to give the title material (total yield 1.56 g, 60%).

IR (CH$_2$Cl$_2$) ν$_{max}$: 3600–3100 (OH), 1800, 1690 (C=O), and 1520 cm$^{-1}$ (NO$_2$);

1H NMR (DMSO, 200 MHz) δ: 8.43–8.39 (2H, m, pyridine-H$_2$ and H-6), 8.22–8.14 (2H, m, PNB-H), 7.67–7.63 (2H, d, J=8.8 Hz, PNB-H), 7.38–7.34 (2H, m, pyridine-H$_3$ and H-5), 5.44, 5.37, 5.28, 5.21 (2H, ABq, J=14.1 Hz, CH$_2$-PNB), 5.085 (1H, d, J=5.0 Hz, OH), 4.72 (2H, SCH$_2$S), 4.18 (1H, dt, J=2.7 Hz, J=9.8 Hz, H-5), 3.99–3.85 (1H, m, H-1'), 3.48–3.3 (2H, m, CH$_2$-4), 3.35 (1H, dd, J=2.8 Hz, J=6.1 Hz, H-6), 1.12 ppm (3H, d, J=6.3 Hz, CH₃)

Step B

Potassium or sodium (5R,6S)-6-[1'(R)-hydroxyethyl]-3-[[[(pyridin-4-yl)thio]-methyl]thio]-7-oxo-1-azabicyclo[3.2.0]hept-2-ene-2-carboxylate (Ic)

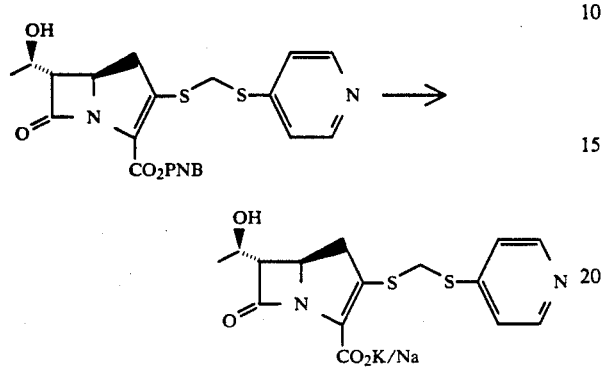

A solution of p-nitrobenzyl (5R,6S)-6-[1'(R)-hydroxyethyl]-3-[[[(pyridin-4-yl)thio]methyl]thio]-7-oxo-1-azabicyclo[3.2.0]hept-2-ene-2-carboxylate (750 mg, 1.54 mmol) in THF (40 mL), ether (40 mL), and a 0.05M pH 7.0 NaH₂PO₄/NaOH or KH₂PO₄/KOH buffer solution (40 mL, 2.0 mmol) was subjected to hydrogenolysis for 1 h at 40 psi H₂ using 10% Pd/C (750 mg) as catalyst. The catalyst was removed and washed with H₂O (5 mL). The filtrate was diluted with ether (50 mL), and the organic phase was extracted with H₂O (2×5 mL). The aqueous phases were combined, washed with ether (2×50 mL), and passed through a C₁₈ μBondaPak reversed phase column (40 g of the reversed phase; eluted first with H₂O and then successively with 5%, 10% and 15% CH₃CN/H₂O) to give the title material (217 mg, 37%); purity 97.9% (as checked by HPLC); T₁15 h (pH 7.4).

UV $\lambda^{H_2O}_{max}$ 300 (13250), 270 (12,000);

IR (Nujol) $\nu_{max}$: 3600–3200 (OH), 1750 and 1690 cm⁻¹ (C=O);

¹H NMR (D₂O, 200 MHz) δ: 8.37–8.33 (2H, m, pyridine H-2 and H-6), 7.41–7.38 (2H, m, pyridine H-3 and H-5), 4.55, 4.481, 4.477, 4.41 (2H, ABq, J=14.1 Hz, SCH₂S), 4.29–4.16 (1H, m, H-1'), 4.20 (1H, dt, J=2.5 Hz, J=6.7 Hz, H-5), 3.40 (1H, dd, J=2.5 Hz, J=8.0 Hz, H-6), 3.46, 3.38, 3.33, 3.29, 3.25, 3.21, 3.17 (2H, m, CH₂-4), 1.28 ppm (3H, d, J=6.4 Hz, CH₃).

EXAMPLE 7

Potassium or sodium (4R,5S,6S)-6-[1'(R)-hydroxyethyl]-4-methyl[[(phenylthio)methyl]thio]-7-oxo-1-azabicyclo[3.2.0]hept-2-ene-2-carboxylate (Id)

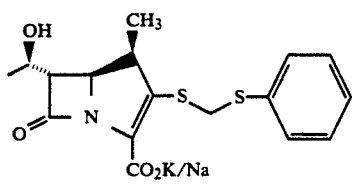

Step A p-Nitrobenzyl (4R,5S,6S)-6-[1'(R)-hydroxyethyl]-4-methyl-3-[[(phenylthio)methyl]thio]-7-oxo-1-azabicyclo[3.2.0]hept-2-ene-2-carboxylate A cold (ice bath) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (760 mg, 1.57 mmol) in CH₃CN (25 mL) was treated with chloromethylphenyl sulfide (0.255 mL, 1.9 mmol) and the mixture was stirred for 30 min. Addition of chloromethylphenyl sulfide (0.5 mL, 3.8 mmol) was repeated twice followed by stirring periods of 30 and 45 min, respectively. The cold mixture was passed through a pad of silica gel (5 g) and the pad was washed with cold EtOAc (20 mL). The filtrate was diluted with EtOAc (50 mL), washed with an ice cold 0.05M pH 7.4 aqueous phosphate buffer solution (2×50 mL), water (1×50 mL) and brine (50 mL), dried (MgSO₄) and concentrated. The residue was passed through a silica gel (25 g) column by eluting successively with hexane, CH₂Cl₂/hexane (1/1), CH₂Cl₂, 10% EtOAc/CH₂Cl₂ and 25% EtOAc/CH₂Cl₂ to give the title material (300 mg, 38%).

IR (CH₂Cl₂) $\nu_{max}$: 3600 (OH), 1775, 1710 (C=O) and 1525 cm⁻¹ (NO₂);

1H NMR (CDCl₃, 200 MHz) δ: 8.15–8.11 (2H, m, PNB-H), 7.57, 7.53 (2H, bd, J=8.7 Hz, PNB-H), 7.39–7.18 (5H, m, aromatic-H), 5.46, 5.39, 5.18, 5.11 (2H, ABq, J=14.8 Hz, CH₂), 4.24, 4.17, 4.11, 4.05 (2H, ABq, J=13.4 Hz, SCH₂S), 4.24–4.11 (2H, hidden H-1' and H-5), 4.00–3.32 (1H, m, H-4), 3.195 (1H, dd, J=2.6 Hz, J=6.8 Hz, H-6), 1.64–1.62 (1H, bd, J=4.5 Hz, OH), 1.297 (3H, d, J=6.2 Hz, CH₃), 1.17 ppm (3H, d, J=7.3 Hz, CH₃).

Step B

Potassium or sodium (4R,5S,6S)-6-[1'(R)-hydroxyethyl]-4-methyl-3-[[(phenylthio)methyl]thio]-7-oxo-1-azabicyclo[3.2.0-]hept-2-ene-2-carboxylate (Id)

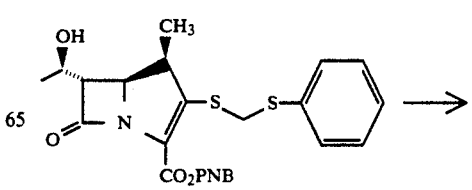

-continued

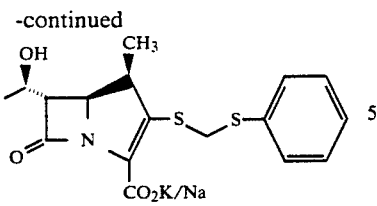

A solution of p-nitrobenzyl (4R,5S,6S)-6-[1'(R)hydroxyethyl]-4-methyl-3-[[(phenylthio) methyl]thio]-7-oxo-1-azabicyclo[3.2.2]hept-2-ene-2-carboxylate (230 mg, 0.46 mmol) in THF (10 mL), ether (10 Ml) and a 0.05M pH 7.0 phosphate buffer solution (10 mL) was subjected to hydrogenolysis over 10% Pd/C catalyst (230 mg) for 1 h at 40 psi $H_2$. The catalyst was filtered off. The organic phase was separated and subjected to further hydrogenolysis for 1 h at 40 psi using the pH 7.0 buffer solution (10 mL) over the 10% Pd/C catalyst (230 mg). The same process was repeated and at the end of the hydrogenolysis the three aqueous phases were combined, washed with ether (2×10 mL) and passed through a $C_{18}$ μBondaPak reversed phase column (23 g of the packing material; the column eluted first with H20 followed successively by 5%, 10% and 20% $CH_3CN/H_2O$) to give the title material (120 mg, 66%); $T_{\frac{1}{2}}=100$ h (pH 7.4), $T_{\frac{1}{2}}=18.8$ min (pH2); purity: 99.9% (as checked by HpLC).

UV $\lambda^{H2O}_{max}$: 306 (10,050), 254 (6440);

IR (Nujol) $\nu_{max}$: 3600-3200 (OH), 1755 and 1600 $cm^{-1}$ (C=O);

$^1$H NMR ($D_2O$, 200 MHz) δ: 7.63, 7.36 (5H, m, aromatic H), 4.45, 4.38, 4.22, 4.15 (2H, ABq, J=14.0 Hz, $SCH_2S$), 4.27-4.15 (1H, m, H-1'), 3.915 (1H, dd, J=2.5 Hz, J=9.2 Hz, H-5), 3.360 (1H, dd, J=2.5 Hz, J=6.1 Hz, H-6), 3.34-3.17 (1H, m, H-4), 1.27 (3H, d, J=6.4 Hz, $CH_3$), 1.108 ppm (3H, d, J=7.3 Hz, $CH_3$).

EXAMPLE 8

Sodium (5R,6S)-6-[1'(R)-hydroxyethyl]-3-[[[(pyridin-2-yl)thio]-methyl]thio]-7-oxo-1-azabicyclo[3.2.0]hept-2-ene-2-carboxylate (Ie)

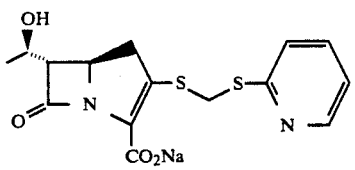

Step A p-Nitrobenzyl (5R,6S)-[1'(R)-hydroxyethyl]-3-[[[(pyridin-2-yl)thio]-methyl]thio]-7-oxo-1-azabicyclo[3.2.0]hept-2-ene-2-carboxylate

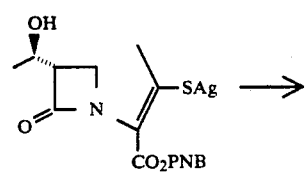

-continued

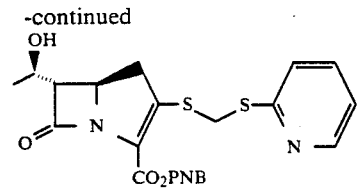

A cold (ice bath) solution of p-nitrobenzyl (5R,6S)-6-[1'(R)-hydroxyethyl]-3-silver mercapto-7-oxo-1-azabicyclo[3.2.0]hept-2-ene-2-carboxylate (235 mg, 0.500 mmol) in DMF (2 mL) was treated with a solution of 2-[(chloromethyl)thio]pyridine (96 mg, 0.60 mmol) in DMF (0.5 mL) followed by addition of LiI (134 mg, 1.00 mmol) and DIPEA (0.10 mL, 0.60 mmol). The mixture was stirred at room temperature c.a. 22° C. for 25 h, diluted with ice cold $H_2O$ (2.5 mL) and EtOAc (2.5 mL) and filtered. The filtrate was diluted with $H_2O$ (5 mL) and EtOAc (5 mL) and the aqueous layer was extracted EtOAc (4×10 mL). The organic layers (extracts) were combined, washed with cold $H_2O$ (5×10 mL) and brine (1×10 mL) and dried ($MgSO_4$). The residue was triturated with $CCl_4$ to give a dark beige solid that was purified on preparative TLC plates (eluted with $EtOAc/CH_2Cl_2$:1/1) to give the title material (160 mg, 66%).

IR (CH ) $\nu_{max}$: 3600 (OH), 1780, 1700 (C=O) and 1525 $cm^{-1}$ ($NO_2$);

1H NMR ($CDCl_3$, 200 MHz) δ: 8.47-8.44 (1H, m, pyridine-H), 8.21-8.17 (2H, d, J=9.8 Hz, PNB-H), 7.64-7.60 (2H, d, J=9.8 Hz, PNB-H), 7.58-7.49 (1H, m, pyridine H), 7.20-7.16 (1H, bd, J=8.1 Hz, pyridine-H), 7.09-7.03 (1H, m, pyridine-H), 5.51, 5.45, 5.25, 5.18 (2H, ABq, J=13.8 Hz, $CH_2$-PNB), 4.69, 4.62, 4.55 (2H, ABq, J=14 Hz, $SCH_2S$), 4.4-4.15 (2H, m, H-1' and H-5), 3.59, 3.54,3.50, 3.45, 3.37, 3.32, 3.28, 3.23 (2H, m, $CH_2$), 3.24 (1H, dd, J=2.7 Hz, J=6.8 Hz, H-6), 1.74 (1H, d, J=4.8 Hz, OH), 1.375 ppm (3H, d, J=6.3 Hz, $CH_3$).

Step B

Sodium (5R,6S)-6-[1'(R)-1-hydroxyethyl]-3-[[[(pyridin-2-yl)thio]methyl]thio]-7-oxo-1-azabicyclo[3.2.0]hept-2-ene-2-carboxylate (Ie)

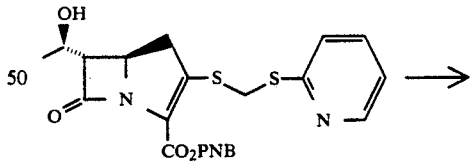

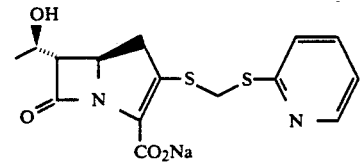

A solution of p-nitrobenzyl (5R,6S)-6-[1'(R)-hydroxyethyl]-3-[[[(pyridin-2-yl)thio)methyl]thio]-7-oxo-1-azabicyclo[3.2.0]hept-2-ene-2-carboxylate (880 mg, 1.82 mmol) in THF (50 mL), ether (50 mL) and a 0.05M, pH 7.0 $NaH_2PO_4/NaOH$ buffer solution (80 mL, 4 mmol) was subjected to hydrogenolysis at 45 psi $H_2$ for 1 h at 15° C., using 10% Pd/C (880 mg) as catalyst. The catalyst was removed by filtration and washed with $H_2O$ (25 mL). The organic phase was extracted with $H_2O$ (2×20 mL). The aqueous phases were combined, washed with ether (2×25 mL) and passed through a $C_{18}$ μBondaPak reversed phase column (75 g of the packing material; the column eluted first with $H_2O$ followed successively by 2%, 5% and 8% $CH_3CN/H_2O$) to give the title material (320 mg, 47%); purity: 99.9% (as checked by HPLC); $T_{\frac{1}{2}}$19 h (pH 7.4).

UV $\lambda^{H_2O}_{max}$298 (16,100), 246 (9,950);

IR (Nujol) $\nu_{max}$:3600–3400 (OH); 1760 and 1595 $cm^{-1}$ (C=O);

$^1H$ NMR ($D_2O$, 200 MHz) δ: 8.46–8.42 (1H, m, pyridine-H), 7.81–7.73 (1H, m, pyridine-H), 7.50, 7.46 (1H, d, J=8.1 Hz, pyridine H), 7.32–7.25 (1H, m, pyridine H), 4.59, 4.52, 4.50, 4.43 (2H, ABq, J=13.9 Hz, $SCH_2S$), 4.25–4.12 (2H, m, H-1' and H-5), 3.39 (1H, dd, J=2.6 Hz, J=5.9 Hz, H-6), 3.43, 3.38, 3.34, 3.29, 3.25, 3.21, 3.16, 3.12 (2H, m, $CH_2$-4), 1.285 ppm (3H, d, J=6.4 Hz, $CH_3$).

EXAMPLE 9

Sodium (4R,5S,6S)-6-[1'(R)-hydroxyethyl]-4-methyl-3-[[[(pyridin-2-yl)thio]methyl]thio]-7-oxo-1-azabicyclo[3.2.0-]hept-2-ene-2-carboxylate (If)

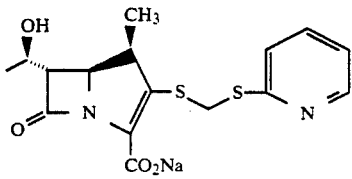

Step A p-Nitrobenzyl (4R,5S,6S)-6-[1'(R)-hydroxyethyl]-4-methyl-3-[[[(pyridin-2-yl)thio]methyl]thio]-7-oxo-1-azabicyclo[3.2.0-]hept-2-ene-2-carboxylate

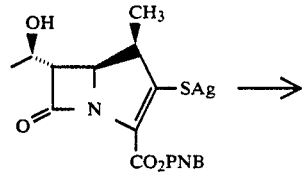

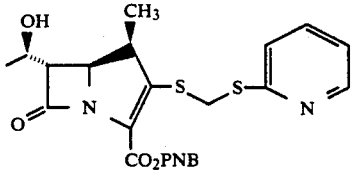

A solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (788 mg, 1.62 mmol) in DMF (7 mL) was treated at 5° C. (ice bath) with 2-[(chloromethyl)thio]pyridine (311 mg, 1.95 mmol) in DMF (1 mL) followed by addition of LiI (434 mg, 3.24 mmol) and DIPEA (0.32 mL, 1.95 mmol). The mixture was stirred for 24 h at c.a. 22° C., diluted with ethyl acetate (25 mL) and ice cold $H_2O$ (25 mL). The salts were removed by filtration and washed with EtOAc (10 mL). The two solution phases were separated and the aqueous layer was extracted ethyl acetate (3×10 mL). The organic extracts were combined, washed with ice cold $H_2O$ (5×20 mL) and brine (1×20 mL) and dried ($MgSO_4$) The residue was passed through a silica gel (15 g) column (first eluted with $CH_2Cl_2$ followed successively by 5%, 10%, 15% and 25% $EtOAc/CH_2Cl_2$) to give the title material which was repurified on preparative TLC plates (eluted with $CH_2Cl_2/EtOAc$: 1/1) to afford 440 mg (54%) of the pure product.

IR ($CH_2Cl_2$) $\nu_{max}$: 3600 (OH), 1775, 1710 $cm^{-1}$ (C=O) and 1525 $cm^{-1}$ ($NO_2$);

1H NMR ($CDCl_3$, 200 MHz) δ: 8.45–8.42 (1H, m, pyridine H-6), 8.19–8.13 (2H, m, PNB-H), 7.63, 7.58 (1H, d, J=8.7 Hz, PNB-H), 7.57–7.48 (1H, m, pyridine H), 7.19–7.15 (1H, d, J=8.1 Hz, pyridine H), 7.08–7.0–1 (1H, m, pyridine H), 5.51, 5.44, 5.72, 5.15 (2H, ABq, J=13.8 Hz, $CH_2$-PNB), 4.74, 4.68, 4.60, 4.54 (2H, ABq, J=13.2 Hz, $SCH_2S$), 4.25 (1H, dd, J=2.5 Hz, J=9.1 Hz, H-5), 4.3–4.2 (1H, hidden m, H-1'), 3.68–3.53 (1H, m, H-4), 3.28 (1H, dd, J=2.5 Hz, J=6.8 Hz, H-6), 1.37 (3H, d, J=6.2 Hz, $CH_3$), 1.34 ppm (3H, d, J=7.3 Hz, $CH_3$).

Step B

Sodium (4R,5S,6S)-6-[1'(R)-hydroxyethyl]-4-methyl-3-[[[(pyridin-2-yl)thio]methyl]thio]-7-oxo-1-azabicyclo[3.2.0-]hept-2-ene-2-carboxylate (If)

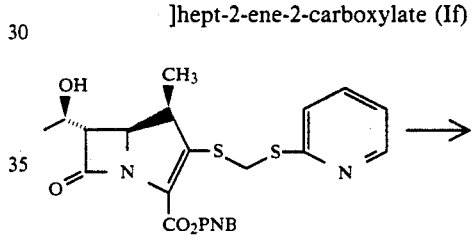

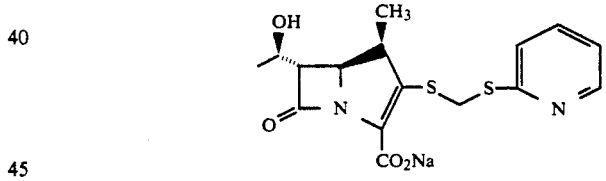

A solution of p-nitrobenzyl (4R,5S,6S)-6-[1'(R)-1-hydroxyethyl]-4-methyl-3-[[[(pyridin-2-yl)thio]methyl]thio]-7-oxo-1-azabicyclo[3.2.0]hept-2-ene-2-carboxylate (435 mg, 0.868 mmol) in THF (35 mL), ether (35 mL) and a pH 7.0 phosphate buffer (0.05M, 35 mL) solution was subjected to hydrogenolysis at 45 psi $H_2$ for 1 h at 15° C. to 22° C. using 10% Pd/C (435 mg) as catalyst. The mixture was diluted with ether (20 mL), and the catalyst was removed by filtration and washed with $H_2O$ (10 mL). The two solution phases were separated and the ether layer was extracted with $H_2O$ (2×5 mL). The aqueous layers were combined, washed with ether (3×20 mL) and passed through a $C_{18}$μBondaPak reversed phase column (30 g of the $C_{18}$μBondaPak reversed phase material; the column first eluted with $H_2O$ followed successively by 2%, 5%, 8% and 10% $CH_3CN/H_2O$) to give the title material contaminated with charcoal. The product was lyophilized and the resulting powder was taken up in $H_2O$ and passed again through a small pad of reversed phase $C_{18}$μBondaPak (5 g of the reversed phase $C_{18}$μBondaPak material; first eluted with $H_2O$ followed successively by 2%, 5% and 10% CH₃CN/H₂O) to give the pure title material (85 mg, 25%); T$_{\frac{1}{2}}$: 79 h (pH 7.4); T$_{\frac{1}{2}}$: 36 min (pH 2); purity: 99.2% (as checked by HPLC at 298 nm).

U.V. $\lambda^{H2O}_{max}$ 298 (13,500), 246 (8990);

IR (Nujol) $\nu_{max}$: 3600-3200 (OH), 1750 and 1600 cm$^{-1}$ (C=O);

¹H NMR (D₂O, 200 MHz) δ: 8.48-8.39 (1H, m, pyridine H-6), 7.82-7.73 (1H, m, pyridine-H), 7.53, 7.49 (1H, d, J=8.0 Hz, pyridine H), 7.34-7.27 (1H, m, pyridine-H), 4.60, 4.53, 4.47, 4.40 (2H, ABq, J=13.9 Hz, SCH₂S), 4.30, 4.27, 4.24, 4.21, 4.17 (1H, 5 lines, H-1'), 4.10 (1H, dd, J=2.6 Hz, J=9.2 Hz, H-5), 3.51-3.36 (1H, m, H-4), 3.42 (1H, dd, J=2.6 Hz, J=6.4 Hz, H-6), 1.29 (3H, d, J=6.4 Hz, CH₃) and 1.19 ppm (3H, d, J=7.1 Hz, CH₃).

EXAMPLE 10

Potassium or sodium (4R,5S,6S)-6-[1'(R)-hydroxyethyl]-4-methyl-3-[[[(pyridin-4-yl)thio]methyl]thio]-7-oxo-1-azabicyclo[3.2.0-]hept-2-ene-2-carboxylate (Ig)

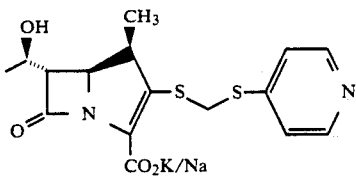

Step A

4[(Chloromethyl)thio]pyridine

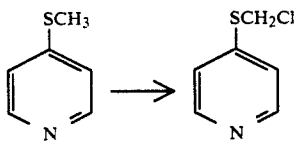

A solution of 4-methylthiopyridine (2.28 g, 18.2 mmol), N-chlorosuccinimide (3.0 g, 23 mmol) and pyridine (2.9 mL, 3.0 mmol) in benzene (40 mL) was heated at 50°-60° C. for 3 h. The mixture was allowed to cool to room temperature. The solvent was decanted and the residue was rinsed with benzene (2×10 mL). The organic phases were combined and evaporated. The residue was passed through a pad of silica gel (40 g) to give the title material (1.35 g) contaminated with the starting material. The impure product was repurified on silica gel preparative plates (eluted with CH₂Cl₂/CH₃CN: 1/1) to give the pure title material (926 mg, 32%) as a yellow oil.

IR (neat) $\nu_{max}$: 1570, 1540 cm$^{-1}$ (aromatic);

¹H NMR (CDCl₃, 80 MHz) δ: 8.55-8.47 (2H, m, aromatic-H 7.33-7.25 (2H, m, aromatic-H), 5.04 ppm (2H, s, CH₂).

Step B p-Nitrobenzyl (4R,5S,6S)-6-[1'(R)-hydroxyethyl]-4-methyl-3-[[[(pyridin-4-yl)thio]methyl]thio]-7-oxo-1-azabicyclo[3.2.0]-hept-2-ene-2-carboxylate

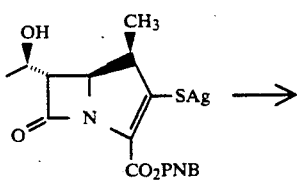

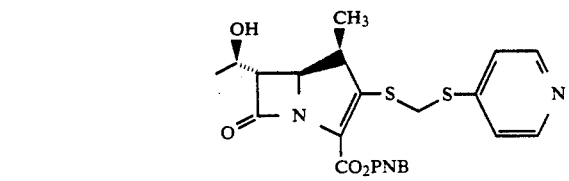

A solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (794 mg, 1.00 mmol), 4-[(chloromethyl)thio] pyridine (314 mg, 1.97 mmol), LiI (440 mg, 3.28 mmol) and DIPEA (0.345 mL, 2.0 mmol) in DMF (8 mL) was stirred for 20 h at c.a. 22° C. The mixture was diluted with ethyl acetate (10 mL) and water (5 mL) and filtered. The aqueous phase was extracted with ethyl acetate (2×5 mL). The organic extracts were combined, washed with cold H₂O (4×10 mL) and brine (1×10 mL),dried (MgSO₄) and concentrated. Purification of the residue on preparative TLC plate (eluted with 10% CH₃CN/EtOAc) afforded the title material (430 mg, 52%).

IR (CH₂Cl₂) $\nu_{max}$: 3600 (OH), 1775 and 1615 cm$^{-1}$ (C=O);

¹H NMR (CDCl₃, 200 MHz) δ: 8.48-8.44 (2H, m, H-2,6-pyridine), 8.23-8.18 (2H, m, PNB-H), 7.64-7.60 (2H, m, PNB-H), 7.19-7.15 (2H, m, H-3,5-pyridine), 5.51, 5.44, 5.24, 5.17 (2H, ABq, J=13.8 Hz, CH₂-PNB), 4.31 (2H, s, SCH₂S), 4.30-4.17 (1H, m, H-1'), 4.27, 4.26 (1H, part of dd, J=2.7 Hz, part of H₅), 3.6-3.4 (1H, m, H-4), 3.29 (1H, dd, J=2.7 Hz, J=6.8 Hz, H-6), 1.7 (1H, bd, OH), 1.366 (3H, d, J=6.3 Hz, CH₃), 1.29 ppm (3H, d, J=7.3 Hz, CH₃).

Step C

Potassium or sodium (4R,5S,6S)-6-[1'(R)-hydroxyethyl]-4-methyl-3-[[[(pyridin-4-yl)thio]methyl]thio]-7-oxo-1-azabicyclo[3.2.0-]hept-2-ene-2-carboxylate (Ig)

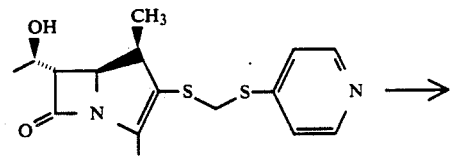

-continued

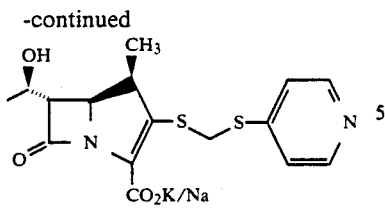

A solution of p-nitrobenzyl (4R,5S,6S)-6-1'(R)hydroxyethyl]-4-methyl-3-[[[(pyridin-4-yl)thio]methyl]-thio]-7-oxo-1-azabicyclo[3.2.0]hept-2-ene-2-carboxylate (663 mg, 1.32 mmol) in THF (30 mL), ether (30 mL) and a pH 7.0 NaH/NaOH or KH/KOH buffer solution (0.05M, 30 mL) was subjected to hydrogenolysis over 10% Pd/C catalyst (663 mg) for 1 h at 40 psi $H_2$. The mixture was diluted with ether (50 mL) and filtered. The catalyst was washed with the pH 7.0 buffer solution (0.05M, 5 mL) and water (5 mL). The aqueous layer was washed with ether (3×20 mL) and passed through a $C_{18}$ μ-Bondapak reversed phase column (55 g of the $C_{18}$ μ-Bondapak reversed phase material) to give 282 mg (54%) of the title compound as a yellow solid; $T_{\frac{1}{2}}=34$ min (pH 2); purity 99.9% as measured by HPLC (retention time, 9.63 min, 10% $CH_3CN$/pH 7 buffer).

UV $\lambda^{H2O}_{max}$ 300 (13,100), 270 (11,750);

IR (Nujol) $\nu_{max}$: 1750 and 1600 cm$^{-1}$;

$^1$H NMR ($D_2O$, 200 MHz) δ8.385-8.35 (2H, m, H-2, 6-pyridine), 7.45-7.41 (2H, m, H-3, 5-pyridine), 4.55, 4.48, 4.47, 4.40 (2H, ABq, J=13.8 Hz, $SCH_2S$), 4.3-4.2 (1H, m, H-1'), 4.173 (1H, dd, J=2.6 Hz, J=9.2 Hz, H-5), 3.55-3.4 (1H, m, H-4), 3.44 (1H, dd, J=2.6 Hz, J=6.2 Hz, H-6), 1.29 (3H, d, J=6.3 Hz, $CH_3$) and 1.21 ppm (3H, d, J=7.21 Hz, $CH_3$).

EXAMPLE 11

Sodium (5R,6S)-6-[1'(R)-1-hydroxyethyl]-3-[[[(pyridin-3-yl)thio]-methyl]thio]-7-oxo-1-azabicyclo[3.2.0]hept-2-ene-2-carboxylate (Ih)

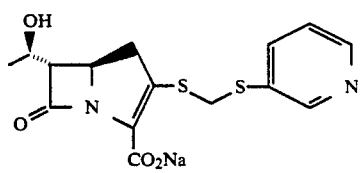

Step A p-Nitrobenzyl (5R,6S)-6-[1'(R)-hydroxyethyl]-3-[[[(pyridin-3-yl)thio]-methyl]thio]-7-oxo-1-azabicyclo[3.2.0]hept-2-ene-2carboxylate

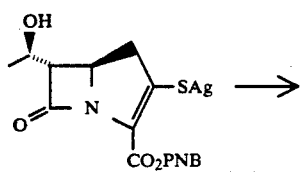

-continued

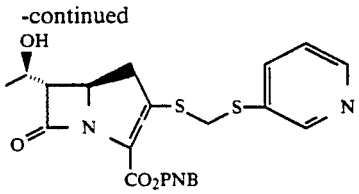

To a cold (ice bath) suspension of p-nitrobenzyl (5R,6S)-6-[1'(R)-hydroxyethyl]-3-silver mercapto-7-oxo-1-azabicyclo[3.2.0]hept-2-ene-2-carboxylate (3.0 g, 6.37 mmol) in DMF (30 mL) was added 3-[(chloromethyl)thio]-pyridine (1.22 g, 7.65 mmol) in DMF (10 mL), LiI (1.7 g, 12.74 mmol) and DIPEA (1.27 mL, 7.65 mmol). The mixture was stirred for 24 h at c.a. 22° C., then diluted with ice cold water (500 mL) and EtOAc (250 mL) and filtered through a pad of Celite. The pad was rinsed with EtOAc (5×200 mL) and the phases were separarated. The aqueous layer was extracted with EtOAc (2×50 mL). The organic layers were combined, washed with cold $H_2O$ (4×250 mL) and cold brine (250 mL), treated with activated charcoal (neutral) and dried (MgSO$_4$). The solid residue obtained upon evaporation of the solvent was triturated with $CH_2Cl_2$/ether (9.5/0.5, 40 mL), collected by filtration and rinsed with ether (10 mL) to give 1.17 (55%) of the title material.

IR ($CH_2Cl_2$) $\nu_{max}$: 3600, 3300-3100 (OH), 1790, 1685 (C=O) and 1518 cm$^{-1}$ ($NO_2$);

$^1$H NMR (acetone $D_6$, 200 MHz) δ8.64 (1H, d, J=2.2, pyridine H-2), 8.48 (1H, dd, J=1.5 Hz, J=4.8 Hz,, pyridine H-6), 8.25-8.2-0 (2H, m, PNB-H), 7.93-7.87 (1H, m, pyridine H-4), 7.79-7.74 (2H, d, J=8.8 Hz, PNB-H), 7.39-7.33 (1H, m, pyridine H-5), 5.53, 5.46, 5.30, 5.23 (2H, ABq, J=14.2 Hz, $CH_2$-PNB), 4.56, 4.55 (2H, part of ABq, $SCH_2S$), 4.34-4.23 (1H, m, H-5), 4.2-4.0 (1H, m, H-1'), 3.65, 3.61, 3.56, 3.52, 3.47, 3.43, 3.38 (2H, 7 lines out of 8, H-4), 3.34 (1H, dd, J=2.8 Hz, J=6.6 Hz, H-6), 2.86 (s, OH), 1.26 ppm (3H, d, J=6.3 Hz, $CH_3$).

Step B

Sodium (5R,6S)-6-[1'(R)-hydroxyethyl]-3-[[[(pyridin-3-yl)thio]-methyl]thio]-7-oxo-1-azabicyclo[3.2.0]hept-2-ene-2-carboxylate (Ih)

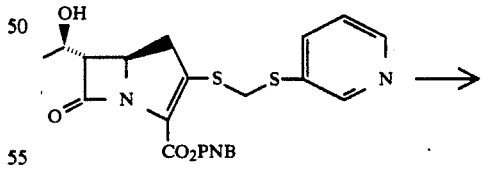

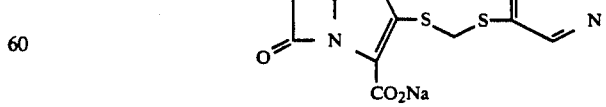

A solution of p-nitrobenzyl (5R,6S)-6-[1'(R)-hydroxyethyl]-3-[[[(pyridin-3-yl)thio]methyl]thio]-7-oxo-1-azabicyclo[3.2.0]hept-2-ene-2-carboxylate (400 mg, 0.82 mmole) in THF (30 mL), ether (30 mL) and a 0.05M pH 7.0 aqueous $NaH_2PO_4$/NaOH buffer solution (30 mL, 1.5 mmol) was shaken in a Parr hydrogenator for 1 h at 45 psi of $H_2$ at 10° C. to c.a. 22° C. using 10% Pd/C (400 mg) as catalyst. The mixture was diluted with ether (30 mL) and the catalyst was removed by filtration. It was rinsed with the pH 7.0 buffer solution (2×5 mL). The organic layer was separated and extracted with the buffer solution (2×25 mL). The aqueous phases were combined, washed with ether (2×25 mL) and passed through a $C_{18}\mu$BondaPak reversed phase column (30 g of the $C_{18}\mu$BondaPak reversed phase material; eluted first with $H_2O$ followed successively by 2%, 5%, 8% and 12% $CH_3CN/H_2O$) to give the title material (120 mg, 39%) as a lyophilized powder; purity 99.3% (as checked by HPLC); $T_{\frac{1}{2}}$22h (pH 7.4), $T_{\frac{1}{2}}$2 min (pH 2).

UV $\lambda^{H2O}_{max}$ 302 (10,500);

IR (Nujol) $\nu_{max}$: 3600-3100 (OH), 1745 and 1690 cm$^{-1}$

1H NMR ($D_2O$, 200 MHz) δ: 8.64-8.62 (1H, m, pyridine H-2), 8.5-8.46 (1H, m, pyridine H-2), 8.06-7.99 (1H, m, pyridine H-4), 7.48-7.41 (1H, m, pyridine H-5); 4.43, 4.36, 4.30, 4.21 (2H, ABq, J=14.0 Hz, SCH$_2$S), 4.27-4.15 (1H, m, H-1'), 4.08 (1H, dt, J=2.6 Hz, J=9.0 Hz, H-5), 3.32 (1H, dd, J=2.6 Hz, J=6.0 Hz, H-6), 3.28, 3.23, 3.19, 3.15, 3.07, 3.03, 2.98, 2.94 (2H, 8 lines, CH$_2$-4), 1.27 ppm (3H, d, J=6.4 Hz, CH$_3$).

EXAMPLE 12

Sodium
(4R,5S,6S)-6-[1'(R)-hydroxyethyl]-4-methyl-3-[[[(pyridin-3-yl)thio]methyl]thio]-7-oxo-1-azabicyclo[3.2.0-]hept-2-ene-2-carboxylate (Ii)

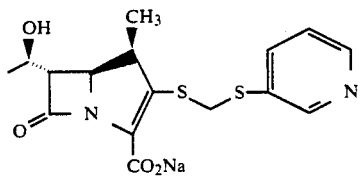

Step A p-Nitrobenzyl
(4R,5S,6S)-6-[1'(R)-hydroxyethyl]-4-methyl-3-[[[(pyridin-3-yl)
thio]methyl]thio]-7-oxo-1-azabicyclo[3.2.0]hept-2-ene-2-carboxylate

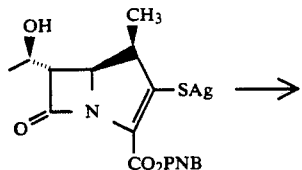

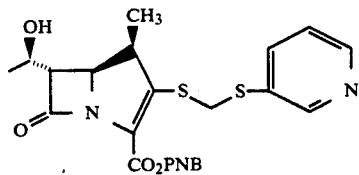

To a cold (ice bath) solution of p-nitrobenzyl (4R,5S,6S)-4-methyl-3-silver mercapto-7-oxo-1-azabicyclo[3.2.0]hept-2-ene-2-carboxylate (1.7 g, 3.5 mmol) in DMF (15 mL) was added a solution of 3-[(chloromethyl)thio]pyridine (670 mg, 4.2 mmol) followed by LiI (940 mg, 7.0 mmol) and DIPEA (0.69 mL, 4.2 mmol). The mixture was stirred for 22 h at c.a. 22° C. then diluted with ice cold $H_2O$ and EtOAc and filtered through a pad of Celite. The pad was rinsed with EtOAc (4×20 mL) and the aqueous layer was extracted with EtOAC (2×40 mL). The organic extracts were combined, washed with cold $H_2O$ (4×25 mL) and brine, dried (MgSO$_4$) and concentrated. The residue was then passed through a silica gel flash column (30 g of silica; the column eluted successively with $CH_2Cl_2$, 10%, 25% and 50%. $CH_2Cl_2$/EtOAc, EtOAc, 10% and 20% $CH_3CN$/EtOAc) to give the title material (804 mg, 46%).

IR ($CH_2Cl_2$) $\nu_{max}$: 3600-3200 (OH), 1775, 1710 cm$^{-1}$ (C=O) and 1520 cm$^{-1}$ (NO$_2$);

1H NMR (CDCl$_3$, 200 MHz) δ: 8.66-8.63 (1H, m, pyridine H-2), 8.55-8.49 (1H, m, pyridine H-6), 8.23-8.17 (2H, m, PNB-H), 7.80-7.71 (1H, m, pyridine H-4), 7.65-7.61 (2H, d, J=8.8 Hz, PNB-H), 7.28-7.22 (1H, m, pyridine H-4), 5.52, 5.45, 5.25, 5.18 (2H, ABq, J=13.8 Hz, CH -PNB), 4.30, 4.22, 4.15, 4.08 (2H, ABq, J=13.5 Hz, SCH$_2$S), 4.3-4.22 (2H, m, H-1' and H-5), 3.54-3.39 (1H, m, H-4), 3.27 (1H, dd, J=2.6 Hz, J=6.7 Hz, H-6), 1.84 (1H, 6s, OH), 1.36 (3H, d, J=6.3 Hz, CH$_3$) 1.24 ppm (3H, d, J=7.4 Hz, CH$_3$).

Step B

Sodium
(4R,5S,6S)-6-[1'(R)-hydroxyethyl]-4-methyl-3-[[[(pyridin-3-yl)thio]methyl]thio]-7-oxo-1-azabicyclo[3.2.0-]hept-2-ene-2-carboxylate (Ii)

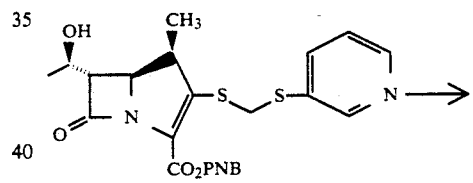

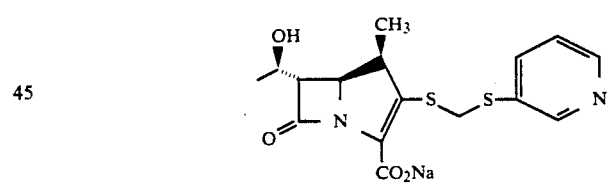

A solution of p-nitrobenzyl (4R,5S,6S)-6-[1'(R)-hydroxyethyl]-4-methyl-3-[[[(pyridin-3-yl)thio]methyl]-thio]-7-oxo-1-azabicyclo[3.2.0]hept-2-ene-2-carboxylate (725 mg, 1.44 mmol) in THF (45 mL), ether (45 mL) and a 0.05M pH 7.0 aqueous NaH$_2$PO$_4$/NaOH buffer solution (50 mL, 2.5 mmol) was shaken in a Parr hydrogenator at 45 psi H$_2$ for 1 h at 15° to 22° C. using 10% Pd/C (725 mg) as catalyst. The mixture was diluted with ether (50 mL). The catalyst was removed by filtration and rinsed with the pH 7.0 buffer solution (2 x 10 mL). The two solution phases were separated and the organic layer was extracted with the pH 7.0 aqueous buffer solution (1×10 mL). The aqueous layers were combined, washed with ether (2×25 mL) and passed through a reversed phase C$_{18}$ μBondaPak column (75 g of the reversed phase C$_{18}$ μBondaPak material; the column eluted first with H$_2$O followed successively by 2%, 5%, 10% and 15% CH$_3$CN/H$_2$O) to give the title material (220 mg, 39%); purity 99.6% (as checked by HPLC): T₁74 h (pH 7.4); T₁35 min (pH 2.0).

UV $\lambda^{H2O}_{max}$ 302 (9350), 258 (6000);

IR (Nujol) $\nu_{max}$: 3600–3200 (OH), 1740 and 1695 cm$^{-1}$ (C=O);

1H NMR (D₂O, 200 MHz) δ: 8.65, 8.64 (1H, d, J=2.0 Hz, pyridine (H-2), 8.49 (1H, dd, J=1.2 Hz, J=3.9 Hz, pyridine H-6), 3.05–8.0 (1H, m, pyridine H-5), 7.48–7.41 (1H, m, pyridine H-4), 4.46, 4.39, 4.22, 4.15 (2H, ABq, J=14.1 Hz, SCH₂S), 4.28–4.15 (1H, m, H-1'), 3.96 (1H, dd, J=2.5 Hz, J=9.2 Hz, H-5), 3.38 (1H, dd, J=2.5 Hz, J=6.1 Hz, H-6), 3.36–3.2 (1H, m, H-4), 1.28 (3H, d, J=6.3 Hz, CH₃), 1.12 ppm (3H, d, J=7.2 Hz, CH₃).

EXAMPLE 13

Sodium (5R,6S)-6-[1'(R)-hydroxyethyl]-3-[[[(p-chlorophenyl)-thio]methyl]thio]-7-oxo-1-azabicyclo[3.2.0]hept-2-ene-2-carboxylate (Ij)

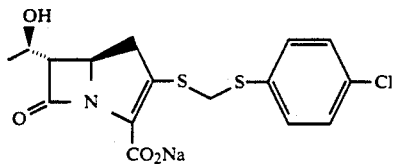

Step A p-Nitrobenzyl (5R,6S)-6-[1'(R)-hydroxyethyl]-3-[[[(p-chlorophenyl)-thio]methyl]thio]-7-oxo-1-azabicyclo[3.2.0]hept-2-ene-2carboxylate

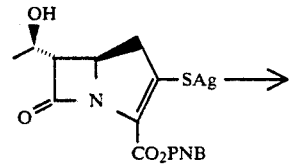

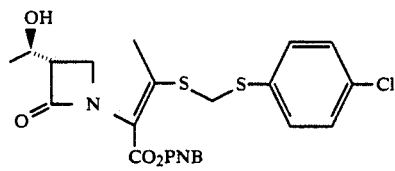

To a cold (ice bath) suspension of p-nitrobenzyl (5R,6S)-6-[1'(R)-hydroxyethyl]-3-silver mercapto-7-oxo-1-azabicyclo[3.2.0]hept-2-ene-2-carboxylate (471 mg, 1 mmol) in DMF (6 mL) was added chloromethyl 4-chlorophenyl sulfide (0.18 mL, 1.3 mmol), LiI (267 mg, 2 mmol) and DIPEA (0.20 mL, 1.2 mmol). The resulting mixture was stirred for 18 h, then diluted with cold H₂O (12 mL) and EtOAc (12 mL) and filtered through a pad of Celite. The pad was washed with EtOAc (6×15 mL) and the two solution phases were separated. The aqueous phase was extracted with EtOAc (3×15 mL). The organic extracts were combined, washed with cold H₂O (2×25 mL) and brine (25 mL) and dried (MgSO₄). The solid residue obtained upon solvent evaporation was triturated with an ether/CH₂Cl₂ mixture (9/11, 20 mL) to give the title material (355 mg, 68%) as a pale brown solid.

IR (CH₂Cl₂) $\nu_{max}$: 3600–3200 (OH), 1780, 1700 (C=O) and 1520 cm$^{-1}$ (NO₂);

1H NMR (CDCl₃, 200 MHz) δ: 8.23–8.1–8 (2H, m, PNB-H), 7.64, 7.60 (2H, bd, J=8.8 Hz, PNB-H), 7.39–7.25 (4H, m, aromatic H), 5.52, 5.45, 5.25, 5.18 (2H, ABq, J=13.9 Hz, CH₂-PNB), 4.3–4.16 (2H, m, H-1' and H-5), 4.16, 4.15 (2H, part of ABq, SCH₂S), 3.47, 3.42, 3.38, 3.33, 3.22, 3.18, 3.13, 3.09 (2H, m, CH₂₋₄), 3.20 (1H, dd, J=2.4 Hz, J=6.8 Hz, H-6), 1.73 (1H, bd, J=4.5 Hz, OH), 1.36 ppm (3H, d, J=6.3 Hz, CH₃).

Step B

Sodium (5R,6S)-6-[1'(R)-hydroxyethyl]-3-[[[(p-chlorophenyl)-thio]-methyl]thio]-7-oxo-1-azabicyclo[3.2.0]hept-2-ene-2-carboxylate (I1)

A solution of p-nitrobenzyl 5R,6S)-6-[1'(R)-hydroxyethyl]-3-[[[(p-chlorophenyl)thio]methyl]thio]-7-oxo-1-azabicyclo[3.2.0]hept-2-ene-2-carboxylate (900 mg, 1.73 mmol) in THF (40 mL), ether (40 mL) and a 0.05M phosphate buffer solution (pH 7.0, 64 mL, 3.2 mmol) was shaken on a Parr hydrogenator for 3 h at 45–50 psi H₂, using 10% Pd/C (2×900 mg) as catalyst. The catalyst was removed by filtration and washed with the pH 7.0 solution (2×10 mL). The organic phase was extracted with the pH 7.0 solution (2×10 mL). The aqueous extracts were combined, washed with ether (2×50 mL) and passed through a C₁₈ μBondaPak reversed phase column (90 g of the C₁₈ μBondaPak reversed phase material; the column eluted first with H₂O and then successively with 5%, 10% and 20% CH₃CN/H₂O) to give the title material that was repurified on the same type of column (20 g of the reversed phase material) to finally afford the pure material in good yield (212 mg, 30%); purity: 99.4% (as checked by HPLC); T₁26 h pH 7.4).

IR (Nujol) $\nu_{max}$: 3600–3200 (OH), 1760 and 1690 cm$^{-1}$ (C=O);

1H NMR (D₂O, 200 MHz) δ7.57–7.–39 (4H, m, aromatic-H), 4.39, 4.32, 4.27, 4.20 (2H, ABq, J=14.1 Hz, SCH₂S), 4.27–4.13 (1H, m, H-1'), 4.04 (1H, dt, J=2.4 Hz, J=9.2 Hz, H-5), 3.22 (1H, dd, J=2.6 Hz, J=6.1 Hz, H-4), 3.19, 3.14, 3.10, 3.05, 2.87, 2.83, 2.79, 2.74 (2H, m, CH₂₋₄), and 1.28 ppm (3H, d, J=6.4 Hz, CH₃).

EXAMPLE 14

Sodium (4R,5S,6S)-6-[1'(R)-hydroxyethyl]-4-methyl-3-[[[(p-chlorophenyl)thio]methyl]thio[-7-oxo-1-azabicyclo[3.2.0]hept-2-ene-2-carboxylate (Ik)

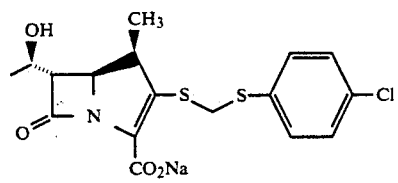

Step A p-Nitrobenzyl (4R,5S,6S)-6-[1(R)-hydroxyethyl]-4-methyl-3-[[[(p-chlorophenyl)thio]-methyl]thio]-7-oxo-1-azabicyclo[3.2.0]hept-2-ene-2-carboxylate

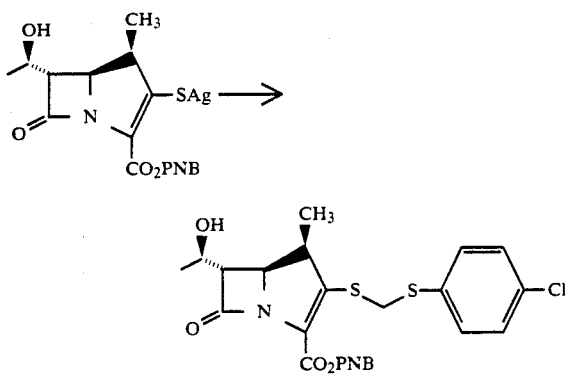

A cold (ice bath) suspension of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (1.5 g, 3.1 mmol) in DMF (15 mL) was treated with chloromethyl 4-chlorophenyl sulfide (0.56 mL, 3.9 mmol) followed by addition of LiI (422 mg, 6.2 mmol) and DIPEA (0.62 mL, 3.72 mmol). The resulting mixture was stirred for 23 h at c.a. 22° C., then diluted with cold H$_2$O (50 mL) and EtOAc (50 mL) and filtered to remove the solid. This solid was rinsed with EtOAc (2×20 mL). The aqueous phase was separated and extracted with EtOAc (2×20 mL). The organic phases were combined, washed with cold H$_2$O (2×50 mL) and brine (1×50 mL), dried (MgSO$_4$) and concentrated. The residue was passed through a silica gel flash column (30 g of silica gel; the column eluted first with CH$_2$Cl$_2$ followed successively by 10%, 20% and 30% EtOAc/CH$_2$Cl$_2$ to give the title material (819 mg, 49%) as an amorphous pale yellow solid.

IR (CH$_2$Cl$_2$) $\nu_{max}$: 3600–3200 (OH), 1775, 1710 (C=O), and 1520 cm$^{-1}$ (NO$_2$);

1H NMR (CDCl$_3$, 200 MHz) $\delta$8.24–8.17 (2H, m, PNB-H), 7.66–7.58 (2H, m, PNB-H), 7.38–7.24 (4H, m, aromatic-H), 5.51, 5.44, 5.24, 5.17 (2H, ABq, J=13.8 Hz, CH$_2$-PNB), 4.23 (1H, dd, J=2.6 Hz, J=9.9 Hz, H-5), 4.35–4.0 (1H, m, H-1'), 4.26, 4.20, 4.13, 4.06 (2H, ABq, J=13.4 Hz, SCH$_2$S), 3.55–3.35 (1H, m, H-4), 3.267 (1H, dd, J=2.6 Hz, J=6.8 Hz, H-6), 1.77 (1H, d, J=4.4 Hz, OH), 1.36 (3H, d, J=6.3 Hz, CH$_3$), 1.24 ppm (3H, d, J=7.3 Hz, CH$_3$).

Step B

Sodium (4R,5S,6S)-6-[1'(R)-hydroxyethyl]-4-methyl-3-[[[(p-chlorophenyl)thio]methyl]thio]-7-oxo-1-azabicyclo[3.2.0]hept-2-ene-2-carboxylate (Ik)

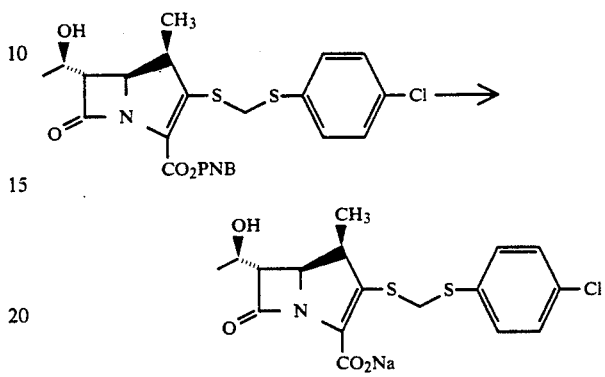

A solution of p-nitrobenzyl (4R,5S,6S)-6-[1'(R)hydroxyethyl]-4-methyl-3-[[[(p-chlorophenyl)thio]methyl]-thio]-7-oxo-1-azabicylo[3.2.0]hept-2-ene-2-carboxylate (800 mg, 1.49 mmol) in THF (40 mL), ether (40 mL) and a pH 7.0 NaH$_2$PO$_4$/NaOH buffer solution (0.05M, 56 mL, 2.8 mmol) was shaken on a Parr hydrogenolysis apparatus for 3 h at 45 psi H$_2$ using 10% Pd/C (800 mg) as catalyst. The catalyst was removed by filtration through a cake of Celite and the cake was rinsed with the pH 7.0 buffer solution (2×20 mL). The organic phase was separated and extracted with the 0.05M pH 7.0 phosphate buffer solution (2×20 mL). The aqueous layers were combined, washed with ether (2×50 mL) and passed through a C$_{18}$ $\mu$BondaPak reversed phase column (40 g of the C$_{18}$ $\mu$BondaPak reversed phase material; the column eluted first with H$_2$O followed successivley by 5%, 10% and 20% CH$_3$CN/H$_2$O) to give the title material (315 mg, 50%); purity 99.4% (as checked by HPLC); T$_{\frac{1}{2}}$97 h (pH 7.4).

UV $\lambda^{H2O}_{max}$306 (10,100), 262 (8050);

IR (Nujol) $\nu_{max}$: 3600–3200 (OH), 1750 and 1695 cm$^{-1}$ (C=O);

1H NMR (D$_2$O, 200 MHz) $\delta$: 7.56, 7.52 (2H, d, J=8.3 Hz, aromatic -H), 7.44, 7.39 (2H, d, J=8.3 Hz, aromatic-H), 4.43, 4.36, 4.19, 4.12 (2H, ABq, J=14.0 Hz, SCH$_2$S), 4.3–4.15 (1H, m, H-1'), 3.89 (1H, dd, J=8.9 Hz, H-5), 3.45 (1H, dd, J=2.4 Hz, J=6.0 Hz, H-6), 3.30–3.16 (1H, m, H-4), 1.28 (3H, d, J=6.3 Hz, CH$_3$), 1.10 ppm (3H, d, J=7.2 Hz, CH$_3$).

EXAMPLE 15

Sodium (4R,5S,6S)-6-[1'(R)-hydroxyethyl]-4-methyl-3-[[(methylsulfinyl)methylthio-7-oxo-1-azabicyclo[3.2.0]hept-2-ene-2-carboxylate (Im)

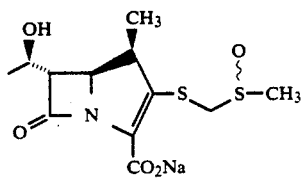

A cold (ice bath) solution of sodium (4R,5S,6S)-6-[1'(R)-1'-hydroxyethyl]-4-methyl-3-[[(methylthio)methyl]thio]-7-oxo-1-azabicyclo[3.2.0]hept-2-ene-2-carboxylate (Ib') (100 mg, 0.31 mmol) in H₂O (10 mL) was treated dropwise with a 30% aqueous solution of H₂O₂ (0.03 mL, 0.31 mmol) and stirred for 8.5 h at 5° C. (ice bath). The solution was then passed through a C₁₈μBondaPak reversed phase column (10 g of the C₁₈μBondaPak reversed phase material, the column eluted with H₂O) to give the title material as a mixture of diastereomeric sulfoxides, some as a pure product [78 mg, 74%, purity 99.54% (as checked by HPLC)] and some as an impure product [20 mg, 19%, purity 97.6% (as checked by HPLC)]; diastereomeric ratio: 6/4; T½46 h (pH 7.4).

UV λ$^{H2O}_{max}$296 (9600)

IR (Nujol) ν$_{max}$: 3600-3100 (OH), 1740 and 1600 cm$^{-1}$ (C=O);

¹H NMR (D₂O, 200 MHz) δ: 4.56, 4.49, 3.92, 3.99 (ABq, J=14.5 Hz, SCH₂S), 4.36, 4.29, 4.17, 4.09 (ABq, J=14.2 Hz, SCH₂S), 4.29-4.16 (2H, m, H-1 and H-5), 3.62-3.44 (2H, m, H-4 and H-6), 2.81 (1.8H, s, CH₃SO), 2.76 (1.2H, s, CH₃SO), 1.24 (3H, d, J=7.3 Hz, CH₃) and 1.22-1.19 ppm (3H, m, CH₃)

EXAMPLE 16

Sodium (4R,5S,6S)-3-[[[(p-chlorophenyl)sulfinyl]methyl]thio]-6-[1'(R)-hydroxyethyl]-4-methyl-7-oxo-1-azabicyclo[3.2.0]hept-2-ene-2-carboxylate (In)

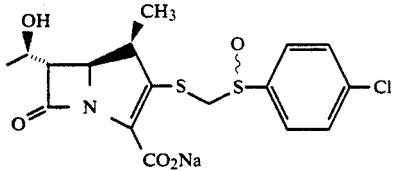

A cold (ice bath) solution of sodium (4R,5S,6S)-3-[[[(p-chlorophenyl)thio]methyl]thio]-6-[1'(R)-hydroxyethyl]-4-methyl-7-oxo-1-azabicyclo[3.2.0]hept-2-ene-2-carboxylate (Ik) (324 mg, 0.77 mmol) in H₂O (15 mL) was treated dropwise with a 30% aqueous H₂O₂ solution (0.087 mL, 0.77 mmol) and was stirred at 5° C. for two days. The cold aqueous solution was poured over a C₁₈ μBondapak reversed phase column (30 g the C₁₈ μBondapak reversed phase material; the column first eluted with H₂O followed successivley by 2%, 5% and 10% CH₃CN/H₂O) to give the title material (158 mg, 47%) as a 26/74 mixture of diastereomers; T½106 h (pH 7.4, 37° C.).

UV λ$^{H2O}_{max}$ 304 (8500);

IR (Nujol) ν$_{max}$: 3600-3200 (OH), 1750 and 1595 cm$^{-1}$ (C=O);

¹H NMR (D20, 200 MHz) δ: 7.81-7.-75 (2H, m, aromatic-H), 7.7-7.58 (2H, m, aromatic H), 4.50, 4.43, 4.32, 4.26 (0.7 H, ABq, J=13.6 Hz, SCH₂S), 4.41 (0.3H, s, SCH₂S), 4.18 (1H, center of 5 lines, J=6.2 Hz, H=1'), 3.57 (1H, dd, J=2.5 Hz, J=9.4 Hz, H-5), 3.33-3.28 (1H, m, H-6), 3.0-2.7 (1H, m, H-4), 1.25 (3H, d, J=6.3 Hz, CH₃), 1.02 ppm (3H, d, J=7.2 Hz, CH₃)

EXAMPLE 17

Sodium (4R,5S,6S)-6-[1'(R)-hydroxyethyl[-4-methyl-3-[[[[(pyridin-3-yl)methyl]thio]methyl]thio-7-oxo-1-azabicyclo[3.2.0]-hept-2-ene-2-carboxylate (Io)

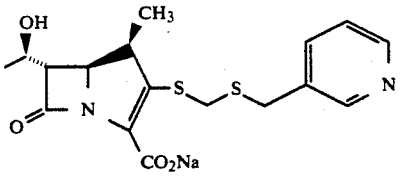

Step A p-Nitrobenzyl(4R,5S,6S)-6-[1'(R)-hydroxyethyl]-4-methyl-3-[[[[(pyridin-3-yl)methyl]thio]methyl]thio]-7-oxo-1-azabicyclo[3.2.0]hept-2-ene-2-carboxylate

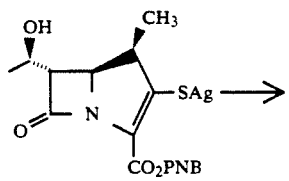

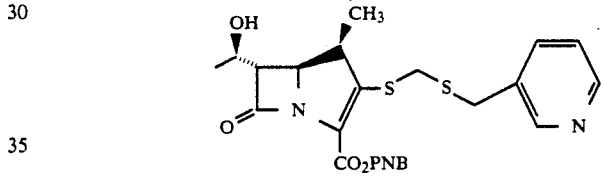

To a cold (ice bath) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (1.0 g, 2.06 mmol) in DMF (6 mL) was added a solution of freshly prepared 3-[[(chloromethyl)thio]methyl]pyridine (from 1.24 g, 10 mmol of 3-picolyl mercaptan) in DMF (4 mL) followed by LiI (280 mg, 4.12 mmol) and DIPEA (0.41 mL, 2.47 mmol). The resulting mixture was stirred for 18 h at c.a. 22° C., then diluted with cold H₂O (25 mL) and cold EtOAc (25 mL), and passed through a pad of Celite. The pad was washed with EtOAc (4×10 mL) and the two solution layers were separated. The aqueous phase was extracted with EtOAc (2×10 mL) and the organic fractions were combined. They were washed with cold H₂O (2×25 mL) and brine (25 mL) and dried (MgSO₄) The residue obtained upon evaporation of the solvent was passed through a silica gel column (20 g of silica; the column first eluted with CH₂Cl₂ followed successivley by 10%, 20%, 40% and 60% EtOAc/CH₂Cl₂ and finally with EtOAc) to give the title material (413 mg, 41%) as a yellow solid.

IR (CH₂Cl₂) ν$_{max}$: 3600-3200 (OH), 1775, 1710 (C=O) and 1520 cm$^{-1}$ (NO₂);

¹H NMR (CDCl₃, 200 MHz) δ: 8.54-8.48 (2H, m, aromatic-H), 8.24, 8.19 (2H, d, J=8.7 Hz, PNB-H), 7.68-7.62 (5H, m, aromatic H and PNB-H), 7.28-7.21 (1H, m, aromatic H), 5.56, 5.49, 5.27, 5.20 (2H, ABq, J=13.8 Hz, CH₂PNB), 4.27 (1H, dd, J=2.0 Hz, J=9.4 Hz, H-5), 3.85-3.7 (4H, m, H-1', SCH₂S, CH₂ pyridine), 3.65, 3.58 (1H, d, part of ABq, J=13.6 Hz, SCH₂S), 3.5-3.3 (1H, m, H-4), 3.25 (1H, dd, J=2.4 Hz, J=6.7 Hz, H-6), 1.68 (1H, bs, OH), 1.35 (3H, d, J=6.2 Hz, CH₃), 1.20 ppm (3H, d, J=7.3 Hz, CH₃).

Step B

Sodium (4R,5S,6S)-6-[1'(R)-hydroxyethyl]-4-methyl-3-[[[[(pyridin-3-yl)methyl]thio]methyl]thio]-7-oxo-1-azabicyclo[3.2.0]hept-2-ene-2-carboxylate (Io)

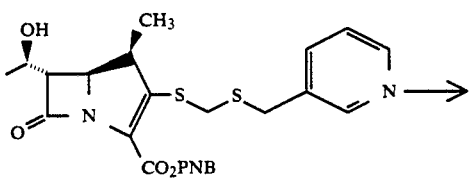

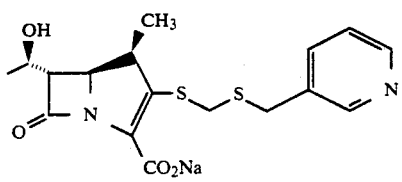

A solution of p-nitrobenzyl (4R,5B,6B)-6-[1'(R)hydroxyethyl]-4-methyl-3-[[[[(pyridin-3-yl)methyl]thio]-methyl]thio]-7-oxo-1-azabicyclo[3.2.0]hept-2-ene-2-carboxylate (718 mg, 1.39 mmol) in THF (40 mL), ether (40 mL) and a 0.05M pH 7.0 NaH₂PO₄/NaOH buffer solution (50 mL, 2.5 mmol) was shaken in a Parr hydrogenator at 45 psi H₂ for 3 h at c.a. 22° C. using 10% Pd/C (700 mg) as catalyst. The catalyst was removed by filtration and rinsed with the 0.05M pH 7.0 phosphate buffer solution (2×10 mL). The solution layers were separated and the organic layer was extracted with the 0.05M pH 7.0 phosphate buffer solution. The aqueous layers were combined, washed with ether (2×50 mL) and passed through a reversed phase C₁₈ μBondaPak column (40 g of the reversed phase C₁₈ μBondaPak material; the column first eluted with H₂O followed successively by 2%, 5%, 10% and 15% CH₃CN/H₂O) to give a grey solid after lyophilization (267 mg, 48%). This solid was passed again through a C₁₈ μBondaPak column (7.5 g of the C₁₈ μBondaPak material; the column eluted successively with H₂O and 2% and 5% CH₃CN/H₂O) to give the title compound (2.33 mg, 42%) as a white lyophilized solid; T₁77 h (pH 7.4, 37° C.), purity 99.9% (as checked by HPLC).

UV $\lambda^{H2O}_{max}$: 266 (6,003), 304(9790);

IR (Nujol) $\nu_{max}$: 3600-3200 (OH), 1750 and 1600 cm⁻¹ (C=O);

¹H NMR 200 MHz) δ: 8.53 (1H, bs, pyridine-H), 8.45, 8.42 bd, J=5.0 Hz, pyridine-H), 7.93, 7.88 (1H, bd, J=7.9 Hz pyridine-H), 7.48, 7.45, 7.44, 7.41 (1H, dd, J=5.1 Hz, J=7.8 Hz, pyridine-H), 4.30, 4.27, 4.24, 4.21, 4.18 (1H, 5 lines, H-1'), 4.11 (1H, dd, J=2.2 Hz, J=9.2 Hz, H-5), 3.95 (2H, s, CH₂-pyridine), 3.92, 3.85, 3.81, 3.74 (2H, ABq, J=13.8 Hz, SCH₂S), 3.39 (1H, dd, J=2.2 Hz, J=6.0 Hz, H-6), 3.30, 3.26, 3.22, 3.18, 3.14 (1H, 5 lines, H-4), 1.29 (3H, d, J=6.3 Hz, CH₃), 1.11 ppm (3H, d, J=7.3 Hz, CH₃).

EXAMPLE 18

Sodium (4R,5S,6S)-6-[1'(R)-hydroxyethyl]-4-methyl-3-[[[[(pyridin-3-yl)methyl]sulfinyl]methyl]thio]-7-oxo-1-azabicyclo[3.2.0]hept-2-ene-2-carboxylate (Ip)

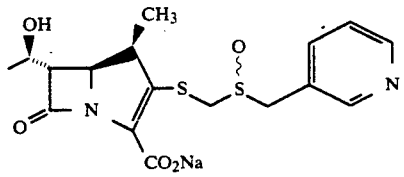

A cold (ice bath) solution of sodium (4R,5S,6S)-6-[1'(R)-hydroxyethyl]-4-methyl-3-[[[[(pyridin-3-yl)methyl]thio]methyl]thio]-7-oxo-1-azabicyclo[3.2.0]-hept-2-ene-2-carboxylate (Io) (390 mg, 0.97 mmol) in H₂O (20 mL) was treated with a cold solution of NaIO₄ (229 mg, 1.07 mmol) in H₂O (5 mL). The mixture was stirred for 2 h at 5° C., and then passed through a C₁₈ μBondaPak reversed phase column (50 g of the C₁₈ μBondaPak reversed phase material; the column eluted first with H₂O followed by 2% and 5%, CH₃CN/H₂O) to give after lyophilization a yellow solid (210 mg. 52%) and a less polar material (90 mg). This latter material was treated with NaHCO₃ (3 eq.) in cold H₂O (5 mL) and again passed through a reversed phase column (10 g of the reversed phase material, the column eluted with H₂O and then with 2% CH₃CN/H₂O) to give the title material (73 mg). The two fractions thus obtained were combined and rechromatographed through the C₁₈ μBondaPak column (30 g of the reversed phase material; the column successively eluted with H₂₀, 2% and 5% CH₃CN/H₂O) to afford the pure product (169 mg, 32%) as a 71/29 mixture of diastereomers; purity 99.2% (as checked by HPLC); T₁43 h (7.4, 37° C.).

UV $\lambda^{H2O}_{max}$ 266 (7,610), 272 (7,787), 2g8 (11,876);

IR (Nujol) $\nu_{max}$: 3600-3200 (OH), 1745 and 1600 cm⁻¹ (C=O);

¹H NMR (D₂O, 200 MHz) δ: 8.57-8.5-2 (2H, m, pyridine-H), 7.91-7.-85 (1H, m, pyridine-H), 7.56-7.49 (1H, m, pyridine-H), 4.56-3.90 (6H, m, H-1', H-5, CH₂-pyridine, SCH₂S), 3.45 (1H, dd, J=2.5 Hz, J=6.1 Hz, H-6), 3.37, 3.34, 3.30, 3.29, 3.26, 3.2 (1H, m, H-4), 1.28 (3H, d, J=6.3 Hz, CH₃), 1.17 (d, J=7.1 Hz, CH₃), 1.16 ppm (d, J=7.2 Hz, CH₃).

EXAMPLE 19

Sodium (4R,5S,6S)-3-[[[(3,4-dichlorophenyl)thio]methyl]thio]-6-[1'(R)-hydroxyethyl]-4-methyl-7-oxo-1-azabicyclo[3.2.0]-hept-2-ene-2-carboxylate (Iq)

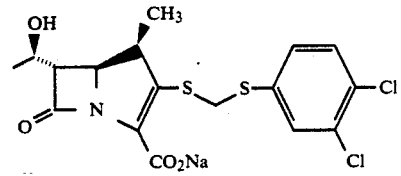

Step A p-Nitrobenzyl (4R,5S,6S)-3-[[[(3,4-dichlorophenyl)thio]-methyl]thio]-6-[1'(R)-hydroxyethyl]-4-methyl-7-oxo-1-azabicyclo[3.2.0]hept-2-ene-2-carboxylate

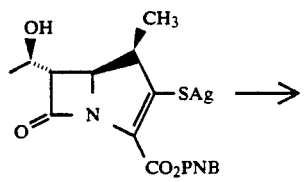

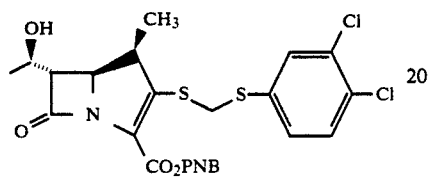

To a cold (ice bath) solution of p-nitrobenzyl (4R,5S,6S)-6-[1'(R)-hydroxyethyl]-3-silver mercapto-4-methyl-7-oxo-1-azabicyclo[3.2.0]hept-2-ene-2-carboxylate (1.00 g, 2.06 mmol) in DMF (6 mL) was added a solution of freshly prepared 1-chloromethylthio-3,4-dichlorobenzene (prepared from 3,4-dichlorophenyl mercaptan 1.27 mL, 10.0 mmol) in DMF (4 mL), followed by addition of LiI (280 mg, 4.12 mmol) and DIPEA (0.41 mL, 2.47 mmol). The resulting mixture was stirred for 18 h at c.a. 22° C., then diluted with cold EtOAc (20 mL) and cold H₂O (20 mL) and passed through a pad of Celite to remove the solid. The pad was washed with EtOAc (2×20 mL) and the two solution phases were separated. The aqueous phase was extracted with EtOAc (1×20 mL) and the organic fractions were combined, washed with H₂O (3×25 mL) and brine (7×25 mL), dried (MgSO₄) and concentrated. The residue was passed through a flash silica gel column (20 g of silica; the column eluted first with CH₂Cl₂ followed successively by 5%, 10%, 15% and 20% EtOAc/CH₂Cl₂) to give the title material (462 mg, 40%).

IR (CH₂Cl₂) $\nu_{max}$: 3600–3200 (OH), 1775 and 1710 cm⁻¹ (C=O);

¹H NMR (CDCl₃, 200 MHz) δ: 8.22–8.16 (2H, m, PNB-H), 7.64, 7.59 (2H, bd, J=8.7 Hz, PNB-H), 7.48, 7.478 (1H, d, J=2.1 Hz, aromatic-H), 7.38, 7.34 (1H, d, J=8.3 Hz, aromatic-H), 7.25, 7.24, 7.21, 7.20 (1H, dd, J=2.1 Hz, J-8.3 Hz, aromatic H), 5.51, 5.44, 5.25, 1.78 (2H, ABq, J=13.7 Hz, CH₂-PNB), 4.32–4.-14 (1H, m, H-1'), 4.25 (1H, dd, J=2.5 Hz, J=9.4 Hz, H-5), 4.27, 4.20, 4.14, 4.07 (2H, ABq, J=13.4 Hz, SCH₂S), 3.53–3.38 (1H, m, H-4), 3.27 (1H, dd, J=2.6 Hz, J=6.7 Hz, H-6), 1.61 (1H, bs, OH), 1.36 (3H, d, J=7.2 Hz, CH₃), 1.24 ppm (3H, d, J=6.3 Hz, CH₃).

Step B

Sodium (4R,5S,6S)-3-[[[(3,4-dichlorophenyl)thio]methyl]thio]-6-[1'(R)-hydroxyethyl]-4-methyl-7-oxo-1-azabicyclo[3.2.0]hept-2-ene-2-carboxylate (Iq)

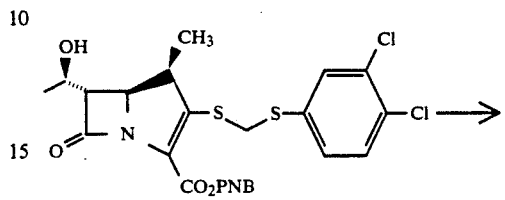

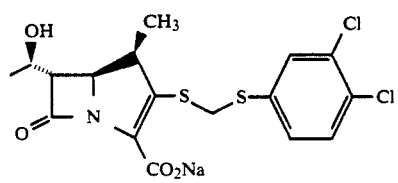

A solution of p-nitrobenzyl (4R,5S,6B)-3-[[[(3,4-dichlorophenyl)thio]methyl]thio]-6-[1'(R)-hydroxyethyl]-4-methyl-7-oxo-1-azabicyclo[3.2.0]hept-2-ene-2-carboxylate (447 mg, 0.786 mmol) in THF (15 mL), ether (15 mL) and a 0.10M pH 7.0 NaH₂PO₄/NaOH buffer solution (14.5 mL, 1.45 mmol) was shaken in a Parr hydrogenator at 40–45 psi H₂ for 2 h, using 10% Pd/C (447 mg) as catalyst. The catalyst was removed by filtration and washed with the buffer solution (2×10 mL). The two solution phases were separated and the organic phase was extracted with the buffer solution (2×10 mL). The aqueous phases were combined, washed with ether (3×20 mL) and passed twice through a C₁₈ μBondaPak reversed phase column (first elution: 27 g the C₁₈ μBondaPak reversed phase material; first eluted with H₂O followed successively by 2%, 5%, 10% and 20% CH₃CN/H₂O; second elution: 7.5 g of the reversed phase material; eluted successively with H₂O and 5%, 10% and 20% CH₃CN/H₂O) to give the title material (102 mg, 29%) as a lyophilized powder; $T_{\frac{1}{2}}$=99 h (pH 7.4, 37° C.), purity 99.3% (as checked by HPLC), UV $\lambda^{H2O}_{max}$304 (9120), 266 (7800);

IR (Nujol) $\nu_{max}$: 3600–3200 (OH), 1750 and 1600 cm⁻¹ (C=O);

¹H NMR (D₂O, 200 MHz) δ: 7.75, 7.74 (1H, d, J=2.0 Hz, aromatic H), 7.55, 7.51 (1H, d, J=8.4 Hz, aromatic H), 7.47, 7.46, 7.43, 7.42 (1H, dd, J=2.0 Hz, J=8.4 Hz, aromatic H), 4.46, 4.39, 4.21, 4.14 (2H, ABq, J=14.1 Hz, SCH₂S), 4.25–4.14 (1H, m, H-1'), 3.88 (1H, dd, J=2.5 Hz, J=9.1 Hz, H-5), 3.36 (1H, dd, J=2.5 Hz, J=6.0 Hz, H-6), 3.34–3.1 (1H, m, H-4), 1.28 (3H, d, J=6.3 Hz, CH₃), 1.11 ppm (3H, d, J=7.2 Hz, CH₃).

EXAMPLE 20

Sodium (4R,5S,6S)-6-[1'(R)-hydroxyethyl]-4-methyl-3-[[[(2,3,4,5,6-pentafluorophenyl)thio]methyl]thio]-7-oxo-1-azabicyclo[3.2.0]hept-2-ene-2-carboxylate (Ir)

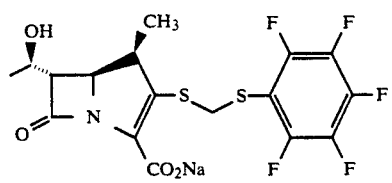

Step A p-Nitrobenzyl (4R,5S,6S)-6-[1'(R)-hydroxyethyl]-4-methyl-3-[[[(2,3,4,5,6-pentafluorophenyl)thio]methyl]-thio]-7-oxo-1-azabicyclo[3.2.0]hept-2-ene-2-carboxylate

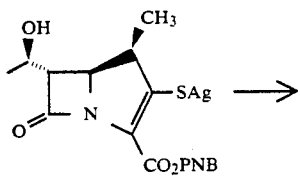

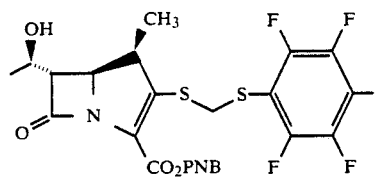

A cold (ice bath) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (2.0 g, 4.12 mmol) in DMF (12 mL) was treated with a solution of freshly prepared 1-chloromethylthio-2,3,4,5,6-pentafluorobenzene (prepared from 1-mercapto-2,3,4,5,6-pentafluorobenzene; 1.33 mL, 100 mmol) in DMF (8 mL), LiI (560 mg, 8.24 mmol) and DIPEA (0.82 mL, 4.94 mmol). The mixture was stirred for 18 h at c.a. 22° C., then diluted with ice cold $H_2O$ (40 mL) and EtOAc (40 mL) and filtered over a pad of Celite. The pad was rinsed with EtOAc (3×10 mL) and the two solution phases were separated. The aqueous layer was extracted with EtOAc (2×20 mL). The organic phases were then combined, washed with ice cold $H_2O$ (3×50 mL) and brine (50 mL), dried ($MgSO_4$) and concentrated. The residue was passed through a silica gel column (40 g of silica; the column successively eluted with $CH_2Cl_2$ and 2%, 5%, 8% and 10% $EtOAc/CH_2Cl_2$ to give the title material (820 mg, 34%).

IR ($CH_2Cl_2$) $v_{max}$: 3600-3400 (OH), 1780, 1715 (C=O) and 1520 cm$^{-1}$ ($NO_2$);

$^1$H NMR ($CDCl_3$, 200 MHz) δ: 8.25-8.21 (2H, m, PNB-H), 7.68, 7.63 (2H, bd, J=8.7 Hz, PNB-H), 5.58, 5.52, 5.31, 5.24 (2H, ABq, J=13.6 Hz, $CH_2$ PNB), 4.88 (2H, s, $SCH_2S$), 4.26 (1H, dd, J=2.7 Hz, J=9.4 Hz, H-5), 4.29-4.2 (1H, m, H-1'), 3.26 (1H, dd, J=2.7 Hz, J=6.8 Hz, H-6), 3.0-2.8 (1H, m, H-4), 1.65 (1H, d, J=4.6 Hz, OH), 1.33 (3H, d, J=6.2 Hz, $CH_3$), 1.04 ppm (3H, d, J=7.3 Hz, $CH_3$).

Step B

Sodium (4R,5S,6S)-6-[1'(R)-hydroxyethyl]-4-methyl-3-[[[(2,3,4,5,6-pentafluorophenyl) thio]methyl]thio]-7-oxo-1-azabicyclo-[3.2.0]hept-2-ene-2-carboxylate (Ir)

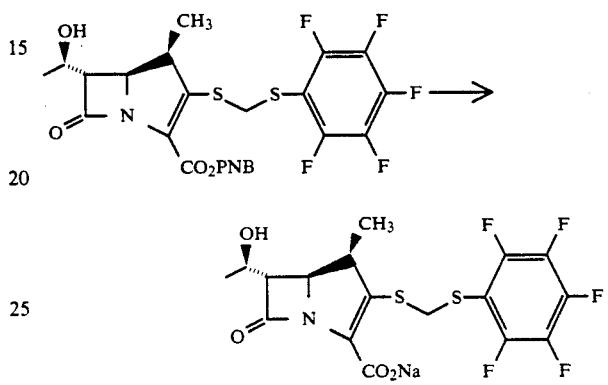

A solution of p-nitrobenzyl (4R,5S,6S)-6-[1'(R)-hydroxyethyl]-4-methyl-3-[[[(2,3,4,5,6-pentafluorophenyl)-thio]methyl]thio]-7-oxo-1-azabicyclo[3.2.0-]hept-2-ene-2-carboxylate (200 mg, 0.34 mmol) in THF (10 mL), ether (10 mL) and a 0.10M pH 7.0 $NaH_2PO_4$/NaOH buffer solution (6.3 mL, 0.63 mmol) was shaken in a Parr hydrogenator for 3 h at 40-45 psi $H_2$ using 10% Pd/C (200 mg) as catalyst. The catalyst was removed by filtration and rinsed with the pH 7.0 buffer solution (2×5 mL) and ether (1×10 mL). The two solution layers were separated, and the organic layer was extracted with the pH 7.0 buffer solution (2×5 mL). The aqueous phases were frozen until further manipulation was required. The organic layer was treated again in a Parr Shaker with 10% Pd/C catalyst (130 mg) for 2 h at 40-45 psi $H_2$ and was subjected to the similar extraction process described above. Finally, all the aqueous layers were combined and passed through a $C_{18}$ μBondaPak reversed phase column (30 g of the $C_{18}$ μBondaPak reversed phase material; the column first eluted with $H_2O$ followed by 2%, 5% and 10% $CH_3CN/H_2O$) to give the title material (45 mg, 28%); purity 100% as checked by HPLC); $T_{\frac{1}{2}}$=41 h (pH 7.4, 37° C.).

UV: $\lambda^{H2O}_{max}$304 (13,600);

IR (Nujol) $v_{max}$: 3600-3200 (OH), 1750 and 1600 cm$^{-1}$ (C=O);

$^1$H NMR ($D_2O$, 200 MHz) δ: 4.82 (2H, s, $SCH_2S$), 4.28-4.15 (1H, m, H-1'), 4.18 (1H, dd, J=2.6 Hz, J=9.3 Hz, H-5), 3.42 (1H, dd, J=2.6 Hz, J=6.2 Hz, H-6), 3.01, 2.98, 2.94, 2.89, 2.86 (1H, 5 lines, H-4), 1.26 (3H, d, J=6.4 Hz, $CH_3$) and 1.02 ppm (3H, d, J=7.3 Hz, $CH_3$).

EXAMPLE 21

Sodium (4R,5S,6S)-6-[1'(R)-hydroxyethyl]-3-[[(isopropylthio)-methyl]thio]-4-methyl-7-oxo-1-azabicyclo[3.2.0]hept-2-ene-2-carboxylate (Is)

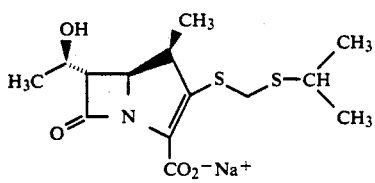

Step A p-Nitrobenzyl (4R,5S,6S)-6-[1'(R)-hydroxyethyl]-3-[[(isopropylthio)-methyl]thio]-4-methyl-7-oxo-1-azabicyclo[3.2.0]hept-2-ene-2-carboxylate

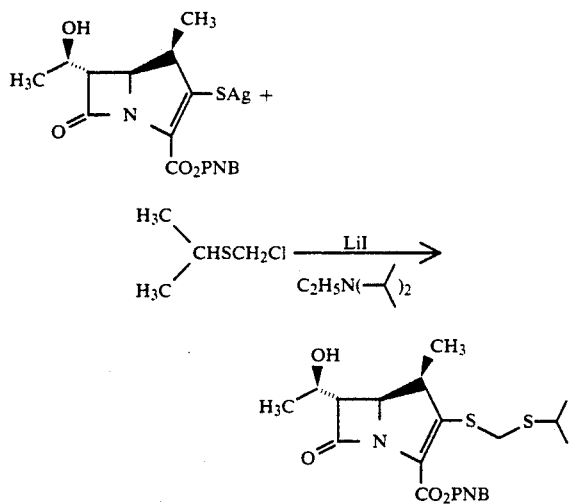

A cold (2° C.) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (7.279 g, 15.0 mmol) in 60 mL of dried dimethylformamide was treated with a solution of 2-[(chloromethyl)thio]-propane (2.805 g, 22.5 mmol) in 15 mL of dried dimethylformamide, lithium iodide (6.023 g, 45.0 mmol) and N,N-diisopropylethylamine (2.908 g, 3.92 mL, 22.5 mmol). After stirring for 1 h at 5° C. and 18 h at 20° C., the solution was diluted with ethyl acetate (150 mL) and cold (2° C.) water (150 mL) and filtered through a pad of Celite. The organic phase was separated from the aqueous phase, and the aqueous phase was extracted with ethyl acetate (3×150 mL). The organic layers were combined, washed with water (3×100 mL) and brine (200 mL), dried (MgSO4), filtered and evaporated. The crude product (4.87 g) was purified by silica gel chromatography (250 g of silica; eluted with dichloromethane/ethyl acetate, 3/1) to afford 2.483 g (35%) of the title product as a yellow foam.

$^1$H NMR (CDCl$_3$; 200 MHz) δ: 1.24–2.37 (12H, m, 1'-CH$_3$, 4-CH$_3$, CH$_3$'s of isopropyl), 3.15 (1H, m, CH of isopropyl), 3.26 (1H, dd, J=2.58 Hz, 6.80 Hz, H-6), 3.56 (1H, m, H-4), 3.91 (2H, ABq, —SCH$_2$S—), 4.22–4.29 (2H, m, H-5, H-1'), 5.36 (2H, ABq, CO$_2$, 7.92 ppm (4H, ABq, aromatic H's).

Step B

Sodium (4R,5S,6S)-6-[1'(R)-hydroxyethyl]-3-[[(isopropylthio)-methyl]thio]-4-methyl-7-oxo-1-azabicyclo[3.2.0]hept-2-ene-2-carboxylate (Is)

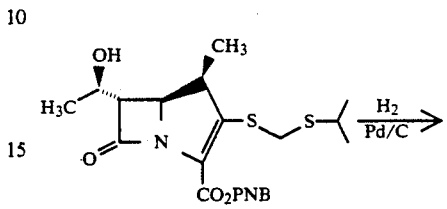

A solution of p-nitrobenzyl (4R,5S,6S)-6-1'(R)-hydroxyethyl]-3-[[(isopropylthio)]methyl]thio]-4-methyl-7-oxo-1-azabicyclo[3.2.0]hept-2-ene-2-carboxylate (1.399 g, 3.0 mmol) in a mixture of ether (30 mL) and tetrahydrofuran (30 mL) was added to 60 mL of a pH 7.0, 0.1M NaH2PO4/NaOH buffer. The resulting mixture was subjected to hydrogenolysis over 10% Pd/C catalyst (1.399 g) at 42 psi hydrogen for 3 h. The catalyst was removed by filtration over a pad of Celite and washed with ether (30 mL) and the pH 7.0 buffer solution (30 mL). The aqueous phase was separated and chromatographed on reversed phase silica gel, eluted with 5–15% acetonitrile in water. The pertinent fractions were pooled and lyophilized. The solid obtained was rechromatographed on reversed phase silica gel, eluted with acetonitrile/water (12/88). Once again, the pertinent fractions were pooled and lyophilized to afford 0.357 g (33%) of the title product as a slightly beige solid.

IR (KBr) ν$_{max}$: 1599 (—CO$_2$—), 1750 cm$^{-1}$ (β-lactam);

UV (water) λ$_{max}$: 304 nm (ε 11046);

$^1$H NMR (D$_2$O; 200 MHz) δ: 1.20–1.31 (12H, m, 1'-CH$_3$, 4-CH$_3$, CH$_3$'s of isopropyl) 3.42–3.59 (2H, m, H-4, H-6), 4.01 (2H, ABq, —SCH$_2$S—), 4.20–4.32 ppm (2H, m, H-1', H-5).

EXAMPLE 22

Sodium (4R,5S,6S)-6-[1'(R)-hydroxyethyl]-3-[[[(phenylmethyl)-thio]methyl]thio]-4-methyl-7-oxo-1-azabicyclo[3.2.0-]hept-2-ene-2-carboxylate (It)

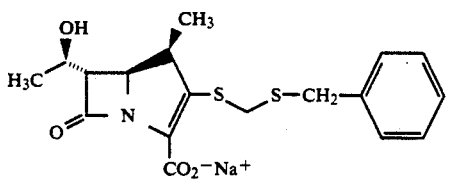

Step A p-Nitrobenzyl (4R,5S,6S)-6-[1'(R)-hydroxyethyl]-3-[[[(phenylmethyl)-thio]methyl]thio]-4-methyl-7-oxo-1-azabicyclo[3.2.0-]hept-2-ene-2-carboxylate

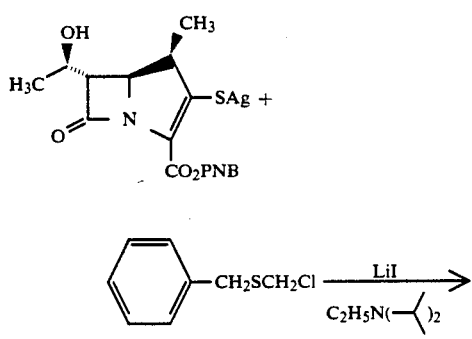

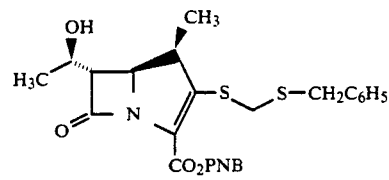

A cold (2° C.) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (7.279 g, 15.0 mmol) in 60 mL of dried dimethylformamide was treated with a solution of chloromethylthiomethylbenzene (3.885 g, 22.5 mmol) in 15 mL of dried dimethylformamide, lithium iodide (6.023 g, 45.0 mmol) and N,N-diisopropylethylamine (2.908 g, 3.92 mL, 22.5 mmol). After stirring for 1 h at 5° C. and 18 h at 20° C., the solution was diluted with ethyl acetate (150 mL) and cold (2° C.) water (150 mL) and filtered through a pad of Celite. The organic phase was separated from the aqueous phase. The aqueous phase was extracted with ethyl acetate (3×150 mL). The organic phases were combined and washed with water (3×100 mL) and brine (200 mL), dried (MgSO$_4$), filtered and evaporated. The crude product (5.18 g) was purified by silica gel chromatography (250 g of silica; eluted with dichloromethane/ethyl acetate, 3/1) to afford 2.772 g (36%) of the title product as a yellow foam.

$^1$H NMR (CDCl$_3$; 200 MHz) δ1.17 (3H, d, J=7.33 Hz, 4-CH$_3$), 1.35 (3H, d, J=6.26 Hz, 1'-CH$_3$), 3.24 (1H, dd, J=2.5 Hz, 6.72 Hz, H-6), 3.39 (1H, m, H-4), 3.68 (2H, ABq, —SCH$_2$S—), 3.83 (2H, ABq, —SCH$_2$C$_6$H$_5$), 4.18-4.28 (2H, m, H-5, H-1'), 5.38 (2H, ABq, CO 7.24-7.31 (5H, m, —SCH$_2$C$_6$H$_5$), 7.93 ppm (4H, ABq, CO$_2$CH$_2$C$_6$H$_4$NO$_2$).

Step B

Sodium (4R,5S,6S)-[1'(R)-hydroxyethyl]-3-[[[(phenylmethyl)-thio]-methyl]thio]-4-methyl-7-oxo-1-azabicyclo[3.2.0-]hept-2-ene-2-carboxylate (It)

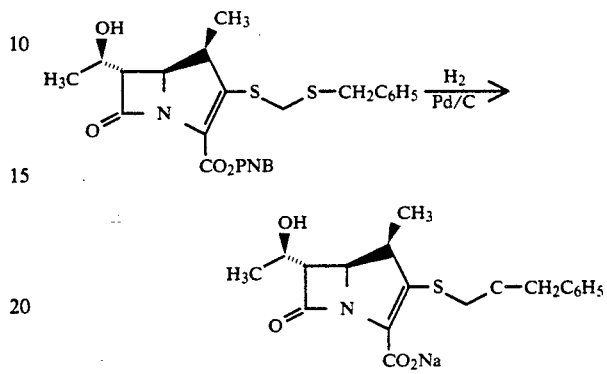

A solution of p-nitrobenzyl (4R,5S,6S)-6-[1'(R)-hydroxyethyl]-3-[[[(phenylmethyl)thio]methyl]thio]-4-methyl-7-oxo-1-azabicyclo[3.2.0]hept-2-ene-2-carboxylate (1.544 g, 3.0 mmol) in a mixture of ether (30 mL) and tetrahydrofuran (30 mL) was added to 60 mL of a pH 7.0, 0.1M NaH$_2$PO$_4$/NaOH buffer solution. The resulting mixture was subjected to hydrogenolysis over 10% Pd/C catalyst (1.544 g) at 42 psi H$_2$ for 3 h. The catalyst was removed by filtration over a pad of Celite and was washed with ether (30 mL) and the pH 7.0 buffer solution (30 mL). The aqueous phase was separated from the organic phase and chromatographed on reversed phase silica gel, eluted with 5-20% acetonitrile in water; the pertinent fractions were pooled and lyophilized. The solid thus obtained was rechromatographed on reversed phase silica gel, eluted with acetonitrile/water (15/85); the pertinent fractions were once again pooled and lyophilized to afford 0.390 g (32%) of the title compound as a white powder.

IR (KBr) $\nu_{max}$: 1599 (—CO$_2$—), 1750 cm$^{-1}$ (β-lactam);

UV (water) $\lambda_{max}$: 304 nm (ε 11019);

$^1$H NMR (D$_2$O; 200 MHz) δ1.09 (3H, d, J=7.26 Hz, 4-CH$_3$), 1.29 (3H, d, J=6.35 Hz, 1'-CH$_3$), 3.15 (1H, m, H-4), 3.38 (1H, dd, J=2.47 Hz, 6.03 Hz, H-6), 3.81 (2H, ABq, —SCH$_2$S—), 3.92 (2H, s, —SCH$_2$C$_6$H$_5$), 4.10 (1H, dd, J=2.36 Hz, 9.13 Hz, H-5), 4.23 (1H, m, H-1'), 7.33-7.43 ppm (5H, m, —SCH$_2$C$_6$H$_5$).

EXAMPLE 23

Sodium (4R,5S,6S)-6-[1'(R)-hydroxyethyl]-3-[[[[((furan-2-yl)-methyl]thio]methyl]thio]-4-methyl-7-oxo-1-azabicyclo-3.2.0]hept-2-ene-2-carboxylate (Iu)

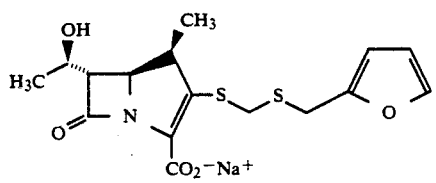

Step A p-Nitrobenzyl (4R,5S,6S)-6-[1'(R)-hydroxyethyl-3-[[[[((furan-2-yl)methyl]thio]methyl]thio]-4-methyl-7-oxo-1-azabicyclo[3.2.0]hept-2-ene-2-carboxylate

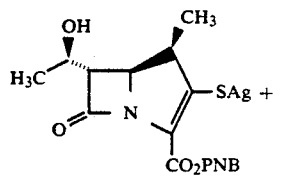

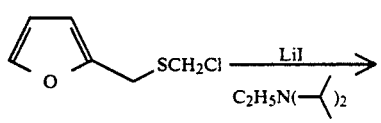

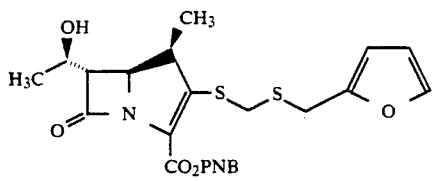

A cold (2° C.) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (7.279 g, 15.0 mmol), in 60 mL of dried dimethylformamide was treated with a solution of 2-[[(chloromethyl)thio]methyl]furan (3.659 g, 22.5 mmol) in 15 mL of dried dimethylformamide, lithium iodide (6.023 g, 45.0 mmol) and N,N-diisopropylethylamine (2.908 g, 3.92 mL, 22.5 mmol). After stirring for 1 h at 5° C. and 18 h at 20° C., the solution was diluted with ethyl acetate (150 mL) and cold (2° C.) water (150 mL) and filtered over a pad of Celite. The organic phase separated from the aqueous phase; the aqueous phase was extracted with ethyl acetate (3×150 mL). The organic phases were combined, washed with water (3×100 mL) and brine (200 mL), dried (MgSO4), filtered and evaporated. The crude product (3.80 g) was purified by silica gel chromatography (250 g of silica; eluted with dichloromethane/ethyl acetate, 3/1) to afford 2.471 g (33%) of the title product as a yellow foam.

$^1$H NMR (CDCl$_3$; 200 MHz) δ: 1.23 (3H, d, J=7.31 Hz, 4-CH$_3$), 1.34 (3H, d, J=6.25 Hz, 1'-CH$_3$), 3.26 (1H, dd, J=2.57 Hz, 6.74 Hz, H-6), 3.47 (1H, m, H-4), 3.79 (2H, ABq, furanyl —SH$_2$), 3.88 (2H, ABq, —SCH$_2$S—), 4.21-4.28 (2H, m, H-5, H-1'), 5.36 (2H, ABq, CO$_2$CH$_2$), 6.19, 6.29 and 7.35 (1H, 1H, 1H, m, m, m, furanyl H's), 7.92 ppm (4H, ABq, CO$_2$CH$_2$C$_6$H$_4$NO$_2$).

Step B

Sodium (4R,5S,6S)-6-[1'(R)-hydroxyethyl]-3-[[[[(furan-2-yl)methyl]thio]methyl]thio]-4-methyl-7-oxo-1-azabicyclo[3.2.0]hept-2-ene-2-carboxylate (Iu)

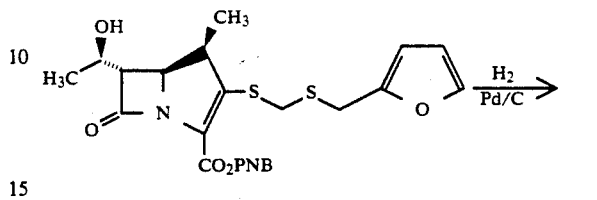

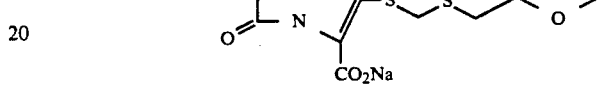

A solution of p-nitrobenzyl (4R,5B,6S)-6-[1'(R)-hydroxyethyl]-3-[[[[(furan-2-yl)methyl]thio]methyl]thio]-4-methyl-7-oxo-1-azabicyclo[3.2.0]hept-2-ene-2-carboxylate (1.512 g, 3.0 mmol) in a mixture of ether (30 mL) and tetrahydrofuran (30 mL) was added to 60 mL of pH 7.0, 0.1M NaH$_2$PO$_4$/NaOH buffer solution. The resulting mixture was subjected to hydrogenolysis over 10% Pd/C catalyst (1.512 g) at 42 psi H$_2$ for 3 h. The catalyst was removed by filtration over a pad of Celite and washed with ether (30 mL) and the pH 7.0 buffer solution (30 mL). The aqueous phase was separated from the organic phase and chromatographed on reversed phase silica gel, eluted with 5-20% acetonitrile in water; the pertinent fractions were pooled and lyophilized. The solid thus obtained was rechromatographed on reversed phase silica gel, eluted with acetonitrile/water (12/88); the pertinent fractions were once again pooled and lyophilized to afford 0.339 g (29%) of the title product as a white powder.

IR (KBr) ν$_{max}$: 1599 (—CO$_2$—), 1750 cm$^{-1}$ (β-lactam);

UV (water) λ$_{max}$: 304 nm (ε 10989);

$^1$H NMR (D$_2$O; 200 MHz) δ1.17 (3H, d, J=7.24 Hz, 4-CH$_3$), 1.30 (3H, d, J=6.36 Hz, 1'-CH$_3$), 3.32 (1H, m, H-4), 3.42 (1H, dd, J=2.44 Hz, 5.93 Hz, H-6), 3.89 (2H, ABq, —SCH$_2$S), 3.95 (2H, ABq, furanyl —SCH$_2$), 4.15-4.28 (2H, m, H-5, H-1'), 6.37, 6.43 and 6.50 ppm (1H, 1H, 1H, m, m, m, furanyl H's).

EXAMPLE 24

Sodium (4R,5S,6S)-6-[1'(R)-hydroxyethyl]-4-methyl-3-[[1(R and S)-(methylthio)ethyl]thio]-7-oxo-1-azabicyclo[3.2.0]hept-2-ene-2-carboxylate (Iv)

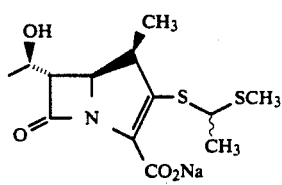

p-Nitrobenzyl (4R,5S,6S)-6-[1'(R)-hydroxyethyl-4-methyl-3-[[1-(methylthio)ethyl]thio]-7-oxo-1-azabicyclo[3.2.0]hept-2-ene-2-carboxylate

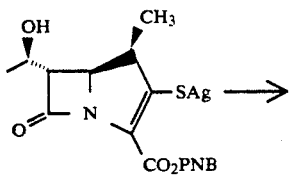

→

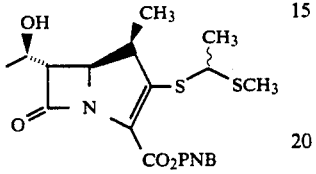

A cold (ice bath) solution of p-nitrobenzyl (4R,5S,6S)-6-[1'(R)-hydroxyethyl]-4-methyl-3-silver mercapto-7-oxo-1-azabicyclo[3.2.0]hept-2-ene-2-carboxylate (242 mg, 0.5 mmol) in DMF (2 mL) was treated dropwise with a solution of 1-chloroethyl methyl sulfide (69 mg, 0.625 mmol) in DMF (1 mL), LiI (68 mg, 1.0 mmol) and DIPEA (0.1 mL, 0.6 mmol). The resulting mixture was stirred at 5° C. for 30 min, then treated again with 0.5 eq. of the previous reagents (CH$_3$CHClSCH$_3$, LiI and DIPEA). The mixture was stirred for an additional 30 min, then diluted with ice cold EtOAc (20 mL) and H$_2$O (20 mL) and filtered over a pad of Celite. The pad was rinsed with EtOAc (3 × 10 mL) and the two solution layers were separated. The aqueous layer was extracted with EtOAc (3 × 10 mL). The organic phases were combined and washed with ice cold H$_2$O (4 × 20 mL) and brine (20 mL), dried (MgSO$_4$), and concentrated. The residue was purified on preparative TLC (eluted with CH$_2$Cl$_2$/EtOAc, 1/1) to give the title compound (73 mg, 32%) as a mixture of diastereomers. Each diastereomers were separated by preparative TLC (eluted with ether) and were characterized separately.

Isomer A, the less polar isomer:

IR (CH$_2$Cl$_2$) $\nu_{max}$: 3600–3300 (OH), 1770–1710 (C=O) and 1520 cm$^{-1}$ (NO$_2$);

$^1$H NMR (CDCl$_3$, 200 MHz) δ: 8.25–8.19 (2H, m, PNB-H), 7.68–7.64 (2H, m, PNB-H), 5.56, 5.49, 5.27, 5.20 (2H, ABq, J=13.8 Hz, CH$_2$-PNB), 4.37, 4.34, 4.30 (1H, part of q, J=7.0 Hz, SCHS), 4.28 (1H, dd, J=2.4 Hz, J=9.4 Hz, H-5), 4.34–4.23 (1H, m, H-1'), 4.8–4.6 (1H, m, H-4), 3.28 (1H, dd, J=2.6 Hz, J=6.8 Hz, H-6), 2.13 (3H, s, SCH$_3$), 1.65 (3H, d, J=7.0 Hz, CHCH$_3$), 1.37 (3H, d, J=6.3 Hz, CH$_3$), 1.28 ppm (3H, d, J=7.4 Hz, CH$_3$).

Isomer B, the more polar isomer:

IR (CH$_2$Cl$_2$) $\nu_{max}$: 3600–3320 (OH), 1770, 1710 (C=O) and 1520 cm$^{-1}$ (NO$_2$);

$^1$H NMR (CDCl$_3$, 200 MHz) δ: 8.25–8.-19 (2H, m, PNB-H), 7.69–7.-64 (2H, d, J=8.9 Hz, PNB-H), 5.56, 5.49, 5.27, 5.20 (2H, ABq, J=13.8 Hz, CH$_2$PNB), 4.3–4.2 (1H, m, hidden H-1'), 4.26 (1H, dd, J=2.5 Hz, J=9.3 Hz, H-5), 4.24, 4.21, 4.17 (1H, part of q, J=6.8 Hz, SCHS), 3.7–3.35 (1H, m, H-4), 3.28 (1H, dd, J=2.6 Hz, J=6.8 Hz, H-6), 2.28 (3H, s, SCH$_3$), 1.76 (1H, bs, OH), 1.65 (3H, d, J=6.8 Hz, CHCH$_3$), 1.38 (3H, d, J=6.3 Hz, CH$_3$), 1.28 ppm (3H, d, J=7.3 Hz, CH$_3$).

Step B

Sodium (4R,5S,6S)-6-[1'(R)-hydroxyethyl]-4-methyl-3-[[(1-methylthio)ethyl]thio]-7-oxo-1-azabicyclo[3.2.0]hept-2-ene-2-carboxylate (Iv)

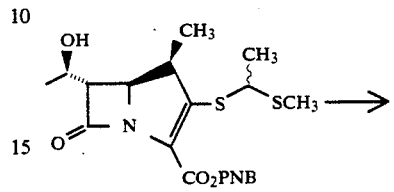

→

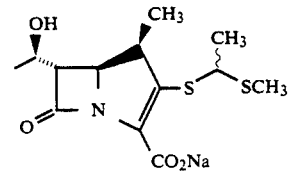

A solution of p-nitrobenzyl (4R,5B,6B -6-[1'(R)-hydroxyethyl]-4-methyl-3-[[1-(methylthio)ethyl]thio]-7-oxo-1-azabicyclo[3.2.0]hept-2-ene-2-carboxylate (isomer A, 120 mg, 0.26 mmol) in THF (10 mL), ether (10 mL) and a 0.10M NaH$_2$PO$_4$/NaOH buffer solution (4.7 mL, 0.47 mmol) was shaken on a Parr hydrogenator for 1.5 h at 40–45 psi H$_2$ using 10% Pd/C as catalyst (120 mg). The catalyst was removed by filtration and the organic phase was separated from the aqueous phase and treated again with H$_2$ at 40–45 psi in the Parr shaker in the presence of 10% Pd/C catalyst (120 mg) and the pH 7.0 NaH$_2$PO$_4$/NaOH buffer solution. The mixture was shaken for 1.5 h after which the catalyst was removed by filtration. The aqueous phases from the two hydrogenolysis steps were combined, washed with ether (3 × 20 mL) and then passed through a C$_{18}$ μBondaPak column (30 g of the C$_{18}$ μBondaPak column material; the column eluted first with H$_2$O followed successively by 2%, 5% and 10% CH$_3$CN/H$_2$O) to give the title material as a grey solid. The solid was repurified on the C$_{18}$ μBondaPak column (7 g of the C$_{18}$ BondaPak material; successively eluted with H$_2$O, 5% and 10% CH$_3$CN/H$_2$O) to give one pure isomer Iv-A (35 mg, 40%); purity 96.9% as checked by HPLC); T$_{\frac{1}{2}}$20 min (pH 2, 37° C.).

UV λ: $\lambda^{H_2O}_{max}$302 (7045);

IR (Nujol) $\nu_{max}$: 3600–3200 (OH), 1745 and 1600 cm$^{-1}$ (C=O);

$^1$H NMR (D$_2$O, 200 MHz) δ: 4.47, 4.44, 4.40, 4.37 (1H, q, J=7.0 Hz, SCHS), 4.31–4.18 (1H, m, H-1'), 4.23 (1H, dd, J=2.5 Hz, H-5), 3.65, 3.62, 3.58, 3.57, 3.53, 3.50 (1H, 6 lines, H-4), 3.44 (1H, dd, J=2.5 Hz, J=6.1 Hz, H-6), 2.15 (3H, s, CH$_3$), 1.60 (3H, d, J=7.0 Hz, CH$_3$), 1.29 (3H, d, J=6.4 Hz, CH$_3$), 1.21 ppm (3H, d, J=7.3 Hz, CH$_3$)

The similar steps with the isomer B of p-nitrobenzyl (4R,5S,6S)-6-[1'(R)-hydroxyethyl]-4-methyl-3-[[1-(methylthio)ethyl]thio]-7-oxo-1-azabicyclo[3.2.0]hept-2-ene-2-carboxylate gave another isomer Iv-B. (37 mg, 42%); purity 99.0% (as checked by HPLC); T$_{\frac{1}{2}}$56 h (pH 7.4, 37° C.), 20 min (pH 2.0, 37° C.).

UV $^{H_2O}_{max}$302 (9831);

IR (Nujol) ν$_{max}$: 3600-3200 (OH), 1750 and 1600 cm$^{-1}$ (C=O);

$^1$H NMR (D$_2$O, 200 MHz) δ: 4.36, 4.33, 4.29, 4.26 (1H, q, J=6.8 Hz, SCHS), 4.21 (part of dd, J=2.4 Hz, part of H-5), 0 4.29-4.21 (1H, m, hidden H-1'); 3.44 (1H, dd, J=2.4 Hz, J=6.1 Hz, H-6), 3.50-3.34 (1H, m, hidden H-4), 2.29 (3H, s, 1 CH$_3$), 1.60 (3H, d, J=6.8 Hz, CH—CH$_3$), 1.29 (3H, d, J=6.4 Hz, CH$_3$), 1.21 ppm (3H, d, J=7.3 Hz, CH$_3$).

EXAMPLE 25

Sodium 4R,5S,6S)-3-[[[(p-cyanophenyl)thio]methyl]thio]-6-[1'(R)-hydroxyethyl]-4-methyl-7-oxo-1-azabicyclo[3.2.0]hept-2-ene-2-carboxylate (Iw)

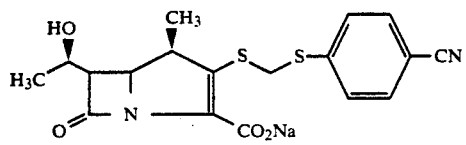

Step B 4-(Bromomethyl)thiobenzonitrile

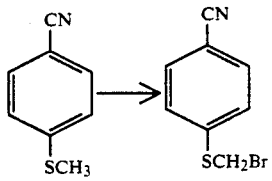

A solution of 4-(methylthio)benzonitrile 0.300 g, 2 mmol) and N-bromosuccinimide (0.445 g, 2.5 mmol) in benzene was refluxed for 26 h. Then the mixture was cooled and filtered. The filtrate was evaporated, taken up in cold CCl$_4$ 10 mL) and filtered again. This operation was repeated another time. Finally, evaporation of the solvent left 0.32 g 70%) of the title product as a yellow oil which solidified.

IR (CH$_2$Cl$_2$) ν$_{max}$: 2223 cm$^{-1}$ (—CN);

$^1$H NMR (CDCl$_3$, 200 MHz) δ7.65 (2H, d, aromatic-H, J=8.59), 7.51 (2H, d, aromatic-H, J=8.59 Hz), 4.88 ppm (2H, s, S-CH$_2$—).

Step B p-Nitrobenzyl (4R,5S,6S)-3-[[[(p-cyanophenyl)thio]-methyl]thio]-6-[1'(R)-hydroxyethyl]-4-methyl-7-oxo-1-azabicyclo[3.2.0]hept-2-ene-2-carboxylate

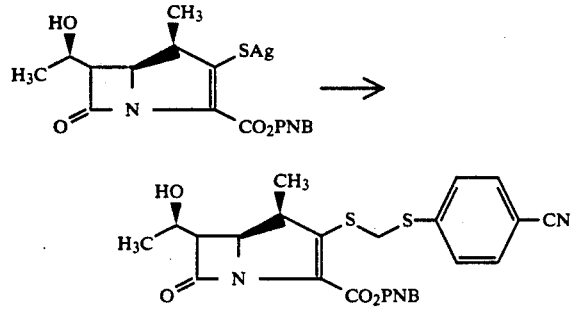

To a cold (5° C.) solution of p-nitrobenzyl 14R,5S,6S)-6-[1'(R)-hydroxyethyl]-4-methyl-3-silver mercapto-7-oxo-1-azabicyclo[3.2.0]hept-2-ene-2-carboxylate (0.606 g, 1.25 mmol) in dimethylformamide (5 mL) was added dropwise a solution of 4-[(bromomethyl)thio]benzonitrile (0.328 g, 1.44 mmol) in dimethylformamide (1 mL), followed by LiI (0.255 g, 3.75 mmol) and N,N-diisopropylethylamine (0.37 mL, 2.19 mmol). The reaction mixture was stirred at room temperature for 18 h, then diluted with ethyl acetate (25 mL) and water (25 mL) and filtered. The two layers were separated; the aqueous phase extracted with ethyl acetate (3×10 mL). The organic phases were combined and washed with cold water and brine. Then the organic solution was dried (MgSO$_4$) and evaporated. The crude compound was purified by silica gel chromatography (eluted with 0% to 20% ethyl acetate/CH$_2$Cl$_2$) to afford 0.298 g (45%) of the title product as a yellow solid.

IR (CH$_2$Cl$_2$) ν$_{max}$: 2223 (—CN), 1775 (β-lactam), 1710 cm$^{-1}$ (—CO$_2$—);

$^1$H NMR (CDCl$_3$, 200 MHz) δ: 8.22 (2H, d, aromatic-H), 7.64 (2H, d, aromatic-H), 7.59 (2H, d, aromatic-H), 7.42 (2H, d, aromatic-H), 5.29 (2H, ABq, CH$_2$-Bz), 4.23-4.30 (4H, m, —CH$_2$S, H-1', H-5), 3.50 (1H, m, H-4), 3.30 (1H, dd, J =2.56, 6.74 Hz), 1.38 (3H, d, J =6.25 Hz, 1'-CH$_3$), 1.28 ppm (3H, d, J =7.27, 4-CH$_3$).

Step C

Sodium (4R,5S,6S)-3-[[[(p-cyanophenyl)thio]methyl]thio]-6-[1'(R)-hydroxyethyl]-4-methyl-7-oxo-1-azabicyclo[3.2.0]hept-2-ene-2-carboxylate (Iw)

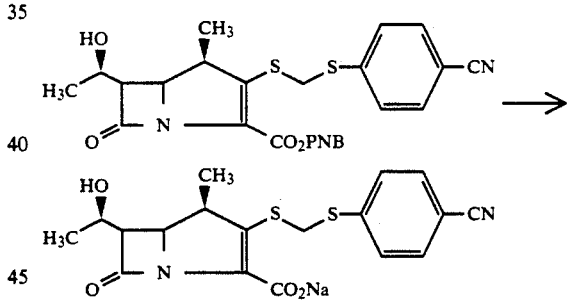

A solution of p-nitrobenzyl (4R,5S,6S)-3-[[[(p-cyanophenyl)thio]methyl]thio]-6-[1'(R)-hydroxyethyl]-4-methyl-7-oxo-1-azabicyclo[3.2.0]hept-2-ene-2-carboxylate (0.168 g, 0.32 mmol) in tetrahydrofuran (12 mL) was added to a mixture of Et$_2$O (12 mL) and 0.1M NaH$_2$PO$_4$/NaOH buffer solution (pH: 7.0, 6 mL) solution. The mixture was subjected to hydrogenolysis over 10% Pd/C catalyst (0.168 g) at 45 psi H$_2$ for 2.75 h. Then the catalyst was filtered off and the filtrate extracted with Et$_2$O. The aqueous phase was chromatographed on reversed phase silica gel, eluted with 0-10% CH$_3$CN/water. The pertinent fractions were combined and lyophilized to afford 0.30 g (22.7%) of the title compound.

IR (Nujol) ν$_{max}$: 1750 (β-lactam), 1590 cm$^{-1}$ (—CO$_2$-).

$^1$H NMR (D$_2$O, 200 MHz), δ: 7.44 (2H, d, aromatic-H), 7.61 (2H, d, aromatic-H), 4.44 (2H, ABq, —CH$_2$—), 4.25 (1H, m, H-1'), 4.10 (1H, dd, J =2.36, 9.27 Hz, H-5), 3.28-3.45 (2H, m, H-4, H-6), 1.30 (3H, d, J =6.29 Hz, 1'-CH$_3$), 1.10 ppm (3H, d, J =7.21 Hz, 4-CH$_3$).

EXAMPLE 26

Sodium (4R,5S,6S)-3-[[[(p-carbamoylphenyl)thio]-methyl]thio]-6-[1'(R)-hydroxyethyl]-4-methyl-7-oxo-1-azabicyclo[3.2.0]hept-2-ene-2-carboxylate (Ix)

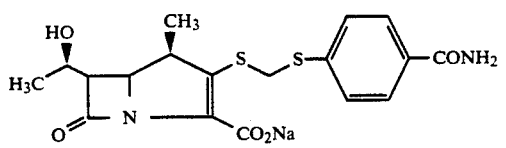

Step A

4-[(Chloromethyl)thio]benzamide

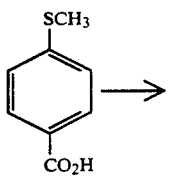

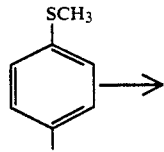

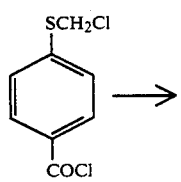

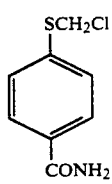

A solution of 4-[(methylthio)benzoic acid (1.68 g, 10 mmol) in SOCl₂ (5 mL) was refluxed for 1 h. Then the solvent was evaporated to leave a solid. The crude acid chloride formed was dissolved in CH₂Cl₂ (10 mL), cooled in an ice bath and treated slowly (45 min) with a solution of SO₂Cl₂ 1.48 g, 11 mmol) in CH₂Cl₂ (5 mL). After the mixture was stirred for 2 h at 5° C., the solvent was evaporated. The crude product was dissolved in C₆H₆ (50 mL) and the solution was saturated, at 20° C., with NH₃. The precipitate formed immediately. After allowed to be stirred for 15 min, the white solid was collected and chromatographed on silica gel (eluted with CH₃CN) to afford 1.74 g (86.2%) of the title amide; m.p. 140°-42° C.

IR (CH₂Cl₂) $v_{max}$: 1680 (—CO—), 1595 cm⁻¹ (aromatic).

¹H NMR (CDCl₃, 200 MHz) δ: 7.80 (2H, δ, aromatic-H), 7.54 (2H, δ, aromatic-H), 5.03 ppm (2H, S, —CH₂).

Step B p-Nitrobenzyl (4R,5S,6S)-3-[[[(p-carbamoylphenyl)-thio]methyl]thio]-6-[1'(R)-hydroxyethyl]-4-methyl-7-oxo-1-azabicyclo[3.2.0]hept-2-ene-2-carboxylate

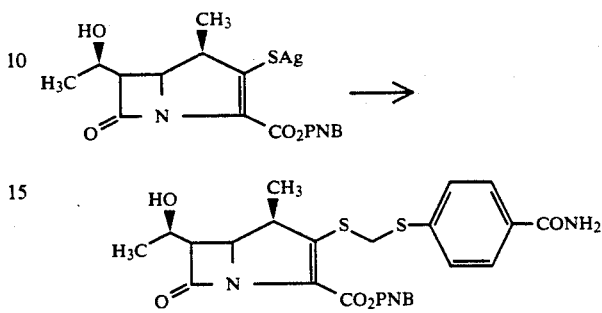

A cold (5° C.) solution of pi-nitrobenzyl (4R, 5S, 6S)-6-[1'(R)-hydroxyethyl]-4-methyl-3-silver mercapto-7-oxo-1-azabicyclo[3.2.0]hept-2-ene-2-carboxylate (500 mg, 1.03 mmol) in dimethylformamide (10 mL) was treated with 4-[(chloromethyl)thio]benzamide (0.239 g, 1.19 mmol), LiI (0.414 g, 3.09 mmol) and N,N-diisopropylethylamine (0.233 g, 1.8 mmol) dropwise. The mixture was stirred at 5° C. for 2 h and 20° C. for 16 h, diluted with ethyl acetate, shaken vigorously with cold diluted HCl and filtered. The two solution phases were separated, and the aqueous solution was extracted with ethyl acetate. The combined organic extracts were washed with brine, dried (MgSO₄) and evaporated. The crude product was purified by silica gel chromatography (eluted first with ethyl acetate and then with CH₃CN) to afford 0.322 g, (57.5%) of the title product as a brownish foam.

IR (CH₂Cl₂) $v_{max}$: 1772 (v-lactam), 1710 (—CO₂PNB), 1675 cm⁻¹(CONH₂).

¹H NMR (CDCl₃, 200 MHz), δ: 8.19 (2H, d, aromatic-H), 7.73 (2H, d, aromatic-H), 7.62 (2H, d, aromatic-H), 7.43 (2H, d, aromatic-H), 5.34 (2H, ABq, CH₂-Bz), 4.40–4.10 [4H, H-1', 4.28 (2H, ABq, CH₂S, 4.17 (1H, dd, J =2.53, 9.25Hz, H-5)], 3.39 (1H, m, H-4), 3.25 (1H, dd, J =2.54, 6.70Hz, H-6), 1.35 (3H, d, J =6.26Hz, 1'-CH₃), 1.24 ppm (3H, d, J=7.28Hz, 4-CH₃).

Step C

Sodium (4R,5S,6S)-3-[[[p-carbamoylphenyl)thio]methyl]thio]-6-[1'(R)-hydroxyethyl]-4-methyl-7-oxo-1-azabicyclo[3.2.0]hept-2-ene-2-carboxylate (Ix)

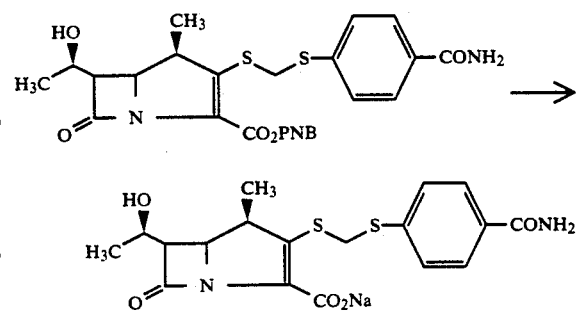

A solution of p-nitrobenzyl (4R,5S,6S)-3-[[[(p-carbamoylphenyl)thio]methyl]thio]]-6-[1'(R)-hydroxyethyl]-4-methyl-7-oxo-1-azabicyclo[3.2.0]hept-2-ene-2-carboxylate (0.543 g, 1 mmol) in tetrahydrofuran (40 mL) was added to a mixture of Et₂O (40 mL) and 0.1M NaH₂PO₄/NaOH buffer solution (pH:7.0, 20 mL). The mixture was subjected to hydrogenolysis over 10% Pd/C catalyst (0.543 g) at 40 psi H₂ for 3 h. Then the catalyst was filtered off and the filtrate extracted with Et₂O. The aqueous phase was chromatographed on reversed phase silica gel being, eluted with 0-10% CH₃CN/water. The pertinent fractions were combined and lyophilized to afford 0.130 g (30.2%) of the title compound.

IR (nujol) $\nu_{max}$: 1740 ($\beta$-lactam), 1660 (—CONH₂), 1590 cm⁻¹ (—CO₂—);

¹H NMR (D₂O, 200 MHz) δ: 7.77 (2H, d, aromatic-H), 7.61 (2H, d, aromatic-H), 4.37 (2H, ABq, —CH₂S—), 4.19 (1H, m, H-1'), 3.87 (1H, dd, J=2.35Hz, 9.19, H-5), 3.36 (1H, dd, J=2.46, 6.07Hz, H-6), 3.56 (1H, m, H-4), 1.26 (3H, d, J=6.33Hz, 1'-CH₃), 1.12 ppm (3H, d, J =7.24Hz, 4-CH₃).

EXAMPLE 27

Sodium (4R,5S,6S)-3-[[[[(p-aminomethyl)phenyl]thio]methyl]-thio]-6-[1'(R)-hydroxyethyl]-4-methyl-7-oxo-1-azabicyclo[3.2.0]hept-2-ene-2-carboxylate (Iy)

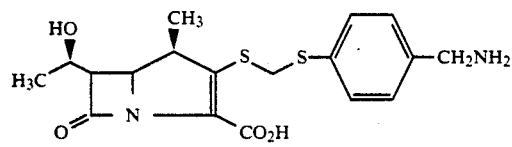

Step A 4-(Methylthio)benzylazide

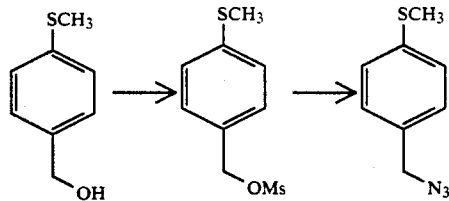

A cold (5° C.) solution of 4-methylthiobenzyl alcohol (3.0 g, 19.45 mmol) in CH₂Cl₂ (60 mL) was treated with triethylamine (2.17 g, 21.4 mmol) and methanesulfonyl chloride (2.45 g, 21.4 mmol). The mixture was stirred for 1 h, then diluted with Et₂O and filtered. The filtrate was evaporated to dryness, redissolved in CH₃CN and treated with NaN₃ (1.52 g, 23.34 mmol) and (Bu)₄NCl (0.150 g). The mixture was stirred at room temperature for 18 h, then diluted with ethyl acetate and washed successively with water, dilute NaHCO₃ and brine, dried (MgSO₄), and finally evaporated. The crude compound was purified by silica gel chromatography (eluted with petroleum ether and CH₂Cl₂) to afford 2.79 g (80.0%) of the title product as a mobile oil.

IR (CH₂Cl₂) $\nu_{max}$: 2200 cm⁻¹ (—N₃);

¹NMR (CDCl₃, 200 MHz) δ: 7.25 (4H, s, aromatic-H), 4.29 (2H, s, CH₂—), 2.49 ppm (3H, s, —CH₃).

Step B

4-[(Chloromethyl)thio]benzylazide

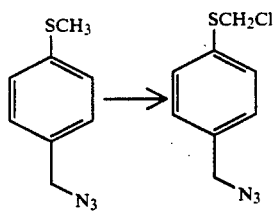

A solution of 4-(methylthio)benzylazide (0.359 g, 2 mmol) in CH₂Cl₂ was cooled in ice and treated slowly with SO₂Cl₂ (0.297 g, 2.2 mmol). The reaction mixture was stirred at 5° C. for 1.5 h and then evaporated to dryness. The crude compound was obtained as a yellow oil.

IR (neat) $\nu_{max}$: 2200 cm⁻¹ (—N₃).

¹H NMR (CDCl₃, 200 MHz) δ: 7.53 (2H, d, aromatic-H), 7.33 (2H, d, aromatic-H) 4.98 (2H, s, —SCH₂—), 4.36 ppm (2H, s, —CH₂N₃).

Step C p-Nitrobenzyl (4R,5S,6S)-3-[[[[(p-azidomethyl)phenyl]thio]methyl]-thio]-6-[1'(R)-hydroxyethyl]-4-methyl-7-oxo-1-azabicyclo[3.2.0]hept-2-ene-2-carboxylate

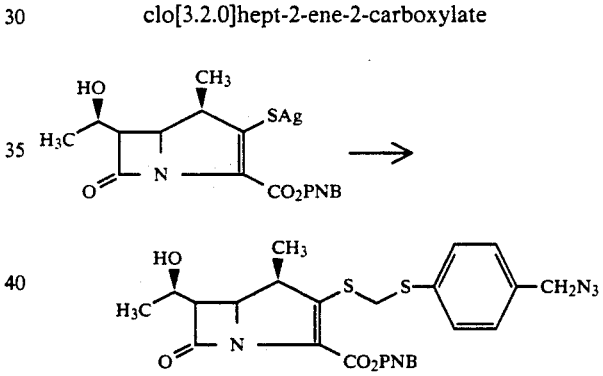

A cold (5° C.) solution of p-nitrobenzyl (4R,5S,6S)-6-1'(R)-hydroxyethyl]-4-methyl-3-silver mercapto-7-oxo-1-azabicyclo[3.2.0]hept-2-ene-2-carboxylate (849 mg, 1.75 mmol) in DMF (15 mL) was treated with 4-[(chloromethyl)thio]benzylazide (0.417 g, 2 mmol), LiI (0.703 g, 5.25 mmol) and N,N-diisopropylethylamine (0.396 g, mmol). After stirring for 20 h at 5° C., the solution was diluted with ethyl acetate and shaken vigorously with cold diluted aqueous HCl. The mixture was filtered and the organic phase separated. The aqueous solution was extracted with ethyl acetate. The organic phases were combined, washed with brine, dried (MgSO₄) and evaporated. The crude product was purified by silica gel chromatography (eluted with 0-10% CH₃CN/CH₂Cl₂) to afford 0.485 g (49.9%) of the title product.

IR (CH₂Cl₂) $\nu_{max}$: 2200 (—N₃), 1772 ($\beta$-lactam), 1710 cm⁻¹ (—CO₂—);

1H NMR (CDCl₃, 200 MHz) δ: 8.20 (2H, d, aromatic-H), 7.63 (2H, d, aromatic-H), 7.44 (2H, d, aromatic-H), 7.27 (2H, d, aromatic-H), 5.36 (2H, ABq, —CH₂Bz), 4.45–4.12 [(6H, m, —CH₂N₃ (4.34, s), —CH₂S (4.22, ABq), H-5, H-1')], 3.45 (1H, m, H-4), 3.27 (1H, dd, J=2.55, 6.77 Hz, H-6), 1.36 (3H, d, J=6.27 Hz, 1'-CH₃), 1.24 ppm (3H, d, J=7.31 Hz, 4-CH₃).

Step D

Sodium (4R,5S,6S)-3-[[[[(p-aminomethyl)phenyl]thio]methyl]-thio]-6-1'(R)-hydroxyethyl]-4-methyl-7-oxo-1-azabicyclo[3.2.0]-hept-2-ene-2-carboxylate (Iy)

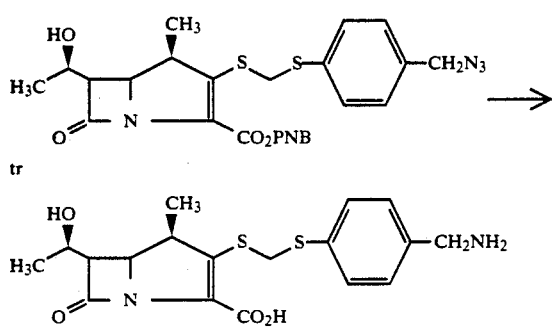

A solution of p-nitrobenyzl (4R,5S,6S)-3-[[[[(p-azidomethyl)phenyl]thio]methyl]thio]-6-[1'(R)-hydroxyethyl]-4-methyl-7-oxo-1-azabicyclo[3.2.0]hept-2-ene-2-carboxylate (0.470 g, 0.846 mmol) in tetrahydrofuran was added to a mixture of Et₂O (32 mL) and a 0.1M NaH₂PO₄/NaOH buffer solution (pH: 7.0, 16 mL). The mixture was subjected to hydrogenolysis over 10% Pd/C catalyst (0.420 g) at 40 psi H₂ for 3.75 h. The catalyst was then filtered off and the filtrate extracted with Et₂O. The aqueous phase was chromatographed on reversed phase silica gel, eluted with 10–25% CH₃CN/water. The pertinent fractions were combined and lyophilized to afford 0.065 g (19.5%) of the title compound.

IR (Nujol) ν$_{max}$: 1753 (β-lactam), 1580 cm⁻¹ (—CO₂⁻).

¹H NMR (D₂O, 200 MHz) δ: 7.62 (2H, d, aromatic-H), 7.43 (2H, d, aromatic-H), 4.31 (2H, ABq, SCH₂—), 4.20 (2H, s, —CH₂N ), 4.25 (1H, m, H-1 ), 3.99 (1H, dd, J=2.51, 9.56 Hz, H-5), 3.41 (1H, dd, J=5.52, 2.81 Hz, H-6), 3.36 (1H, m, H-4), 1.28 (3H, d, J=6.38Hz, 1'-CH₃), 1.12 ppm (3H, d, J=7.25Hz, 4-CH₃).

EXAMPLE 28

Sodium (4R,5S,6S)-3-[[[[(p-hydroxymethyl)phenyl]thio]methyl]-thio]-6-[1'(R)-hydroxyethyl]-4-methyl-7-oxo-1-azabicyclo[3.2.0]hept-2-ene-2-carboxylate (Iz)

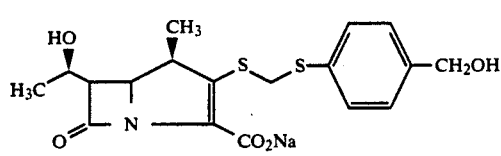

p-(Methylthio)benzyl p-nitrobenzyl carbonate

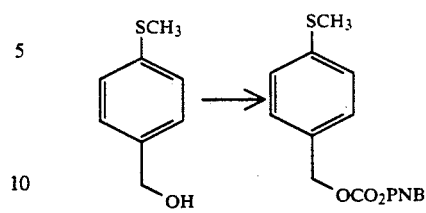

A solution of p-(methylthio)benzyl alcohol (1.0 g, 6.48 mmol), carbonyl diimidazole (1.16 g, 7.13 mmol) and sodium imidazole (0.010 g) in CH₃CN (25 mL) was stirred at 20° C. for 30 min, followed by addition of p-nitrobenzyl alcohol (1.09 g, 7.13 mmol). Stirring was continued for an additional 24 h and then the reaction mixture was evaporated to dryness. The crude carbonate was purified by silica gel chromatography (eluted with CH₂Cl₂) to afford 2.13 g (98.6%) of the title compound as a white solid, melting at 84°–86° C.

IR (CH₂Cl₂) ν$_{max}$: 1753 cm⁻¹ (—CO—);

¹H NMR (CDCl₃, 200 MHz) δ: 8.22 (2H, d, nitrobenzyl-H), 7.52 (2H, d, nitrobenzyl-H), 7.27 (4H, ABq, methylthiobenzyl-H), 5.25 (2H, s, —CH₂), 5.14 (2H, s, —CH₂—), 2.48 (3H, s, —SCH₃).

Step B p-[(Chloromethyl)thio]benzyl p-nitrobenzyl carbonate

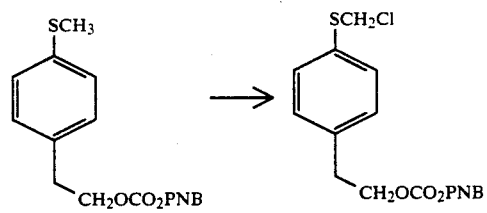

A cold (5° C.) solution of p-(methylthio)benzyl p-nitrobenzyl carbonate (1.0 g, 3 mmol) in CH₂Cl₂ (50 mL) was treated dropwise (2 min) with SO₂Cl₂ (0.425g, 3.15 mmol). After stirring the resulting solution for 30 min at 5° C., the solvent was evaporated to leave the title compound as an oil which solidified (1.10 g yield, 99.7%). The solid was used without purification in the next step.

IR (CH₂Cl₂) ν$_{max}$: 1752 cm⁻¹ (—CO—);

¹H NMR (CDCl₃, 200 MHz) δ: 8.25 (2H, d, nitrobenzyl-H), 7.54 (2H, d, nitrobenzyl-H), 7.27 (4H, ABq, methylthio benzyl-H), 5.26 2H, s, —CH₂—), 5.18 (2H, s, —CH₂—), 4.97 ppm (2H, s, —CH₂Cl).

Step C p-Nitrobenzyl (4R,5S,6S)-3-[[[[4-[[[[(p-nitrobenzyl)oxy]-carbonyl]oxy]methyl]phenyl]thio]methyl]thio]-6-[1'(R)-hydroxyethyl]-4-methyl-7-oxo-1-azabicyclo[3.2.0]-hept-2-ene-2-carboxylate

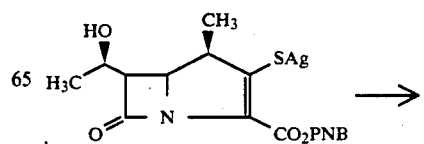

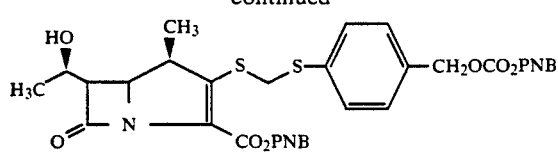

A cold (5° C.) solution of p-nitrobenzyl (4R,5S,6S)-6-1'(R)-hydroxyethyl]-4-methyl-3-silver mercapto-7-oxo-1-azabicyclo[3.2.0]hept-2-ene-2-carboxylate (0.849 g, 1.75 mmol) in dimethylformamide (15 mL) was treated with p-[(chloromethyl)thio]benzyl p-nitrobenzyl carbonate (0.736 g, 2 mmol), LiI (0.703 g, 5.25 mmol) and N,N-diisopropylethylamine (0.396 g, 3 mmol). The reaction mixture was stirred at 5° C. for 18 h, then diluted with ethyl acetate and shaken vigorously with cold dilute HCl. The mixture was filtered, the organic phase separated and the aqueous layer extracted with ethyl acetate. The organic extracts were combined, washed with brine, dried (MgSO4) and evaporated. The crude product was purified by silica gel chromatography (eluted with 0–10% CH3CN/CH2Cl2). The pertinent fractions were combined and evaporated to leave 0.638g (51.4%) of the title compound as a foam.

IR (CH2Cl2) $\nu_{max}$: 3610 (—OH), 1775 ($\beta$-lactam), 1755 (—OCO2—), 1710 cm$^{-1}$ (—CO2$^-$).

$^1$H NMR (CDCl3, 200 MHz) δ: 8.23 (2H, d, nitrobenzyl-H), 8.20 (2H, d, nitrobenzyl-H), 7.63 (2H, d, nitrobenzyl-H), 7.53 (2H, d, nitrobenzyl-H), 7.38 (4H, ABq, methylthiobenzyl-H), 5.36 (2H, ABq, nitrobenzyl-CH2), 5.26 (2H, S, —CH2—), 5.17 (2H, S, —CH2—), 4.35–4.05 (4H, m, H-5, H-1', 4.22 (2H, ABq, S—CH2—), 3.43 (1H, m, H-4), 3.26 (1H, dd, J=6.88, 2.60Hz, H-6), 1.36 (3H, d, J=6.27Hz, 1'-CH3), 1.28 ppm (3H, d, J=6.34Hz, 4-CH3).

Step D

Sodium (4R,5S,6S)-3-[[[[(p-hydroxymethyl)phenyl]methyl]thio]-6-1'(R)-hydroxyethyl]-4-methyl-7-oxo-1-azabicyclo-3.2.0]hept-2-ene-2-carboxylate (Iz)

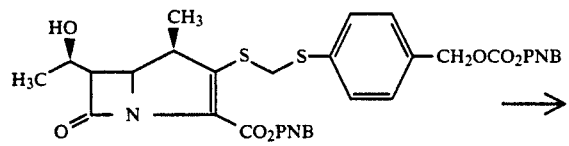

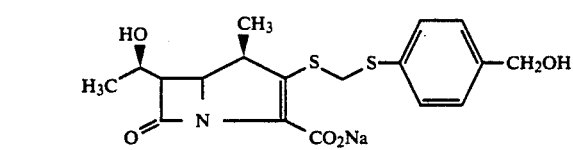

A solution of p-nitrobenzyl (4R,5S,6S)-3-[[[[4-[[[[(p-nitrobenzyl)oxy]carbonyl]oxy]methyl]phenyl]thio]methyl]-thio]-6-[1'(R)-hydroxyethyl]-4-methyl-7-oxo-1-azabicyclo[3.2.0]-hept-2-ene-2-carboxylate (0.635 g, 0.895 mmol) in tetrahydrofuran (35 mL) was added to a mixture of Et2O (35 mL) and a 0.1M NaH2PO4/NaOH buffer solution (17.8 mL, pH:7.0). The mixture was subjected to hydrogenolysis over 10% Pd/C catalyst (0.60 g) at 40 psi H2 for 3 h. Then the catalyst was filtered off and the filtrate extracted with Et2O. The aqueous phase was chromatographed on reversed phase silica gel (partisil), eluted with 0–10% CH3CN/water.

The pertinent fractions were lyophilized to yield 0.08 g (21.4%)of the title product as a white foam.

IR (Nujol) $\nu_{max}$: 1745 ($\beta$-lactam), 1590 cm$^{-1}$ (—CO2—).

$^1$H NMR (D2O, 200 MHz) δ: 7.58 (2H, d, aromatic-H), 7.38 (2H, d, aromatic-H), 4.65 (2H, s, —CH2—), 4.46–4.12 (3H, m, H-1', 4.20: 2H, ABq, —CH2S), 3.81 (1H, unresolved dd, H-5), 3.34 (1H, unresolved dd, H-6), 3.19 (1H, m, H-4), 1.26 (3H, d, J=6.29Hz, 1'-CH3), 1.08 ppm (3H, d, J=7.17Hz, 4-CH3).

EXAMPLE 29

Sodium (4R,5S,6S)-6-[1'(R)-hydroxyethyl]-4-methyl-3-[[[(1-methyltetrazol-5-yl)thio]methyl]thio]-7-oxo-1-azabicyclo[3.2 0]hept-2-ene-2-carboxylate (Iaa)

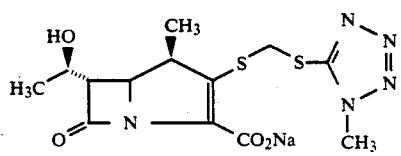

Step A

5-[(Chloromethyl)thio]-1-methyl-tetrazole

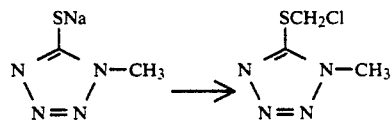

A solution of sodium 5-mercapto-1-methyltetrazole hydrate (1.38 g, 10.0 mmol) in CH3CN (50 mL) was cooled in ice and treated in one portion with bromochloromethane (6.47 g, 50 mmol). The ice-bath was removed and the reaction mixture stirred at R.T. for 18 h. Then the solvent was evaporated and the crude product purified by chromatography on silica gel (eluted with CH2Cl2) to afford 1.27 g (77%) of the title compound, m.p.: 55°–57° C.

$^1$H NMR (CDCl3) δ: 5.26 (2H, S, —CH2), 4.01 ppm (3H, S, —CH3).

Step B p-Nitrobenzyl (4R,5S,6S)-6-[1'(R)-hydroxyethyl]-4-methyl-3-[[[(1-methyltetrazol-5-yl)thio]methyl]thio]-7-oxo-1-azabicyclo[3.2.0]hept-2-ene-2-carboxylate

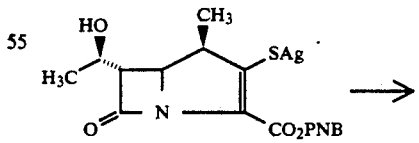

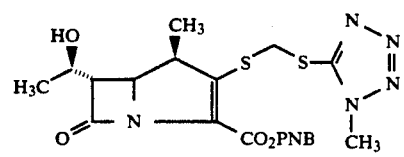

A cold solution (5° C.) of p-nitrobenzyl (4R,5S,6S)-6-[1'(R)-hydroxyethyl]-4-methyl-3-silver mercapto-7- oxo-1-azabicyclo-[3.2.0]hept-2-ene-2-carboxylate (970 mg, 2 mmol) in DMF (20 mL) was treated with 5-[(chloromethyl)thio]-1-methyl-tetrazole (362 mg, 2.2 mmol), lithium iodide (803 mg, 6 mmol) and DIPEA (427 mg, 3.3 mmol). The reaction mixture was stirred at 5° C. for 20 h, then diluted with EtOAc, shaken vigorously with cold dilute HCl and filtered. The organic phase was separated and washed three times with brine. After drying (MgSO4), the solvent was evaporated and the crude dithioacetal was purified by chromatography on silica gel [eluted with CH3CN (0→15%)/CH2Cl2] to afford 275 mg (27.1%) of the title product.

IR (CH2Cl2) $v_{max}$: 3600 (—OH), 1778 (β-lactam), 1720 (ester), 1525 cm$^{-1}$ (—NO2);

1H NMR (CDCl3) δ: 8.23 (2H, d, J=8.8Hz, Ar) 7.64 (2H, d, J=8.8Hz, Ar), 5.36 (2H, ABq, H-benzyl), 9.70 (2H, ABq, —SCH2—), 4.29 (1H, dd, J=2.66, 9.41Hz, H-5), 3.93 (3H, s, N-CH3), 3.60 (1H, dq, H-1′), 3.31 (1H, dd, J=2.68, 6.64Hz, H-6), 1.36 (3H, d, J=6.28Hz, 1′-CH3), 1.30 ppm (3H, d, J=7.29Hz, 4-CH3).

Step C

Sodium (4R,5S,6S)-6-[1′(R)-hydroxyethyl]-4-methyl-3-[[[(1-methyltetrazol-5-yl)thio]methyl]thio]-7-oxo-1-azabicyclo[3.2.0]hept-2-ene-2-carboxylate (Iaa)

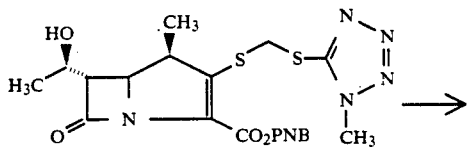

A solution of p-nitrobenzyl (4R,5S,6B)-6-[1′(R)-hydroxyethyl]-4-methyl-3-[[[(1-methyltetrazol-5-yl)-thio]methyl]thio]-7-oxo-1-azabicyclo[3.2.0]hept-2-ene-2-carboxylate (270 mg, 0.53 mmol) in THF (20 mL) was added to a mixture of Et2O (20 mL) and a 0.1M NaH2PO4/ NaOH buffer solution (pH: 7.0, 10 mL). This mixture was subjected to hydrogenolysis over 10% Pd/C (270 mg) catalyst at 40 psi H2 for 4 h. Then the catalyst was filtered off and the filtrate extracted with Et2O. The aqueous phase was chromatographed on reversed phase silica gel, eluted first with H2O and then with 5% CH3CN in H2O. The pertinent fractions were combined and lyophilized to afford 52 mg (24.8%) of the title product.

IR (Nujol) $v_{max}$: 1750 (β-lactam), 1595 cm$^{-1}$ (—CO2$^-$).

1H NMR (D2O) δ: 4.59 (2H, ABq, SCH2—), 4.27 (1H, dq, H-1 ), 4.17 (1H, dd, J=2.62, 9.36Hz, H-5), 4.05 (3H, s, —N—CH3), 3.45 (2H, m, H-6, H-4), 1.32 (3H, d, J=6.38Hz, 1′-CH3), 1.20 ppm (3H, d, J=7.26Hz, 4-CH3).

EXAMPLE 30

Sodium (4R,5S,6S)-3-[[[[(p-hydrazinocarbonyl)phenyl]thio]methyl]-thio]-6-[1′(R)-hydroxyethyl]-4-methyl-7-oxo-1-azabicyclo-3.2.0]hept-2-ene-2-carboxylate (Ibb)

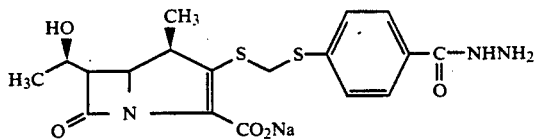

Step A

4-[(Cloromethyl)thio]benzoic acid hydrazide

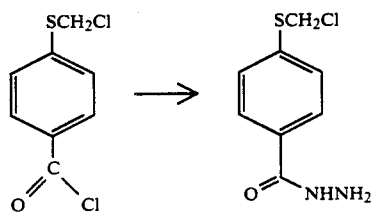

To a solution of hydrazine (0.64 g, 20 mmol) in CH3CN (15 mL) was added dropwise at room temperature a solution of 4-[(chloromethyl)thio]benzoyl chloride (2.0 g, 9.11 mmol) in CH3CN (10 mL). An exothermic reaction took place resulting in the formation of a white solid. The mixture was stirred for 30 min and then evaporated to dryness. The crude product was purified by silica gel chromatography (eluted with EtOAc) to afford 0.758 g (38.4%) of the title hydrazide as a white solid.

IR (CH2Cl2) $v_{max}$: 1673 (—CO—) 1600 cm$^{-1}$ (aromatic).

1H NMR (CDCl3, 200 MHz) δ: 7.63 (4H, ABq, aromatic-H), 5.02 ppm (2H, s, —SCH2—).

Step B p-Nitrobenzyl 2-[p-[(chloromethyl)thio]benzoyl]hydrazinecarboxylate

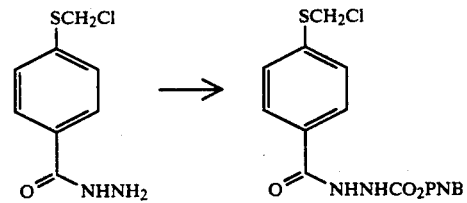

To a cold (5° C.) suspension of 4-[(chloromethyl)thio]benzoic acid hydrazide (0.433 g, 2 mmol) and p-nitrobenzylchloroformate (0.475 g, 2.2 mmol) in CH3CN (25 mL) was added N,N-diisopropylethylamine (0.285 g, 2.2 mmol) dropwise. The reaction mixture was stirred at 5° C. for 15 min and at 20° C for another 15 min. Then the solvent was evaporated and the resulting crude product was purified by silica gel chromatography (eluted with 0-10% CH3CN/CH2Cl2). The pertinent fractions were combined and evaporated to give 0.34 g (42.9%) of the title product as a yellow solid.

IR (CH$_2$Cl$_2$) $\nu_{max}$: 3510 (—NH), 1760 —CO$_2$PNB), 1695 cm$^{-1}$ (—CON ).

1H NMR (CDCl$_3$, 200 MHz) δ: 8.21 (2H, d, nitrobenzyl-H), 7.79 (2H, d, aromatic-H), 7.59 (4H, 2d, nitrobenzyl-H, aromatic-H), 5.30 (2H, s, —CH$_2$—), 5.03 (2H, S, —CH$_2$—).

Step C p-Nitrobenzyl (4R,5S,6S)-3-[[[4-[2-[[(p-nitrobenzyl)oxy]carbonyl]hydrazino]phenyl]thio]methyl]thio]-6-[1'(R)-hydroxyethyl]-4-methyl-7-oxo-1-azabicyclo-[3.2.0]hept-2-ene-2-carboxylate

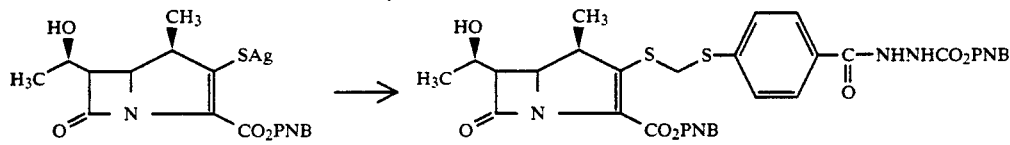

A cold (5° C.) solution of p-nitrobenzyl (4R,5S,6S)-6-[1'(R)-hydroxyethyl]-4-methyl-3-silver mercapto-7-oxo-1-azabicyclo[3.2.0] hept-2-ene-2-carboxylate (0.379 g, 0.78 mmol) in dimethylformamide (10 mL) was treated with p-nitrobenzyl 2-[p-[(chloromethyl)thio]benzoyl]hydrazine-carboxylate (0.34 g, 0.86 mmol), LiI (0.345 g, 2.58 mmol) and N,N-diisopropylethylamine (0.166 g, 1.29 mmol). After stirring at 5° C. for 18 h, the solution was diluted with ethylacetate, shaken vigorously with cold dilute HCl and filtered. The organic phase was separated and the aqueous layer extracted with ethyl acetate. The extracts were combined, washed twice with brine, dried (MgSO$_4$) and evaporated to dryness. The crude product was purified by silica gel chromatography (eluted with 0 to 10% CH$_3$CN/CH$_2$Cl$_2$ then with ethyl acetate) to give 0.227 g (39.5%) of the title product as a yellow foam.

IR (CH$_2$Cl$_2$) $\nu_{max}$: 1775 (β-lactam), 1747 (—NCO$_2$PNB), 1705 (CO$_2$PNB), 1685 cm$^{-1}$ (—CON—).

1H NMR (CDCl$_3$, 200 MHz) δ: 8.26–7.43 (12H, series of d, aromatic-H), 5.35 (2H, ABq, —CO$_2$CH$_2$—), 5.30 (2H, s, —NCO$_2$CH$_2$), 4.40–4.10 (4H, m, H-1', H-5; 4.28; 2H, Abq, —SCH$_2$—), 3.40–3.21 (2H, m, H-4; 3.23; 1H, dd, J=2.58, 6.33 Hz, H-6), 1.33 (3H, d, J=6.25Hz, 1'-CH$_3$), 1.22 ppm (3H, d, J=7.29Hz, 4-CH$_3$).

Step D

Sodium (4R,5S,6S)-3-[[[[(p-hydrazinocarbonyl)phenyl]thio]methyl]thio]-6-[1'(R)-hydroxyethyl]-4-methyl-7-oxo-1-azabicyclo[3.2.0]hept-2-ene-2-carboxylate (Ibb)

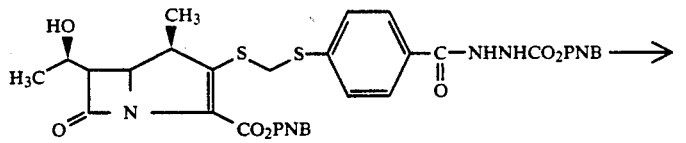

A solution of p-nitrobenzyl (4R,5S,5S)-3-[[[4-[2-[[(-p-nitrobenzyl)oxy]carbonyl]hydrazino]phenyl]thio]methyl]-6-[1'(R)-hydroxyethyl]-4-methyl-7-oxo-1-azabicyclo-[3.2.0]hept-2-ene-2-carboxylate (0.29 g, 0.393 mmol) in tetrahydrofuran (20 mL) was added to a mixture of Et$_2$O (20 mL) and 0.1M NaH$_2$PO$_4$/NaOH buffer solution (10 mL, pH:7.0). The mixture was subjected to hydrogenolysis over 10% Pd/C catalyst (0.29 g), at 40 psi H$_2$, for 4 h. At that point, the catalyst was filtered off and replaced by a fresh batch (0.175 g). The hydrogenolysis condition was maintained for an additional 2 h. Then the reaction mixture was filtered and the filtrate extracted with Et$_2$O. The aqueous phase was chromatographed on reversed phase silica gel (partisil), eluted with 0 to 5% CH$_3$CN/water. The pertinent fractions were combined and lyophilized to give a white foam (0.048 g yield, 27.4%).

IR (Nujol) $\nu_{max}$: 1750 (β-lactam), 1595 cm$^{-1}$ (—CO$_2$—).

1H NMR (D$_2$O, 200 MHz) δ: 7.67 (4H, ABq, aromatic-H), 4.38 (2H, ABq, —SCH$_2$—), 4.17 (1H, m, H-1'), 3.88 (1H, dd, J:9.13, 2.37, H-5), 3.38 (1H, dd, J=6.06, 2.49 Hz, H-6), 3.27 (1H, m, H-4), 1.27 (3H, d, J=6.36Hz, 1'-CH$_3$), 1.13 ppm (3H, d, J=7.19Hz, 4-CH$_3$).

EXAMPLE 31

Sodium (4R,5S,6S)-6-[1'(R)-hydroxyethyl]-4-methyl-3-[[[(5-methyl-1,3,4-oxadiazol-2-yl)thio]methyl]thio]-7-oxo-1-azabicyclo-3.2.0]hept-2-ene-2-carboxylate (Icc)

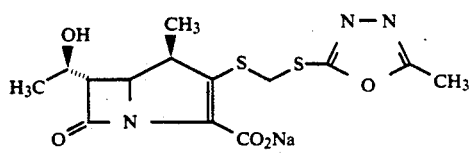

Step A

2-[(Iodomethyl)thio]-5-methyl-1,3,4-oxadiazole

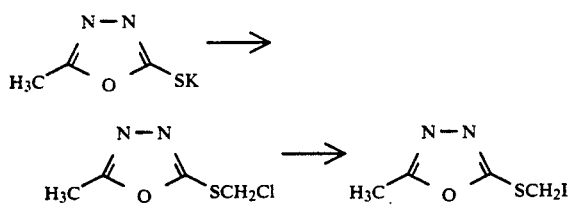

A suspension of 2-mercapto-5-methyl-1,3,4-oxadiazole potassium salt (33.0 g, 214 mmol) in CH$_3$CN (330 mL) was stirred at R.T. for 24 h in the presence of BrCH$_2$Cl (130 g, 1 mol). Then the solvent was evaporated and the residue partitioned between H$_2$O and EtOAc. The organic phase was separated, dried (MgSO$_4$) and evaporated. The residue thus obtained was redissolved in Et$_2$O; the etheral solution was treated with charcoal and filtered through a pad of Celite. Evaporation of the filtrate left 29.4 g of a colorless oil. The crude oil was dissolved in acetone (350 mL), and sodium iodide (134 g, 894 mmol) was added. The resulting mixture was refluxed for 24 h, diluted with Et$_2$O and washed with H$_2$O. The aqueous phase was reextracted with Et$_2$O. The organic extracts were combined, washed with H$_2$O and brine, dried (MgSO$_4$), treated with charcoal, filtered and finally evaporated to give 40.0 g (87.3%) of the title compound as a yellowish oil.

1H NMR (CDCl$_3$) δ: 4.66 (2H, S, —CH$_2$—), 2.56 ppm (3H, s, —CH$_3$).

Step B

Allyl (4R,5S,6S)-6-[1'(R)-hydroxyethyl]-4-methyl-3-[[[(5-methyl-1,3,4-oxadiazol-2-yl)thio]methyl]thio]-7-oxo-1-azabicyclo-[3.2.0]hept-2-ene-2-carboxylate

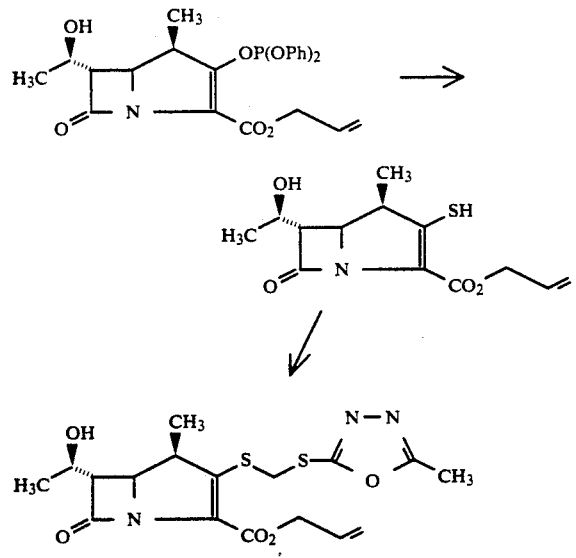

A cold (5° C.) solution of allyl (4R,5S,6S)-6-[1'(R)-hydroxyethyl]-3-(diphenylphosphono)-4-methyl-7-oxo-1-azabicyclo[ 3.2.0]hept-2-ene-2-carboxylate (75.9 g, 152 mmol) in THF (1500 mL) was treated portionwise with LiSH [10.3 g, 258 mmol, LiSH was prepared by saturating a cold (5° C.) solution of BuLi in equal volumes of hexane and THF with H$_2$S. The precipitated salt was filtered and dried.] The solution was stirred for 35 min and then 2-[(iodomethyl)thio]-5-methyl-1,3,4-oxadiazole (58.4 g, 228 mmol) was added followed by diisopropylethylamine (40 mL, 228 mmol). After the reaction mixture was stirred for 30 min, acetic acid (14 mL) and cold H$_2$O (1000 mL) was added. The product was extracted into EtOAc. The organic extract was successively washed with H$_2$O, aqueous sodium bicarbonate solution and brine, dried (MgSO$_4$) and and evaporated. The resulting crude dithioacetal was purified by chromatography on silica gel, eluted with CH$_3$CN in CH$_2$Cl$_2$ (0 to 25% CH$_3$CN), to afford 15.5 g (24.8%) of the title compound.

IR (CH$_2$Cl$_2$) $\nu_{max}$: 3600 (—OH), 1777 (β-lactam), 1715 cm$^{-1}$ (ester).

1H NMR (CDCl$_3$) δ: 6.10–4.63 (5H allyl pattern), 4.58 (2H, ABq, —SCH$_2$), 4.26 (2H, m,H-5, H-1'), 3.53 (1H, dq, H-4), 3.28 (1H, dd, J=2.63, J=6.89Hz, H-6), 2.54 (3H, s, Het-CH$_3$), 1.36 (3H, d, J=6.26Hz, 1'-CH$_3$), 1.30 ppm (3H, d, J=7.32Hz, 4-CH$_3$).

Step C

Sodium (4R,5S,6S)-6-[1'(R)-hydroxyethyl]-4-methyl-3-[[[(5-methyl-1,3,4-oxadiazol-2-yl)thio]methyl]thio]-7-oxo-1-azabicyclo-[3.2.0]hept-2-ene-2-carboxylate (Icc)

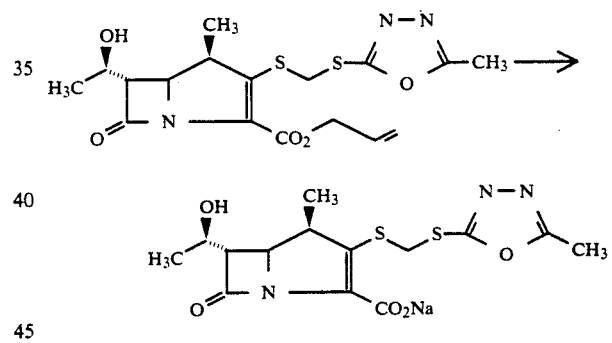

A solution of allyl (4R,5S,6S)-6-[1'(R)-hydroxyethyl]-4-methyl-3-[[[(5-methyl-1,3,4-oxadiazol-2-yl)thio]-methyl]-thio]-7-oxo-1-azabicyclo-[3.2.0]hept-2-ene-2-carboxylate (15.35 g, 37.3 mmol) in CH$_2$Cl$_2$ (130 mL) was cooled to 5° C and treated successively with Pd(PPh$_3$)$_4$ (1.0 g, 0.87 mmol), Pφ3 (100 mg, 0.38 mmol) and a solution of sodium ethyl hexanoate 0.5M (74.6 mL, 37.3 mmol) in EtOAc dropwise. After stirring at 5° C. for 90 min, the reaction mixture was extracted with cold H$_2$O (2×150 mL). The aqueous solution was chromatographed on reversed phase silica gel (BondaPak C-18), eluted with CH$_3$CN in H$_2$O (0→20% CH$_3$CN). Lyophilization of the pertinent fractions gave 13.0 g (88.6%) of the desired product.

IR (Nujol) $\nu_{max}$: 1750 (β-lactam), 1595 cm$^{-1}$ (—CO$_2$—).

$^1$H NMR (D$_2$O ) δ: 4.55 (2H, ABq, —SCH$_2$), 4.23 (1H, dq, H-1'), 4.21 (1H, dd, J=9.32, 2.58Hz, H-5), 3.50 (1H, dq, H-4), 3.46 (1H, dd, J=6.09, 2.72Hz, H-6), 2.56 (3H, s, Het-CH$_3$), 1.30 (3H, d, J=6.39Hz, 1'-CH$_3$ , 1.21 ppm (3H, d, J=7.26Hz, 3-CH$_3$).

EXAMPLE 32

Sodium (4R,5S,6S) TM 6-[1'(R)-hydroxyethyl]-4-methyl-3-[[[(5-methyl-1.3.4-thiadiazol-2-yl)thiomethylthio-7-oxo-1-azabicyclo3.2.0hept-2-ene-2-carboxylate (Idd)

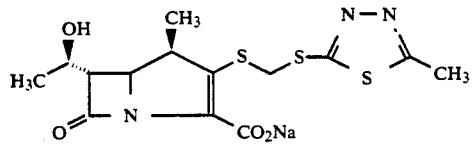

Step A

2-[(Iodomethyl)thio]-5-methyl-1,3,4-thiadiazole

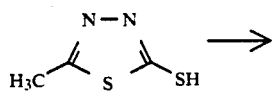

2-Mercapto-5-methyl-1,3,4-thiadiazole (41.4 g, 313 mmol) was added to an ice-bath cooled (5° C.) aqueous solution of 85% KOH (20.7 g, 313 mmol) in EtOH (160 mL). The ice bath was removed and the mixture stirred until complete dissolution occurred (30 min). The solvent was then evaporated to leave a viscous oil which solidified. The resulting potassium salt was dissolved in $CH_3CN$ (200 mL), and the solution was cooled in an ice bath and treated with bromochloromethane (121 g, 939 mmol). The ice in the bath was allowed to melt and the mixture was further stirred at R.T. for 25 h. The reaction mixture was partitioned between EtOAc and $H_2O$. The organic phase was dried ($MgSO_4$) and evaporated. The residue was purified by passing through a pad of silica gel, eluted first with $CH_2Cl_2$ and then with 5% $CH_3CN/CH_2Cl_2$ to afford 93.0 g (76.0%) of 2-[(chloromethyl)-thio]-5-methyl-1,3,4-thiadiazole.

The thiadiazole was dissolved in acetone (450 mL), cooled to 5° C. with an ice bath and treated slowly with NaI (178 g, 1.19 mol). The ice in the bath was allowed to melt and the mixture stirred at R.T. for 75 h. Acetone was mostly evaporated and the residual slurry partitioned between $Et_2O$ and $H_2O$. The etheral phase was washed with aqueous $NaHSO_3$ and $H_2O$, dried ($MgSO_4$), and evaporated. The resulting crude product was chromatographed on silica gel, eluted with $CH_2Cl_2$ and $CH_3CN$ (0→10%)/$CH_2Cl_2$ to afford 50.0 g (77.2%) of the title compound.

$^1$H NMR ($CDCl_3$) δ: 4.78 (2H, s, —$CH_2$), 2.79 ppm (3H, s, —$CH_3$).

Step B

Allyl (4R,5S,6S)-6-[1'(R)-hydroxyethyl]-4-methyl-3-[[[(5-methyl-1,3,4-thiadiazol-2-yl)thio]methyl]thio]-7-oxo-1-azabicyclo[3.2.0]hept-2-ene-2-carboxylate

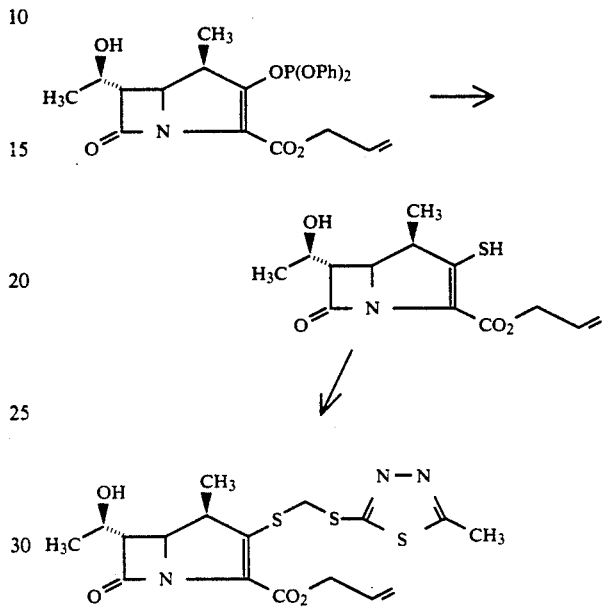

A cold (−5° C.) solution of ally (4R,5S,6S)-6-[1'(R)-hydroxyethyl]-3-(diphenylphosphono)-4-methyl-7-oxo-1-azabicyclo[3.2.0]hept-2-ene-2-carboxylate (100 g, 0.2 mol) in THF (2 l) was treated portionwise with LiSH (12.0 g, 0.3 mol). After stirring for 25 min, 2-[(iodomethyl)thio]-5-methyl-1,3,4-thiadiazole (50 g, 0.184 mol) in THF (100 mL) was added followed by DIPEA (25.9 g, 200 mmol). The reaction mixture was stirred at 0° C. for 30 min and at R.T. for 30 min. Acetic acid (15 mL) was added to the reaction mixture followed by cold $H_2O$ (2 L). The aqueous solution was extracted with EtOAc. The organic extracts were combined, washed successively with $H_2O$, $NaHCO_3$ and brine, dried ($MgSO_4$), and evaporated. The resulting crude product was purified by silica gel chromatography [eluted with $CH_3CN$ (0→60%) /$CH_2Cl_2$]. The pertinent fractions were combined and evaporated to leave a solid which was triturated in $Et_2O$ and collected by filtration to afford 29.93 g (28.0%) of the title compound.

IR ($CH_2Cl_2$) $v_{max}$: 3600 (—OH), 1775 (β-lactam), 1715 cm$^{-1}$ (ester).

$^1$H NMR ($CDCl_3$) δ: 6.1–4.6 (5H, allylic pattern) 4.67 (2H, ABq, —$SCH_2$—), 4.28–4.22 (2H, m, H-1', H-5), 3.58 (1H, dq, H-4), 3.27 (1H, dd, J=2.59, 6.85Hz, H-6), 2.76 (3H, s, Het-$CH_3$), 1.36 (3H, d, J=6.27Hz, 1'-$CH_3$), 1.30 ppm (3H, d, J=7.30Hz, 4-$CH_3$).

Step C

Sodium (4R,5S,6S)-6-[1'(R)-hydroxyethyl]-4-methyl-3-[[[(5-methyl-1,3,4-thiadiazol-2-yl)thio]methyl]thio]-7-oxo-1-azabicyclo[3.2.0]hept-2-ene-2-carboxylate (Idd)

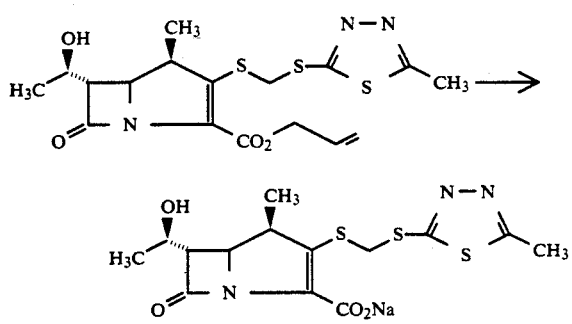

A cold (5° C.) solution of allyl (4R,5S,6S)-6-[1'(R)-hydroxyethyl]-4-methyl-3-[[[(5-methyl-1,3,4-thiadiazol-2-yl)thio]methyl]thio]--oxo-1-azabicyclo[3.2.0]hept-2-ene-2-carboxylate (23.93 g, 55.97 mmol) in $CH_2Cl_2$ (200 mL) was treated successively with $PPh_3$ (150 mg, 0.57 mmol), $Pd(PPh_3)_4$ (1.3 g, 1.13 mmol) and a 0.5M solution of ethyl hexanoate (112 mL, 56 mmol) in EtOAc. The reaction mixture was stirred at 5° C. for 2.5 h during that time a solid precipitated. After the solution was diluted with acetone (300 mL), the precipitate was collected by filtration, washed (acetone) and dried. This crude product (~30 g) was purified by chromatography on reversed phase silica gel (μBondaPak C-18), eluted first with $H_2O$ and then with $CH_3CN(0\rightarrow 10\%)/H_2O$. After lyophilization, 18.9 g (82.5%) of the title compound was recovered as a white solid.

IR (Nujol) $v_{max}$: 1750 (β-lactam), 1600 cm$^{-1}$ (ester).

$^1$H NMR ($D_2O$) δ: 4.54 (2H, ABq, —$SCH_2$), 4.26 (1H, dq, H-1'), 4.15 (1H, dd, J =2.51, 9.31Hz, H-5), 3.55–3.37 (2H, m, H-6, H-4), 2.78 (3H, s, Het-$CH_3$), 1.32 (3H, d, J=38Hz, 1'-$CH_3$), 1.20 ppm (3H, d, J=7.25Hz, 4-$CH_3$).

EXAMPLE 33

Biological Activity

In order to illustrate the potent antibacterial activity and significant oral bioavailability of the carbapenems of the present invention, Tables I, II and III show data for in vitro activities (MIC), oral in vivo activities ($PD_{50}$) and blood levels after oral administration of the representative drugs ($C_{max}$, $t_{\frac{1}{2}}$ and AUC), respectively.

I. In Vitro Activity

Table I shows Minimal Inhibitory Concentrations (MIC's) of the representative antimicrobial agents. The determination was done by using microtiter broth dilution using Nutrient broth and final bacterial inoculum of approximately 500,000 CFU/ml from overnight cultures of the bacterium. The microtiter trays were then incubated at 35° C. overnight. The MIC's were determined in μg/ml as the lowest concentration of the drug which inhibits visible growth of the bacterium.

II. Oral In Vivo Activities

The in vivo therapeutic efficacy of the representative compounds after oral administration to mice infected intraperitoneally with 0.5 ml of various bacterial suspension is shown in Table II. The values are given in PD50 (dose in mg/kg to give protection to 50% of the infected mice).

III. Pharmacokinetics

Blood levels and the half-life of selected compounds of the present invention after oral administration at 50 mg/kg in mice is shown in Table III.

TABLE 1

| | | MIC (μg/ml) Compounds | | |
|---|---|---|---|---|
| Organisms | | Ik | Icc | Idd |
| Str. Pneu. | A9525 | 0.004 | 0.001 | 0.001 |
| Staph. aur. | PenR | 0.030 | 0.030 | 0.016 |
| E. coli | A15119 | 2.000 | 0.004 | 0.008 |
| Ps. aeur. | A9843 | 63.000 | 32.00 | 32.00 |

TABLE II

Protective Effect in the Oral Treatment of Infected Mice $PD_{50}$/Treatment (mg/kg)

| Organism | Challenge (No. of Organisms) | Compounds | | | | |
|---|---|---|---|---|---|---|
| | | Iq | Ib | Icc | Idd | Ibb |
| S. pneumoniae | A-9585 | 5 × 10³ | NT | 1.40 | 0.20 | 0.3 | 16.5 |
| E. coli | A-15119 | 6 × 10⁶ | 25.0 | 3.50 | 1.40 | 3.85 | NT |
| P. mirabalis | A-9900 | 4 × 10⁶ | NT | 3.60 | NT | NT | NT |

NT = not tested

TABLE III

| | BLOOD LEVELS | | |
|---|---|---|---|
| Compound | $C_{max}$ (μg/ml) | $t_{1/2}$ (min) | AUC (μg · h/ml) |
| Ik | 40 | 33 | 34 |
| Iq | 33 | 25 | 24 |
| Ib | 27 | 25 | 21 |
| Icc | 20 | 14 | 11 |
| Idd | 12 | 24 | 10 |
| Ibb | <1 | ND | ND |

ND = Not determined

What is claimed is:

1. A compound of the formula

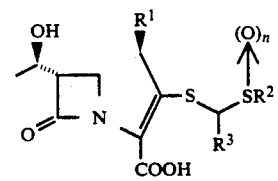

(I)

in which
R¹ is hydrogen or $C_{1-6}$ alkyl;
n is 0, 1 or 2;
R³ is hydrogen or $C_{1-6}$ alkyl;
R² is
$C_{1-6}$ alkyl, phenyl optionally substituted with cyano, —CONH$_2$, —CH$_2$OH, —CH$_2$NH$_2$, —CONHNH$_2$ or with up to 5 halogen atoms, C$_{1-6}$ alkyl or C$_{1-6}$ alkyloxy groups, phenylmethyl optionally substituted with up to 5 halogen atoms, C$_{1-6}$ alkyl or C$_{1-6}$ alkyloxy groups on the phenyl ring, or a radical represented by the formula

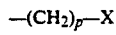
—(CH$_2$)$_p$—X in which p is 0 or 1; X is five-membered aromatic heterocyclic ring containing up to 1 sulfur, 1 oxygen or 4 nitrogen atoms, optionally substituted with a C$_{1-6}$ alkyl group, or six-membered aromatic heterocylic ring containing up to 4 nitrogen atoms, optionally substituted with a C$_{1-6}$ alkyl group, or a non-toxic pharmaceutically acceptable salt, physiologically hydrolyzable ester or solvate thereof.

2. A compound of claim 1 in which R$^1$ is hydrogen or methyl; n is 0 or 1; R$^3$ is hydrogen or C$_{1-6}$ alkyl; R$^2$ is C$_{1-6}$ alkyl, phenyl optionally substituted with cyano, —CO$_2$NH$_2$, —CH$_2$OH, —CH$_2$NH$_2$, CONHNH$_2$ or with up to 5 halogen atoms or C$_{1-6}$ alkyl groups, phenylmethyl optionally substituted with up to 5 halogen atoms or C$_{1-6}$ alkyl groups on the phenyl ring, or a radical represented by the formula

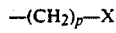
—(CH$_2$)$_p$—X in which p is 0 or 1; X is pyridinyl, furyl or a radical of the formulae

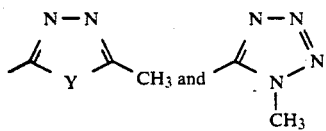

in which Y is sulfur or oxygen;

3. A compound of claim 2 in which R$^1$ is methyl, R$^3$ is hydrogen and n is 0.

4. A compound of claim 3 in which p is 0 and R$^2$ is a radical of the formula

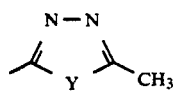

in which Y is as defined above.

5. The compound of claim 4 which is (4R,5S,6S)-6-[1'(R)-hydroxyethyl]-4-methyl-3-[[[(5-methyl-1,3,4-oxadiazol-2-yl)thio]methyl]thio]-7-oxo-1-azabicyclo-[3.2.0]hept-2-ene-2-carboxylic acid.

6. The compound of claim 4 which is (4R,5S,6S)-6-[1'(R)-hydroxyethyl)-4-methyl-3-[[[(5-methyl-1,3,4-thiadiazol-2-yl)thio]methyl]thio]-7-oxo-1-azabicyclo[3.2.0]hept-2-ene-2-carboxylic acid.

7. The compound of claim 3 which is (4R,5S,6S)-3-[[[(p-carbamoylphenyl)thio]methyl]thio]-6-[1'(R)-hydroxyethyl]-4-methyl-7-oxo-1-azabicyclo[3.2.0]-hept-2-ene-2-carboxylic acid.

8. The compound of claim 3 which is (4R,5S,6S)-3-[[[(p-cyanophenyl)thio]methyl]thio]-6-[1'(R)-hydroxyethyl]-4-methyl-7-oxo-1-azabicyclo[3.2.0]hept-2-ene-2-carboxylic acid.

9. The compound of claim 3 which is (4R,5S,6S)-3-[[[[(p-aminomethyl-)phenyl]thio]methyl]thio]-6-[1'(R)-hydroxyethyl]-4-methyl-7-oxo-1-azabicyclo[3.2.0]-hept-2-ene-2-carboxylic acid.

10. The compound of claim 3 which is (4R,5S,6S)-[1'(R)-hydroxyethyl]-3-[[[(phenylmethyl)thio]-methyl]-thio]-4-methyl-7-oxo-1-azabicyclo[3.2.0]hept-2-ene-2-carboxylic acid.

11. The compound of claim 3 which is (4R,5S,6S)-3-[[[[(p-hydroxymethyl)phenyl]thio]methyl]thio]-6-[1'(R)-hydroxyethyl]-4-methyl-7-oxo-1-azabicyclo[3.2.0]-hept-2-ene-2-carboxylic acid.

12. The compound of claim 3 which is (4R,5S,6S)-6-[1'(R)-hydroxyethyl]-4-methyl-3-[[[(1-methyltetrazol-5-yl)thio]methyl]thio]-7-oxo-1-azabicyclo[3.2.0]hept-2-ene-2-carboxylic acid.

13. The compound of claim 3 which is (4R,5S,6S)-3-[[[[(p-hydrazinocarbonyl)phenyl]thio]methyl]-thio]-6-[1'(R)-hydroxyethyl]-4-methyl-7-oxo-1-azabicyclo[3.2.0]hept-2-ene-2-carboxylic acid.

14. The compound of claim 3 which is (4R,5S,6S)-6-[1'(R)-hydroxyethyl]-4-methyl-3-[[(methylthio)methyl]thio]-7-oxo-1-azabicyclo[3.2.0]-hept-2-ene-2-carboxylic acid.

15. The compound of claim 3 which is (4R,5S,6S)-6-[1'(R)-hydroxyethyl]-4-methyl-3-[[[[(pyridin-3-yl)methyl]thio]methyl]thio]-7-oxo-1-azabicyclo[3.2.0]-hept-2-ene-2-carboxylic acid.

16. The compound of claim 3 which is (4R,5S,6S)-3-[[[(3,4-dichlorophenyl)thio]methyl]thio]-6-[1'(R)-hydroxyethyl]-4-methyl-7-oxo-1-azabicyclo[3.2.0]hept-2-ene-2-carboxylic acid.

17. The compound of claim 3 which is (4R,5S,6S)-6-[1'(R)-hydroxyethyl]-4-methyl-3-[[[(2,3,4,5,6-pentafluorophenyl)thio]methyl]thio]-7-oxo-1-azabicyclo[3.2.0]hept-2-ene-2-carboxylic acid.

18. The compound of claim 3 which is (4R,5S,6S)-[1'(R)-hydroxyethyl]-3-[[[(isopropylthio)-methyl]thio]-4-methyl-7-oxo-1-azabicyclo[3.2.0]hept-2-ene-2-carboxylic acid.

19. The compound of claim 3-which is (4R,5S,6S)-[1'(R)-hydroxyethyl]-3-[[[[(furan-2-yl)methyl]-thio]methyl]thio]-4-methyl-7-oxo-1-azabicyclo[3.2.0]hept-2-ene-2-carboxylic acid.

20. The compound of claim 3 which is (4R,5S,6S)-6-[1'(R)-hydroxyethyl]-4-methyl-3-[[[(pyridin-4-yl)thio]methyl]thio]-7-oxo-1-azabicyclo-[3.2.0]hept-2-ene-2-carboxylic acid.

21. The compound of claim 3 which is (4R,5S,6S)-6-[1'(R)-hydroxyethyl]-4-methyl-3-[[[(pyridin-2-yl)thio]methyl]thio]-7-oxo-1-azabicyclo-[3.2.0]hept-2-ene-2-carboxylic acid.

22. The compound of claim 3 which is (4R,5S,6S)-6-[1'(R)-hydroxyethyl]-4-methyl-3-[[[(pyridin-3-yl)thio]methyl]thio]-7-oxo-1-azabicyclo[3.2.0]hept-2-ene-2-carboxylic acid.

23. The compound of claim 3 which is (4R,5S,6S)-6-[1'(R)-hydroxyethyl]-4-methyl-3-[[[(p-chlorophenyl)-thio]methyl]thio]-7-oxo-1-azabicyclo[3.2.0]hept-2-ene-2-carboxylic acid.

24. The compound of claim 3 which is (4R,5S,6S)-6-[1'(R)-hydroxyethyl]-4-methyl-3-[[(phenylthio)-methyl]thio]-7-oxo-1-azabicyclo[3.2.0]hept-2-ene-2-carboxylic acid.

25. A compound of claim 2 in which R$^1$ is methyl, R$^3$ is hydrogen and n is 1.

26. The compound of claim 25 which is (4R,5S,6S)-3-[[[(p-chlorophenyl)sulfinyl]methyl]thio]-6-[1'(R)- hydroxyethyl]-4-methyl-7-oxo-1-azabicyclo[3.2.0]-hept-2-ene-2-carboxylic acid.

27. The compound of claim 25 which is (4R,5S,6S)-6-[1'(R)-hydroxyethyl]-4-methyl-3-[[[[(pyridin-3-yl)methyl]sulfinyl]methyl]thio]-7-oxo-1-azabicyclo[3.2.0]-hept-2-ene-2-carboxylic acid.

28. The compound of claim 25 which is (4R,5S,6S)-6-[1'(R)-hydroxyethyl]-4-methyl-3-[[(methylsulfinyl)methyl]thio]-7-oxo-1-azabicyclo[3.2.0]hept-2-ene-2-carboxylic acid.

29. A compound of claim 2 in which $R^1$ and $R^3$ are hydrogen and n is 0.

30. The compound of claim 29 which is (5R,6S)-6-[1'(R)-hydroxyethyl]-3-[[[(pyridin-3-yl)thio]-methyl]-thio]-7-oxo-1-azabicyclo[3.2.0]hept-2-ene-2-carboxylic acid.

31. The compound of claim 29 which is (5R,6S)-6-[1'(R)-hydroxyethyl]-3-[[(methylthio)methyl]-thio]-7-oxo-1-azabicyclo[3.2.0]hept-2-ene-2-carboxylic acid.

32. The compound of claim 29 which is (5R,6S)-6-[1'(R)-hydroxyethyl]-3-[[[(pyridin-2-yl)thio]-methyl]-thio]-7-oxo-1-azabicyclo[3.2.0]hept-2-ene-2-carboxylic acid.

33. The compound of claim 29 which is (5R,6S)-6-[1'(R)-hydroxyethyl]-3-[[[(pyridin-4-yl)thio]-methyl]-thio]-7-oxo-1-azabicyclo[3.2.0]hept-2-ene-2-carboxylic acid.

34. The compound of claim 29 which is (5R,6S)-6-[1'(R)-hydroxyethyl]-3-[[[(p-chlorophenyl)thio]-methyl]thio]-7-oxo-1-azabicyclo[3.2.0]hept-2-ene-2-carboxylic acid.

35. A compound of claim 2 in which $R^1$ is methyl, $R^3$ is methyl and n is 0.

36. The compound of claim 35 which is (4R,5S,6S)-6-[1'(R)-hydroxyethyl]-4-methyl-3-[[1(R)-(methylthio)ethyl]thio]-7-oxo-1-azabicyclo[3.2.0]hept-2-ene-2-carboxylic acid.

37. The compound of claim 35 which is (4R,5S,6S)-6-[1'(R)-hydroxyethyl]-4-methyl-3-[[1(S)-(methylthio)ethyl]thio]-7-oxo-1-azabicyclo[3.2.0]hept-2-ene-2-carboxylic acid.

38. A pharmaceutical composition comprising an antibacterial effective amount of a compound of claim 1 and a pharmaceutically acceptable carrier or diluent.

39. A method for treating bacterial infection in a mammal, which comprises administering to said mammal an antibacterial effective amount of a compound of claim 1.

* * * * *